US012599480B2

(12) United States Patent
Oba et al.

(10) Patent No.: US 12,599,480 B2
(45) Date of Patent: Apr. 14, 2026

(54) PERCUTANEOUS MITRAL VALVE REPLACEMENT DEVICE

(71) Applicant: EDWARDS LIFESCIENCES CORPORATION, Irvine, CA (US)

(72) Inventors: Travis Zenyo Oba, Yorba Linda, CA (US); Seung-Beom Yi, Mission Viejo, CA (US); Lauren R. Freschauf, Mission Viejo, CA (US); Juan Valencia, Fullerton, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 0 days.

(21) Appl. No.: 18/510,534

(22) Filed: Nov. 15, 2023

(65) Prior Publication Data

US 2024/0081986 A1 Mar. 14, 2024

Related U.S. Application Data

(60) Continuation of application No. 16/597,460, filed on Oct. 9, 2019, now Pat. No. 11,850,147, which is a
(Continued)

(51) Int. Cl.
*A61F 2/24* (2006.01)
*A61B 17/00* (2006.01)

(52) U.S. Cl.
CPC ...... *A61F 2/2418* (2013.01); *A61B 17/00234* (2013.01); *A61F 2/2433* (2013.01);
(Continued)

(58) Field of Classification Search
CPC ............ A61F 2/2418; A61F 2220/0016; A61F 2220/0075; A61F 2230/0034; A61F 2250/0097; A61F 2/2439; A61F 2/2436
See application file for complete search history.

(56) References Cited

U.S. PATENT DOCUMENTS 3,409,013 A 11/1968 Berry
3,472,230 A 10/1969 Fogarty
(Continued)

FOREIGN PATENT DOCUMENTS

CA 2304325 C 5/2008
DE 2246526 A1 3/1973
(Continued)

OTHER PUBLICATIONS

Andersen, et al., "Transluminal implantation of artificial heart valves. Description of a new expandable aortic valve and initial results with implantation by catheter technique in closed chest pigs." European Heart Journal (1992), 13, 704-708.
(Continued)

*Primary Examiner* — Brian E Pellegrino
(74) *Attorney, Agent, or Firm* — Thomas C. Richardson

(57) ABSTRACT

A prosthetic heart valve includes an outer frame, a cover, an inner frame, and a valve structure. The outer frame includes a main body and an atrial flange. The main body includes a plurality of struts forming a plurality of circumferential rows of cells, a plurality of rows of barbs extending from junctions of the struts, the atrial flange extending radially outwardly and in an atrial direction from the inflow end of the main body. The atrial flange includes an oval shape corresponding to a shape of the patient's native mitral valve anatomy. The cover is disposed on a radially inner side of the atrial flange and on a radially outer side of the atrial flange. The inner frame is disposed within the outer frame and has a cylindrical shape. The valve structure is coupled to the inner frame and includes a plurality of leaflets.

10 Claims, 19 Drawing Sheets

Related U.S. Application Data division of application No. 15/134,172, filed on Apr. 20, 2016, now Pat. No. 10,441,416.

(60) Provisional application No. 62/264,224, filed on Dec. 7, 2015, provisional application No. 62/150,431, filed on Apr. 21, 2015.

(52) U.S. Cl.
CPC .. *A61F 2/2436* (2013.01); *A61B 2017/00243* (2013.01); *A61F 2210/0014* (2013.01); *A61F 2220/0016* (2013.01); *A61F 2220/0075* (2013.01); *A61F 2230/0065* (2013.01); *A61F 2250/0059* (2013.01); *A61F 2250/0063* (2013.01); *A61F 2250/0069* (2013.01)

(56) References Cited

U.S. PATENT DOCUMENTS

| | | | |
|---|---|---|---|
| 3,548,417 A | 12/1970 | Kischer et al. |
| 3,587,115 A | 6/1971 | Shiley |
| 3,657,744 A | 4/1972 | Ersek |
| 3,671,979 A | 6/1972 | Moulopoulos |
| 3,714,671 A | 2/1973 | Edwards et al. |
| 3,739,402 A | 6/1973 | Cooley et al. |
| 3,755,823 A | 9/1973 | Hancock |
| 4,011,947 A | 3/1977 | Sawyer |
| 4,035,849 A | 7/1977 | Angell et al. |
| 4,056,854 A | 11/1977 | Boretos et al. |
| 4,079,468 A | 3/1978 | Liotta et al. |
| 4,106,129 A | 8/1978 | Carpentier et al. |
| 4,204,283 A | 5/1980 | Bellhouse et al. |
| 4,222,126 A | 9/1980 | Boretos et al. |
| 4,265,694 A | 5/1981 | Boretos et al. |
| 4,297,749 A | 11/1981 | Davis et al. |
| 4,339,831 A | 7/1982 | Johnson |
| 4,340,977 A | 7/1982 | Brownlee et al. |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,470,157 A | 9/1984 | Love |
| 4,477,930 A | 10/1984 | Totten et al. |
| 4,490,859 A | 1/1985 | Black et al. |
| 4,535,483 A | 8/1985 | Klawitter et al. |
| 4,553,545 A | 11/1985 | Maass et al. |
| 4,574,803 A | 3/1986 | Storz |
| 4,592,340 A | 6/1986 | Boyles |
| 4,605,407 A | 8/1986 | Black et al. |
| 4,612,011 A | 9/1986 | Kautzky |
| 4,643,732 A | 2/1987 | Pietsch et al. |
| 4,655,771 A | 4/1987 | Wallsten |
| 4,692,164 A | 9/1987 | Dzemeshkevich et al. |
| 4,733,665 A | 3/1988 | Palmaz |
| 4,759,758 A | 7/1988 | Gabbay |
| 4,762,128 A | 8/1988 | Rosenbluth |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,829,990 A | 5/1989 | Thuroff et al. |
| 4,851,001 A | 7/1989 | Taheri |
| 4,856,516 A | 8/1989 | Hillstead |
| 4,865,600 A | 9/1989 | Carpentier et al. |
| 4,878,495 A | 11/1989 | Grayzel |
| 4,878,906 A | 11/1989 | Lindemann et al. |
| 4,883,458 A | 11/1989 | Shiber |
| 4,922,905 A | 5/1990 | Strecker |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Samuels |
| 5,059,177 A | 10/1991 | Towne et al. |
| 5,080,668 A | 1/1992 | Bolz et al. |
| 5,085,635 A | 2/1992 | Cragg |
| 5,089,015 A | 2/1992 | Ross |
| 5,108,370 A | 4/1992 | Walinsky |
| 5,152,771 A | 10/1992 | Sabbaghian et al. |
| 5,163,953 A | 11/1992 | Vince |
| 5,167,628 A | 12/1992 | Boyles |
| 5,192,297 A | 3/1993 | Hull |
| 5,232,446 A | 8/1993 | Arney |
| 5,266,073 A | 11/1993 | Wall |
| 5,282,847 A | 2/1994 | Trescony et al. |
| 5,295,958 A | 3/1994 | Shturman |
| 5,326,371 A | 7/1994 | Love et al. |
| 5,332,402 A | 7/1994 | Teitelbaum |
| 5,360,444 A | 11/1994 | Kusuhara |
| 5,370,685 A | 12/1994 | Stevens |
| 5,397,351 A | 3/1995 | Pavcnik et al. |
| 5,411,055 A | 5/1995 | Kane |
| 5,411,522 A | 5/1995 | Trott |
| 5,411,552 A | 5/1995 | Andersen et al. |
| 5,415,667 A | 5/1995 | Frater |
| 5,443,446 A | 8/1995 | Shturman |
| 5,480,424 A | 1/1996 | Cox |
| 5,500,014 A | 3/1996 | Quijano et al. |
| 5,545,209 A | 8/1996 | Roberts et al. |
| 5,545,214 A | 8/1996 | Stevens |
| 5,549,665 A | 8/1996 | Vesely et al. |
| 5,554,185 A | 9/1996 | Block et al. |
| 5,571,175 A | 11/1996 | Vanney et al. |
| 5,591,185 A | 1/1997 | Kilmer et al. |
| 5,599,305 A | 2/1997 | Hermann et al. |
| 5,607,464 A | 3/1997 | Trescony et al. |
| 5,609,626 A | 3/1997 | Quijano et al. |
| 5,639,274 A | 6/1997 | Fischell et al. |
| 5,665,115 A | 9/1997 | Cragg |
| 5,697,382 A | 12/1997 | Love et al. |
| 5,716,417 A | 2/1998 | Girard et al. |
| 5,728,068 A | 3/1998 | Leone et al. |
| 5,749,890 A | 5/1998 | Shaknovich |
| 5,756,476 A | 5/1998 | Epstein et al. |
| 5,769,812 A | 6/1998 | Stevens et al. |
| 5,800,508 A | 9/1998 | Goicoechea et al. |
| 5,840,081 A | 11/1998 | Andersen et al. |
| 5,855,597 A | 1/1999 | Jayaraman |
| 5,855,601 A | 1/1999 | Bessler et al. |
| 5,855,602 A | 1/1999 | Angell |
| 5,906,619 A | 5/1999 | Olson et al. |
| 5,925,063 A | 7/1999 | Khosravi |
| 5,957,949 A | 9/1999 | Leonhardt et al. |
| 5,968,068 A | 10/1999 | Dehdashtian et al. |
| 6,027,525 A | 2/2000 | Suh et al. |
| 6,042,607 A | 3/2000 | Williamson et al. |
| 6,086,612 A | 7/2000 | Jansen |
| 6,113,631 A | 9/2000 | Jansen |
| 6,132,473 A | 10/2000 | Williams et al. |
| 6,168,614 B1 | 1/2001 | Andersen et al. |
| 6,171,335 B1 | 1/2001 | Wheatley et al. |
| 6,174,327 B1 | 1/2001 | Mertens et al. |
| 6,210,408 B1 | 4/2001 | Chandrasekaran et al. |
| 6,217,585 B1 | 4/2001 | Houser et al. |
| 6,221,091 B1 | 4/2001 | Khosravi |
| 6,231,602 B1 | 5/2001 | Carpentier et al. |
| 6,245,040 B1 | 6/2001 | Inderbitzen et al. |
| 6,245,102 B1 | 6/2001 | Jayaraman |
| 6,251,093 B1 | 6/2001 | Valley et al. |
| 6,287,339 B1 | 9/2001 | Vazquez et al. |
| 6,299,637 B1 | 10/2001 | Shaolian et al. |
| 6,302,906 B1 | 10/2001 | Goicoechea et al. |
| 6,306,141 B1 | 10/2001 | Jervis |
| 6,312,465 B1 | 11/2001 | Griffin et al. |
| 6,338,740 B1 | 1/2002 | Carpentier |
| 6,350,277 B1 | 2/2002 | Kocur |
| 6,358,277 B1 | 3/2002 | Duran |
| 6,379,372 B1 | 4/2002 | Dehdashtian et al. |
| 6,425,916 B1 | 7/2002 | Garrison et al. |

(56)  References Cited

U.S. PATENT DOCUMENTS

| | | | |
|---|---|---|---|
| 6,440,164 B1 | 8/2002 | DiMatteo et al. |
| 6,454,799 B1 | 9/2002 | Schreck |
| 6,458,153 B1 | 10/2002 | Bailey et al. |
| 6,461,382 B1 | 10/2002 | Cao |
| 6,468,660 B2 | 10/2002 | Ogle et al. |
| 6,482,228 B1 | 11/2002 | Norred |
| 6,488,704 B1 | 12/2002 | Connelly et al. |
| 6,527,800 B1 | 3/2003 | McGuckin et al. |
| 6,527,979 B2 | 3/2003 | Constantz et al. |
| 6,540,782 B1 | 4/2003 | Snyders |
| 6,569,196 B1 | 5/2003 | Vesely |
| 6,575,959 B1 | 6/2003 | Sarge et al. |
| 6,582,462 B1 | 6/2003 | Andersen et al. |
| 6,605,112 B1 | 8/2003 | Moll et al. |
| 6,610,088 B1 | 8/2003 | Gabbay |
| 6,629,534 B1 | 10/2003 | St. Goar et al. |
| 6,676,698 B2 | 1/2004 | McGuckin et al. |
| 6,695,878 B2 | 2/2004 | McGuckin et al. |
| 6,712,836 B1 | 3/2004 | Berg et al. |
| 6,716,207 B2 | 4/2004 | Farnholtz |
| 6,729,356 B1 | 5/2004 | Baker et al. |
| 6,730,118 B2 | 5/2004 | Spenser et al. |
| 6,733,525 B2 | 5/2004 | Yang et al. |
| 6,746,422 B1 | 6/2004 | Noriega et al. |
| 6,749,560 B1 | 6/2004 | Konstorum et al. |
| 6,767,362 B2 | 7/2004 | Schreck |
| 6,780,200 B2 | 8/2004 | Jansen |
| 6,790,229 B1 | 9/2004 | Berreklouw |
| 6,790,230 B2 | 9/2004 | Beyersdorf et al. |
| 6,830,584 B1 | 12/2004 | Seguin |
| 6,875,231 B2 | 4/2005 | Anduiza et al. |
| 6,893,460 B2 | 5/2005 | Spenser et al. |
| 6,908,481 B2 | 6/2005 | Cribier |
| 6,974,476 B2 | 12/2005 | McGuckin et al. |
| 7,018,406 B2 | 3/2006 | Seguin et al. |
| 7,186,265 B2 | 3/2007 | Sharkawy et al. |
| 7,192,440 B2 | 3/2007 | Andreas et al. |
| 7,198,646 B2 | 4/2007 | Figulla et al. |
| 7,201,772 B2 | 4/2007 | Schwammenthal et al. |
| 7,276,078 B2 | 10/2007 | Spenser et al. |
| 7,276,084 B2 | 10/2007 | Yang et al. |
| 7,318,278 B2 | 1/2008 | Zhang et al. |
| 7,374,571 B2 | 5/2008 | Pease et al. |
| 7,381,210 B2 | 6/2008 | Zarbatany et al. |
| 7,381,219 B2 | 6/2008 | Salahieh et al. |
| 7,393,360 B2 | 7/2008 | Spenser et al. |
| 7,429,269 B2 | 9/2008 | Schwammenthal et al. |
| 7,442,204 B2 | 10/2008 | Schwammenthal et al. |
| 7,445,631 B2 | 11/2008 | Salahieh et al. |
| 7,462,191 B2 | 12/2008 | Spenser et al. |
| 7,510,575 B2 | 3/2009 | Spenser et al. |
| 7,524,330 B2 | 4/2009 | Berreklouw |
| 7,530,253 B2 | 5/2009 | Spenser et al. |
| 7,553,324 B2 | 6/2009 | Andreas et al. |
| 7,579,381 B2 | 8/2009 | Dove |
| 7,585,321 B2 | 9/2009 | Cribier |
| 7,618,446 B2 | 11/2009 | Andersen et al. |
| 7,621,948 B2 | 11/2009 | Herrmann et al. |
| 7,704,222 B2 | 4/2010 | Wilk et al. |
| 7,736,327 B2 | 6/2010 | Wilk et al. |
| 7,748,389 B2 | 7/2010 | Salahieh et al. |
| 7,753,949 B2 | 7/2010 | Lamphere et al. |
| 7,806,919 B2 | 10/2010 | Bloom et al. |
| 7,824,443 B2 | 11/2010 | Salahieh et al. |
| 7,837,727 B2 | 11/2010 | Goetz et al. |
| 7,892,281 B2 | 2/2011 | Seguin et al. |
| 7,914,569 B2 | 3/2011 | Nguyen et al. |
| 7,914,575 B2 | 3/2011 | Guyenot et al. |
| 7,959,672 B2 | 6/2011 | Salahieh et al. |
| 7,972,378 B2 | 7/2011 | Tabor et al. |
| 7,981,151 B2 | 7/2011 | Rowe |
| 7,993,392 B2 | 8/2011 | Righini et al. |
| 7,993,394 B2 | 8/2011 | Hariton et al. |
| 8,007,992 B2 | 8/2011 | Tian et al. |
| 8,016,877 B2 | 9/2011 | Seguin et al. |
| 8,029,556 B2 | 10/2011 | Rowe |
| 8,052,750 B2 | 11/2011 | Tuval et al. |
| 8,070,800 B2 | 12/2011 | Lock et al. |
| 8,070,802 B2 | 12/2011 | Lamphere et al. |
| 8,075,615 B2 | 12/2011 | Eberhardt et al. |
| 8,080,054 B2 | 12/2011 | Rowe |
| 8,092,520 B2 | 1/2012 | Quadri |
| 8,092,521 B2 | 1/2012 | Figulla et al. |
| 8,109,996 B2 | 2/2012 | Stacchino et al. |
| 8,118,866 B2 | 2/2012 | Herrmann et al. |
| 8,136,218 B2 | 3/2012 | Millwee et al. |
| 8,137,398 B2 | 3/2012 | Tuval et al. |
| 8,157,852 B2 | 4/2012 | Bloom et al. |
| 8,167,932 B2 | 5/2012 | Bourang et al. |
| 8,167,934 B2 | 5/2012 | Styrc et al. |
| 8,182,530 B2 | 5/2012 | Huber |
| 8,206,437 B2 | 6/2012 | Bonhoeffer et al. |
| 8,216,174 B2 | 7/2012 | Wilk et al. |
| 8,216,301 B2 | 7/2012 | Bonhoeffer et al. |
| 8,219,229 B2 | 7/2012 | Cao et al. |
| 8,220,121 B2 | 7/2012 | Hendriksen et al. |
| 8,236,045 B2 | 8/2012 | Benichou et al. |
| 8,246,675 B2 | 8/2012 | Zegdi |
| 8,246,678 B2 | 8/2012 | Salahieh et al. |
| 8,252,051 B2 | 8/2012 | Chau et al. |
| 8,252,052 B2 | 8/2012 | Salahieh et al. |
| 8,287,584 B2 | 10/2012 | Salahieh et al. |
| 8,313,525 B2 | 11/2012 | Tuval et al. |
| 8,317,858 B2 | 11/2012 | Straubinger et al. |
| 8,323,335 B2 | 12/2012 | Rowe et al. |
| 8,337,541 B2 | 12/2012 | Quadri et al. |
| 8,353,953 B2 | 1/2013 | Giannetti et al. |
| 8,398,704 B2 | 3/2013 | Straubinger et al. |
| 8,403,983 B2 | 3/2013 | Quadri et al. |
| 8,414,644 B2 | 4/2013 | Quadri et al. |
| 8,414,645 B2 | 4/2013 | Dwork et al. |
| 8,416,643 B2 | 4/2013 | Magee |
| 8,444,689 B2 | 5/2013 | Zhang |
| 8,449,599 B2 | 5/2013 | Chau et al. |
| 8,454,685 B2 | 6/2013 | Hariton et al. |
| 8,460,368 B2 | 6/2013 | Taylor et al. |
| 8,460,370 B2 | 6/2013 | Zakay et al. |
| 8,470,023 B2 | 6/2013 | Eidenschink et al. |
| 8,470,028 B2 | 6/2013 | Thornton et al. |
| 8,475,521 B2 | 7/2013 | Suri et al. |
| 8,475,523 B2 | 7/2013 | Duffy |
| 8,479,380 B2 | 7/2013 | Malewicz et al. |
| 8,491,650 B2 | 7/2013 | Wiemeyer et al. |
| 8,500,733 B2 | 8/2013 | Watson |
| 8,500,798 B2 | 8/2013 | Rowe et al. |
| 8,511,244 B2 | 8/2013 | Holecek et al. |
| 8,512,401 B2 | 8/2013 | Murray et al. |
| 8,518,096 B2 | 8/2013 | Nelson |
| 8,518,106 B2 | 8/2013 | Duffy et al. |
| 8,562,663 B2 | 10/2013 | Mearns et al. |
| 8,579,963 B2 | 11/2013 | Tabor |
| 8,579,964 B2 | 11/2013 | Lane et al. |
| 8,591,570 B2 | 11/2013 | Revuelta et al. |
| 8,617,236 B2 | 12/2013 | Paul et al. |
| 8,640,521 B2 | 2/2014 | Righini et al. |
| 8,647,381 B2 | 2/2014 | Essinger et al. |
| 8,652,145 B2 | 2/2014 | Maimon et al. |
| 8,652,201 B2 | 2/2014 | Oberti et al. |
| 8,652,202 B2 | 2/2014 | Alon et al. |
| 8,652,203 B2 | 2/2014 | Quadri et al. |
| 8,668,733 B2 | 3/2014 | Haug et al. |
| 8,679,174 B2 | 3/2014 | Ottma et al. |
| 8,679,404 B2 | 3/2014 | Liburd et al. |
| 8,685,086 B2 | 4/2014 | Navia et al. |
| 8,721,708 B2 | 5/2014 | Sèguin et al. |
| 8,721,714 B2 | 5/2014 | Kelley |
| 8,728,154 B2 | 5/2014 | Alkhatib |
| 8,728,155 B2 | 5/2014 | Montorfano et al. |
| 8,740,974 B2 | 6/2014 | Lambrecht et al. |
| 8,740,976 B2 | 6/2014 | Tran et al. |
| 8,747,458 B2 | 6/2014 | Tuval et al. |
| 8,747,459 B2 | 6/2014 | Nguyen et al. |
| 8,758,432 B2 | 6/2014 | Solem |
| 8,764,818 B2 | 7/2014 | Gregg |

(56) References Cited

U.S. PATENT DOCUMENTS

| | | | |
|---|---|---|---|
| 8,771,344 B2 | 7/2014 | Tran et al. |
| 8,778,020 B2 | 7/2014 | Gregg et al. |
| 8,784,337 B2 | 7/2014 | Voeller et al. |
| 8,784,478 B2 | 7/2014 | Tuval et al. |
| 8,784,481 B2 | 7/2014 | Alkhatib et al. |
| 8,790,387 B2 | 7/2014 | Nguyen et al. |
| 8,795,357 B2 | 8/2014 | Yohanan et al. |
| 8,808,356 B2 | 8/2014 | Braido et al. |
| 8,828,078 B2 | 9/2014 | Salahieh et al. |
| 8,828,079 B2 | 9/2014 | Thielen et al. |
| 8,834,564 B2 | 9/2014 | Tuval et al. |
| 8,858,620 B2 | 10/2014 | Salahieh et al. |
| 8,870,948 B1 | 10/2014 | Erzberger et al. |
| 8,870,950 B2 | 10/2014 | Hacohen |
| 8,876,893 B2 | 11/2014 | Dwork et al. |
| 8,911,455 B2 | 12/2014 | Quadri et al. |
| 8,926,693 B2 | 1/2015 | Duffy et al. |
| 8,926,694 B2 | 1/2015 | Costello |
| 8,939,960 B2 | 1/2015 | Rosenman et al. |
| 8,945,209 B2 | 2/2015 | Bonyuet et al. |
| 8,961,593 B2 | 2/2015 | Bonhoeffer et al. |
| 8,961,595 B2 | 2/2015 | Alkhatib |
| 8,974,524 B2 | 3/2015 | Yeung et al. |
| 8,979,922 B2 | 3/2015 | Jayasinghe et al. |
| 8,986,375 B2 | 3/2015 | Garde et al. |
| 8,998,980 B2 | 4/2015 | Shipley et al. |
| 9,005,273 B2 | 4/2015 | Salahieh et al. |
| 9,011,521 B2 | 4/2015 | Haug et al. |
| 9,011,523 B2 | 4/2015 | Seguin |
| 9,011,524 B2 | 4/2015 | Eberhardt |
| 9,028,545 B2 | 5/2015 | Taylor |
| 9,034,032 B2 | 5/2015 | McLean et al. |
| 9,055,937 B2 | 6/2015 | Rowe et al. |
| 9,066,801 B2 | 6/2015 | Kovalsky et al. |
| 9,078,749 B2 | 7/2015 | Lutter et al. |
| 9,078,751 B2 | 7/2015 | Naor |
| 9,125,738 B2 | 9/2015 | Figulla et al. |
| 9,173,737 B2 | 11/2015 | Hill et al. |
| 9,180,004 B2 | 11/2015 | Alkhatib |
| 9,186,249 B2 | 11/2015 | Rolando et al. |
| 9,277,990 B2 | 3/2016 | Klima et al. |
| 9,277,993 B2 | 3/2016 | Gamarra et al. |
| 9,289,291 B2 | 3/2016 | Gorman et al. |
| 9,295,551 B2 | 3/2016 | Straubinger et al. |
| 9,445,897 B2 | 9/2016 | Bishop et al. |
| 9,456,877 B2 | 10/2016 | Weitzner et al. |
| 9,681,968 B2 | 6/2017 | Goetz et al. |
| 9,687,345 B2 | 6/2017 | Rabito et al. |
| 9,700,329 B2 | 7/2017 | Metzger et al. |
| 9,700,411 B2 | 7/2017 | Klima et al. |
| 9,724,083 B2 | 8/2017 | Quadri et al. |
| 9,730,790 B2 | 8/2017 | Quadri et al. |
| 9,730,791 B2 | 8/2017 | Ratz et al. |
| 9,795,479 B2 | 10/2017 | Lim et al. |
| 9,833,313 B2 | 12/2017 | Board et al. |
| 9,861,473 B2 | 1/2018 | Lafontaine |
| 9,861,476 B2 | 1/2018 | Salahieh et al. |
| 9,861,477 B2 | 1/2018 | Backus et al. |
| 9,867,698 B2 | 1/2018 | Kovalsky et al. |
| 9,877,830 B2 | 1/2018 | Lim et al. |
| 9,889,029 B2 | 2/2018 | Li et al. |
| 9,895,225 B2 | 2/2018 | Rolando et al. |
| 9,925,045 B2 | 3/2018 | Creaven et al. |
| 10,004,599 B2 | 6/2018 | Rabito et al. |
| 10,117,744 B2 | 11/2018 | Ratz et al. |
| 10,179,044 B2 | 1/2019 | Ratz et al. |
| 10,219,897 B2 | 3/2019 | Essinger et al. |
| 10,350,065 B2 | 7/2019 | Quadri |
| 10,350,066 B2 | 7/2019 | Cooper et al. |
| 10,376,363 B2 | 8/2019 | Quadri et al. |
| 10,555,809 B2 | 2/2020 | Hastings et al. |
| 10,575,951 B2 | 3/2020 | Johnson et al. |
| 10,583,000 B2 | 3/2020 | Ratz et al. |
| 10,639,146 B2 | 5/2020 | Quadri et al. |
| 10,695,177 B2 | 6/2020 | Hariton et al. |

| | | | |
|---|---|---|---|
| 10,758,344 B2 | 9/2020 | Hariton et al. |
| 11,406,499 B2 | 8/2022 | Zhang et al. |
| 11,452,598 B2 | 9/2022 | Essinger et al. |
| 11,672,658 B2 | 6/2023 | Hariton et al. |
| 11,701,225 B2 | 7/2023 | Hammer et al. |
| 11,903,829 B1 | 2/2024 | Ma et al. |
| 2001/0021872 A1 | 9/2001 | Bailey et al. |
| 2002/0032481 A1 | 3/2002 | Gabbay |
| 2002/0045929 A1 | 4/2002 | Diaz |
| 2002/0052644 A1 | 5/2002 | Shaolian et al. |
| 2002/0107565 A1 | 8/2002 | Greenhalgh |
| 2002/0123802 A1 | 9/2002 | Snyders |
| 2002/0173842 A1 | 11/2002 | Buchanan |
| 2003/0050694 A1 | 3/2003 | Yang et al. |
| 2003/0100939 A1 | 5/2003 | Yodfat et al. |
| 2003/0105517 A1 | 6/2003 | White et al. |
| 2003/0114913 A1 | 6/2003 | Spenser et al. |
| 2003/0120333 A1 | 6/2003 | Ouriel et al. |
| 2003/0130729 A1 | 7/2003 | Paniagua et al. |
| 2003/0149477 A1* | 8/2003 | Gabbay ............... A61F 2/2436 |
| | | | 623/2.14 |
| 2003/0149478 A1 | 8/2003 | Figulla et al. |
| 2003/0158597 A1 | 8/2003 | Quiachon et al. |
| 2003/0176914 A1 | 9/2003 | Rabkin et al. |
| 2003/0199971 A1 | 10/2003 | Tower et al. |
| 2003/0212454 A1 | 11/2003 | Scott et al. |
| 2003/0220683 A1 | 11/2003 | Minasian et al. |
| 2004/0039436 A1 | 2/2004 | Spenser et al. |
| 2004/0092858 A1 | 5/2004 | Wilson et al. |
| 2004/0093075 A1 | 5/2004 | Kuehne |
| 2004/0117009 A1 | 6/2004 | Cali et al. |
| 2004/0133263 A1 | 7/2004 | Dusbabek et al. |
| 2004/0133273 A1 | 7/2004 | Cox |
| 2004/0186563 A1 | 9/2004 | Lobbi |
| 2004/0186565 A1 | 9/2004 | Schreck |
| 2004/0210307 A1 | 10/2004 | Khairkhahan |
| 2004/0215325 A1 | 10/2004 | Penn et al. |
| 2004/0225353 A1 | 11/2004 | McGuckin et al. |
| 2004/0236411 A1 | 11/2004 | Sarac et al. |
| 2004/0260389 A1 | 12/2004 | Case et al. |
| 2005/0033398 A1 | 2/2005 | Seguin |
| 2005/0075727 A1 | 4/2005 | Wheatley |
| 2005/0090887 A1 | 4/2005 | Pryor |
| 2005/0096738 A1 | 5/2005 | Cali et al. |
| 2005/0107872 A1 | 5/2005 | Mensah et al. |
| 2005/0137682 A1 | 6/2005 | Justino |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137691 A1 | 6/2005 | Salahieh et al. |
| 2005/0137698 A1 | 6/2005 | Salahieh et al. |
| 2005/0159811 A1 | 7/2005 | Lane |
| 2005/0182486 A1 | 8/2005 | Gabbay |
| 2005/0203614 A1 | 9/2005 | Forster et al. |
| 2005/0203617 A1 | 9/2005 | Forster et al. |
| 2005/0216079 A1 | 9/2005 | MaCoviak |
| 2005/0234546 A1 | 10/2005 | Nugent et al. |
| 2005/0288766 A1 | 12/2005 | Plain et al. |
| 2006/0020327 A1 | 1/2006 | Lashinski et al. |
| 2006/0025857 A1 | 2/2006 | Bergheim et al. |
| 2006/0058872 A1 | 3/2006 | Salahieh et al. |
| 2006/0095115 A1 | 5/2006 | Bladillah et al. |
| 2006/0142837 A1 | 6/2006 | Haverkost et al. |
| 2006/0149350 A1 | 7/2006 | Patel et al. |
| 2006/0161249 A1 | 7/2006 | Realyvasquez et al. |
| 2006/0173537 A1 | 8/2006 | Yang et al. |
| 2006/0195134 A1 | 8/2006 | Crittenden |
| 2006/0195183 A1 | 8/2006 | Navia et al. |
| 2006/0212110 A1 | 9/2006 | Osborne et al. |
| 2006/0229719 A1 | 10/2006 | Marquez et al. |
| 2006/0241745 A1 | 10/2006 | Solem |
| 2006/0259135 A1 | 11/2006 | Navia et al. |
| 2006/0259137 A1 | 11/2006 | Artof et al. |
| 2006/0276874 A1 | 12/2006 | Wilson et al. |
| 2006/0293745 A1 | 12/2006 | Carpentier et al. |
| 2007/0005131 A1 | 1/2007 | Taylor |
| 2007/0010877 A1 | 1/2007 | Salahieh et al. |
| 2007/0027534 A1 | 2/2007 | Bergheim et al. |
| 2007/0043435 A1 | 2/2007 | Seguin et al. |

(56) References Cited

U.S. PATENT DOCUMENTS

| | | |
|---|---|---|
| 2007/0050021 A1 | 3/2007 | Johnson |
| 2007/0066863 A1 | 3/2007 | Rafiee et al. |
| 2007/0088431 A1 | 4/2007 | Bourang et al. |
| 2007/0100432 A1 | 5/2007 | Case et al. |
| 2007/0100439 A1 | 5/2007 | Cangialosi et al. |
| 2007/0112422 A1 | 5/2007 | Dehdashtian |
| 2007/0129794 A1 | 6/2007 | Realyvasquez |
| 2007/0142906 A1 | 6/2007 | Figulla et al. |
| 2007/0156224 A1 | 7/2007 | Cioanta et al. |
| 2007/0162107 A1 | 7/2007 | Haug et al. |
| 2007/0203503 A1 | 8/2007 | Salahieh et al. |
| 2007/0203575 A1 | 8/2007 | Forster et al. |
| 2007/0213813 A1 | 9/2007 | Von Segesser et al. |
| 2007/0255394 A1 | 11/2007 | Ryan |
| 2007/0270943 A1 | 11/2007 | Solem et al. |
| 2008/0021546 A1 | 1/2008 | Patz et al. |
| 2008/0065011 A1 | 3/2008 | Marchand et al. |
| 2008/0071361 A1 | 3/2008 | Tuval et al. |
| 2008/0071362 A1 | 3/2008 | Tuval et al. |
| 2008/0071363 A1 | 3/2008 | Tuval et al. |
| 2008/0071366 A1 | 3/2008 | Tuval et al. |
| 2008/0071368 A1 | 3/2008 | Tuval et al. |
| 2008/0071369 A1 | 3/2008 | Tuval et al. |
| 2008/0082164 A1 | 4/2008 | Friedman |
| 2008/0082165 A1 | 4/2008 | Wilson et al. |
| 2008/0082166 A1 | 4/2008 | Styrc et al. |
| 2008/0097581 A1 | 4/2008 | Shanley |
| 2008/0114442 A1 | 5/2008 | Mitchell et al. |
| 2008/0125853 A1 | 5/2008 | Bailey et al. |
| 2008/0147179 A1 | 6/2008 | Cai et al. |
| 2008/0147183 A1 | 6/2008 | Styrc |
| 2008/0154355 A1 | 6/2008 | Benichou et al. |
| 2008/0161910 A1 | 7/2008 | Revuelta et al. |
| 2008/0177381 A1 | 7/2008 | Navia et al. |
| 2008/0183273 A1 | 7/2008 | Mesana et al. |
| 2008/0208328 A1 | 8/2008 | Antocci et al. |
| 2008/0208332 A1 | 8/2008 | Lamphere et al. |
| 2008/0221672 A1 | 9/2008 | Lamphere et al. |
| 2008/0228254 A1 | 9/2008 | Ryan |
| 2008/0255660 A1 | 10/2008 | Guyenot et al. |
| 2008/0255661 A1 | 10/2008 | Straubinger et al. |
| 2008/0281411 A1 | 11/2008 | Berreklouw |
| 2009/0005863 A1 | 1/2009 | Goetz et al. |
| 2009/0054968 A1 | 2/2009 | Bonhoeffer et al. |
| 2009/0054974 A1 | 2/2009 | McGuckin et al. |
| 2009/0076598 A1 | 3/2009 | Salahieh et al. |
| 2009/0112309 A1 | 4/2009 | Jaramillo et al. |
| 2009/0138079 A1 | 5/2009 | Tuval et al. |
| 2009/0157175 A1 | 6/2009 | Benichou |
| 2009/0164005 A1 | 6/2009 | Dove et al. |
| 2009/0171432 A1 | 7/2009 | Von Segesser et al. |
| 2009/0171447 A1 | 7/2009 | Von Segesser et al. |
| 2009/0171456 A1 | 7/2009 | Kveen et al. |
| 2009/0182413 A1 | 7/2009 | Burkart et al. |
| 2009/0188964 A1 | 7/2009 | Orlov |
| 2009/0216310 A1 | 8/2009 | Straubinger et al. |
| 2009/0216313 A1 | 8/2009 | Straubinger et al. |
| 2009/0216322 A1 | 8/2009 | Le et al. |
| 2009/0222076 A1 | 9/2009 | Figulla et al. |
| 2009/0234443 A1 | 9/2009 | Ottma et al. |
| 2009/0240320 A1 | 9/2009 | Tuval et al. |
| 2009/0270972 A1 | 10/2009 | Lane |
| 2009/0276027 A1 | 11/2009 | Glynn |
| 2009/0276040 A1 | 11/2009 | Rowe et al. |
| 2009/0281618 A1 | 11/2009 | Hill et al. |
| 2009/0281619 A1 | 11/2009 | Le et al. |
| 2009/0287296 A1 | 11/2009 | Manasse |
| 2009/0287299 A1 | 11/2009 | Tabor et al. |
| 2009/0292350 A1 | 11/2009 | Eberhardt et al. |
| 2009/0306768 A1 | 12/2009 | Quadri |
| 2009/0319037 A1 | 12/2009 | Rowe et al. |
| 2010/0016958 A1 | 1/2010 | St. Goar et al. |
| 2010/0024818 A1 | 2/2010 | Stenzler et al. |
| 2010/0049313 A1 | 2/2010 | Alon et al. |
| 2010/0069852 A1 | 3/2010 | Kelley |
| 2010/0114305 A1 | 5/2010 | Kang et al. |
| 2010/0131054 A1 | 5/2010 | Tuval et al. |
| 2010/0137979 A1 | 6/2010 | Tuval et al. |
| 2010/0145438 A1 | 6/2010 | Barone |
| 2010/0174362 A1 | 7/2010 | Straubinger et al. |
| 2010/0191326 A1 | 7/2010 | Alkhatib |
| 2010/0204781 A1 | 8/2010 | Alkhatib |
| 2010/0217382 A1 | 8/2010 | Chau et al. |
| 2010/0249894 A1 | 9/2010 | Oba et al. |
| 2010/0249911 A1 | 9/2010 | Alkhatib |
| 2010/0256723 A1 | 10/2010 | Murray |
| 2010/0262231 A1 | 10/2010 | Tuval et al. |
| 2010/0305685 A1 | 12/2010 | Millwee et al. |
| 2010/0312333 A1 | 12/2010 | Navia et al. |
| 2011/0015616 A1 | 1/2011 | Straubinger et al. |
| 2011/0015729 A1 | 1/2011 | Jimenez et al. |
| 2011/0029072 A1* | 2/2011 | Gabbay ................. A61F 2/2418 623/2.37 |
| 2011/0137397 A1 | 6/2011 | Chau et al. |
| 2011/0178597 A9 | 7/2011 | Navia et al. |
| 2011/0208290 A1 | 8/2011 | Straubinger et al. |
| 2011/0208297 A1 | 8/2011 | Tuval et al. |
| 2011/0208298 A1 | 8/2011 | Tuval et al. |
| 2011/0224785 A1 | 9/2011 | Hacohen |
| 2011/0238159 A1 | 9/2011 | Guyenot et al. |
| 2011/0264196 A1 | 10/2011 | Savage et al. |
| 2011/0264198 A1 | 10/2011 | Murray et al. |
| 2011/0288634 A1 | 11/2011 | Tuval et al. |
| 2011/0313515 A1 | 12/2011 | Quadri et al. |
| 2011/0319989 A1* | 12/2011 | Lane ..................... A61F 2/2436 623/2.37 |
| 2012/0022639 A1 | 1/2012 | Hacohen et al. |
| 2012/0035722 A1 | 2/2012 | Tuval |
| 2012/0041550 A1 | 2/2012 | Salahieh et al. |
| 2012/0046741 A1 | 2/2012 | Tuval et al. |
| 2012/0046742 A1 | 2/2012 | Tuval et al. |
| 2012/0078360 A1 | 3/2012 | Rafiee |
| 2012/0101570 A1 | 4/2012 | Tuval et al. |
| 2012/0101571 A1 | 4/2012 | Thambar et al. |
| 2012/0101572 A1 | 4/2012 | Kovalsky et al. |
| 2012/0123529 A1 | 5/2012 | Levi et al. |
| 2012/0185039 A1 | 7/2012 | Tuval et al. |
| 2012/0197386 A1 | 8/2012 | Von Segesser et al. |
| 2012/0209374 A1 | 8/2012 | Bonhoeffer et al. |
| 2012/0215303 A1 | 8/2012 | Quadri et al. |
| 2012/0271398 A1 | 10/2012 | Essinger et al. |
| 2012/0283823 A1 | 11/2012 | Bonhoeffer et al. |
| 2012/0290062 A1 | 11/2012 | McNamara et al. |
| 2012/0296418 A1 | 11/2012 | Bonyuet et al. |
| 2012/0310328 A1 | 12/2012 | Olson et al. |
| 2012/0310336 A1 | 12/2012 | Figulla et al. |
| 2013/0006294 A1 | 1/2013 | Kashkarov et al. |
| 2013/0035759 A1 | 2/2013 | Gross et al. |
| 2013/0073035 A1 | 3/2013 | Tuval et al. |
| 2013/0079869 A1 | 3/2013 | Straubinger et al. |
| 2013/0172992 A1 | 7/2013 | Gross et al. |
| 2013/0190861 A1 | 7/2013 | Chau et al. |
| 2013/0190862 A1 | 7/2013 | Pintor et al. |
| 2013/0197622 A1 | 8/2013 | Mitra et al. |
| 2013/0211508 A1 | 8/2013 | Lane et al. |
| 2013/0253635 A1 | 9/2013 | Straubinger et al. |
| 2013/0253642 A1 | 9/2013 | Brecker |
| 2013/0310928 A1 | 11/2013 | Morriss et al. |
| 2013/0331929 A1 | 12/2013 | Mitra et al. |
| 2013/0338766 A1 | 12/2013 | Hastings et al. |
| 2013/0345786 A1 | 12/2013 | Behan |
| 2014/0018912 A1 | 1/2014 | Delaloye et al. |
| 2014/0025163 A1 | 1/2014 | Padala et al. |
| 2014/0039611 A1 | 2/2014 | Lane et al. |
| 2014/0052237 A1 | 2/2014 | Lane et al. |
| 2014/0100651 A1 | 4/2014 | Kheradvar et al. |
| 2014/0163668 A1 | 6/2014 | Rafiee |
| 2014/0172077 A1 | 6/2014 | Bruchman et al. |
| 2014/0172083 A1 | 6/2014 | Bruchman et al. |
| 2014/0194981 A1 | 7/2014 | Menk et al. |
| 2014/0207231 A1 | 7/2014 | Hacohen et al. |
| 2014/0214157 A1 | 7/2014 | Börtlein et al. |
| 2014/0222136 A1 | 8/2014 | Geist et al. |
| 2014/0222139 A1 | 8/2014 | Nguyen et al. |

(56)        References Cited

U.S. PATENT DOCUMENTS

| | | |
|---|---|---|
| 2014/0222142 A1 | 8/2014 | Kovalsky et al. |
| 2014/0222144 A1 | 8/2014 | Eberhardt et al. |
| 2014/0243966 A1 | 8/2014 | Garde et al. |
| 2014/0257467 A1 | 9/2014 | Lane et al. |
| 2014/0277390 A1 | 9/2014 | Ratz et al. |
| 2014/0277403 A1 | 9/2014 | Peter |
| 2014/0277412 A1 | 9/2014 | Börtlein et al. |
| 2014/0277422 A1 | 9/2014 | Ratz et al. |
| 2014/0277426 A1 | 9/2014 | Dakin et al. |
| 2014/0277427 A1 | 9/2014 | Ratz et al. |
| 2014/0296973 A1 | 10/2014 | Bergheim et al. |
| 2014/0296975 A1 | 10/2014 | Tegels et al. |
| 2014/0303719 A1 | 10/2014 | Cox et al. |
| 2014/0309728 A1 | 10/2014 | Dehdashtian et al. |
| 2014/0324160 A1 | 10/2014 | Benichou et al. |
| 2014/0324164 A1 | 10/2014 | Gross et al. |
| 2014/0330368 A1 | 11/2014 | Gloss et al. |
| 2014/0330371 A1 | 11/2014 | Gloss et al. |
| 2014/0330372 A1 | 11/2014 | Weston et al. |
| 2014/0336754 A1 | 11/2014 | Gurskis et al. |
| 2014/0343669 A1 | 11/2014 | Lane et al. |
| 2014/0343670 A1 | 11/2014 | Bakis et al. |
| 2014/0350666 A1 | 11/2014 | Righini |
| 2014/0350668 A1 | 11/2014 | Delaloye et al. |
| 2014/0358223 A1 | 12/2014 | Rafiee et al. |
| 2014/0364939 A1 | 12/2014 | Deshmukh et al. |
| 2014/0364943 A1 | 12/2014 | Conklin |
| 2014/0371842 A1 | 12/2014 | Marquez et al. |
| 2014/0371844 A1 | 12/2014 | Dale et al. |
| 2014/0371847 A1 | 12/2014 | Madrid et al. |
| 2014/0371848 A1 | 12/2014 | Murray et al. |
| 2015/0005863 A1 | 1/2015 | Para |
| 2015/0018944 A1 | 1/2015 | O'Connell et al. |
| 2015/0039083 A1 | 2/2015 | Rafiee |
| 2015/0142100 A1 | 5/2015 | Morriss et al. |
| 2015/0142103 A1 | 5/2015 | Vidlund |
| 2015/0148731 A1 | 5/2015 | Mcnamara et al. |
| 2015/0173897 A1 | 6/2015 | Raanani et al. |
| 2015/0196390 A1 | 7/2015 | Ma et al. |
| 2015/0209141 A1 | 7/2015 | Braido et al. |
| 2015/0272737 A1 | 10/2015 | Dale et al. |
| 2015/0297346 A1 | 10/2015 | Duffy et al. |
| 2015/0335429 A1 | 11/2015 | Morriss et al. |
| 2015/0351903 A1 | 12/2015 | Morriss et al. |
| 2015/0359629 A1 | 12/2015 | Ganesan et al. |
| 2016/0000591 A1 | 1/2016 | Lei et al. |
| 2016/0030169 A1 | 2/2016 | Shahriari |
| 2016/0030170 A1 | 2/2016 | Alkhatib et al. |
| 2016/0030171 A1 | 2/2016 | Quijano et al. |
| 2016/0038280 A1 | 2/2016 | Morriss et al. |
| 2016/0038281 A1 | 2/2016 | Delaloye et al. |
| 2016/0074160 A1 | 3/2016 | Christianson et al. |
| 2016/0106537 A1 | 4/2016 | Christianson et al. |
| 2016/0113765 A1 | 4/2016 | Ganesan et al. |
| 2016/0113768 A1 | 4/2016 | Ganesan et al. |
| 2016/0143732 A1 | 5/2016 | Glimsdale |
| 2016/0158010 A1 | 6/2016 | Lim et al. |
| 2016/0166383 A1 | 6/2016 | Lim et al. |
| 2016/0184097 A1 | 6/2016 | Lim et al. |
| 2016/0199206 A1 | 7/2016 | Lim et al. |
| 2016/0213473 A1 | 7/2016 | Hacohen et al. |
| 2016/0235529 A1 | 8/2016 | Ma et al. |
| 2016/0278923 A1 | 9/2016 | Krans et al. |
| 2016/0279386 A1 | 9/2016 | Dale et al. |
| 2016/0310267 A1 | 10/2016 | Zeng et al. |
| 2017/0042678 A1 | 2/2017 | Ganesan et al. |
| 2017/0079785 A1 | 3/2017 | Li |
| 2017/0128209 A1 | 5/2017 | Morriss et al. |
| 2017/0216023 A1 | 8/2017 | Lane et al. |
| 2017/0216575 A1 | 8/2017 | Asleson et al. |
| 2017/0258614 A1 | 9/2017 | Griffin |
| 2017/0325945 A1 | 11/2017 | Dale et al. |
| 2017/0325954 A1 | 11/2017 | Perszyk |
| 2017/0333186 A1 | 11/2017 | Spargias |
| 2017/0348096 A1 | 12/2017 | Anderson |
| 2017/0367821 A1 | 12/2017 | Landon et al. |
| 2017/0367823 A1 | 12/2017 | Hariton et al. |
| 2018/0014931 A1 | 1/2018 | Morriss et al. |
| 2018/0021129 A1 | 1/2018 | Peterson et al. |
| 2018/0055629 A1 | 3/2018 | Oba et al. |
| 2018/0055636 A1 | 3/2018 | Valencia et al. |
| 2018/0085218 A1 | 3/2018 | Eidenschink |
| 2018/0110534 A1 | 4/2018 | Gavala et al. |
| 2018/0110622 A1 | 4/2018 | Gregg et al. |
| 2018/0116790 A1 | 5/2018 | Ratz et al. |
| 2018/0126119 A1 | 5/2018 | McNiven et al. |
| 2018/0296341 A1 | 10/2018 | Noe et al. |
| 2018/0344457 A1 | 12/2018 | Gross et al. |
| 2018/0344490 A1 | 12/2018 | Fox et al. |
| 2019/0008639 A1 | 1/2019 | Landon et al. |
| 2019/0008640 A1 | 1/2019 | Cooper et al. |
| 2019/0060072 A1 | 2/2019 | Zeng |
| 2019/0262129 A1 | 8/2019 | Cooper et al. |
| 2020/0000579 A1 | 1/2020 | Manash et al. |
| 2020/0108225 A1 | 4/2020 | Jamal et al. |
| 2020/0138572 A1 | 5/2020 | Zhao et al. |
| 2020/0323668 A1 | 10/2020 | Diedering et al. |
| 2020/0345494 A1 | 11/2020 | Srinimukesh et al. |
| 2020/0352718 A1 | 11/2020 | Rowe et al. |
| 2021/0015615 A1 | 1/2021 | Groothuis et al. |
| 2021/0145576 A1 | 5/2021 | Becerra et al. |
| 2021/0228354 A1 | 7/2021 | Rafiee et al. |
| 2021/0259835 A1 | 8/2021 | Tyler, II et al. |
| 2021/0307900 A1 | 10/2021 | Hacohen |
| 2021/0378817 A1 | 12/2021 | Nia et al. |
| 2021/0386544 A1 | 12/2021 | Cooper et al. |
| 2022/0142777 A1 | 5/2022 | Scheinblum et al. |
| 2022/0287836 A1 | 9/2022 | Landon et al. |
| 2022/0346993 A1 | 11/2022 | Srinimukesh et al. |
| 2023/0000624 A1 | 1/2023 | Okabe et al. |
| 2023/0200980 A1 | 6/2023 | Peterson et al. |
| 2023/0218391 A1 | 7/2023 | Dass et al. |
| 2023/0380963 A1 | 11/2023 | Kaufman et al. |
| 2023/0390052 A1 | 12/2023 | Okafor et al. |
| 2023/0404753 A1 | 12/2023 | Luong et al. |
| 2024/0008978 A1 | 1/2024 | Nawalakhe et al. |
| 2024/0091000 A1 | 3/2024 | King et al. |

FOREIGN PATENT DOCUMENTS

| | | |
|---|---|---|
| DE | 19532846 A1 | 3/1997 |
| DE | 19546692 A1 | 6/1997 |
| DE | 19857887 A1 | 7/2000 |
| DE | 19907646 A1 | 8/2000 |
| DE | 10049812 A1 | 4/2002 |
| DE | 10049813 C1 | 4/2002 |
| DE | 10049814 A1 | 4/2002 |
| DE | 10049815 A1 | 4/2002 |
| DE | 10010074 B4 | 4/2005 |
| DE | 102006052564 B3 | 12/2007 |
| EP | 0144167 A2 | 6/1985 |
| EP | 0103546 B1 | 5/1988 |
| EP | 0592410 B1 | 10/1995 |
| EP | 0850607 A1 | 7/1998 |
| EP | 0597967 B1 | 12/1999 |
| EP | 1057460 A1 | 12/2000 |
| EP | 1088529 A2 | 4/2001 |
| EP | 1469797 A1 | 10/2004 |
| EP | 1259194 B1 | 2/2005 |
| EP | 1171059 B1 | 11/2005 |
| EP | 1255510 B1 | 4/2007 |
| EP | 1239901 B1 | 10/2007 |
| EP | 1849440 A1 | 10/2007 |
| EP | 1570809 B1 | 1/2009 |
| EP | 1472996 B1 | 9/2009 |
| EP | 1653888 B1 | 9/2009 |
| EP | 1935377 B1 | 3/2010 |
| EP | 1369098 B1 | 4/2014 |
| EP | 2124826 B1 | 7/2014 |
| EP | 2745805 B1 | 6/2015 |
| EP | 2749254 B1 | 6/2015 |
| EP | 2918249 A2 | 9/2015 |
| EP | 2168536 B1 | 4/2016 |
| EP | 2413842 B1 | 8/2017 |

(56) References Cited

FOREIGN PATENT DOCUMENTS

| EP | 2446915 | B1 | 1/2018 |
| EP | 3057541 | B1 | 1/2018 |
| EP | 3037064 | B1 | 3/2018 |
| EP | 3046511 | B1 | 3/2018 |
| EP | 3142603 | B1 | 3/2018 |
| EP | 3075354 | B1 | 11/2018 |
| EP | 3184083 | B1 | 2/2019 |
| EP | 2918249 | B1 | 4/2020 |
| EP | 3417813 | B1 | 5/2020 |
| EP | 2777616 | B1 | 8/2020 |
| EP | 3139864 | B1 | 11/2020 |
| EP | 2750630 | B1 | 6/2021 |
| EP | 2777617 | B1 | 9/2022 |
| EP | 2948103 | B1 | 12/2022 |
| EP | 2967858 | B1 | 1/2023 |
| EP | 3570779 | B1 | 2/2023 |
| EP | 3294220 | B1 | 12/2023 |
| FR | 2788217 | A1 | 7/2000 |
| GB | 1264471 | A | 2/1972 |
| GB | 1315844 | A | 5/1973 |
| GB | 2056023 | A | 3/1981 |
| GB | 2398245 | A | 8/2004 |
| SU | 1271508 | A1 | 11/1986 |
| WO | 1991016041 | A1 | 10/1991 |
| WO | 1991017720 | A1 | 11/1991 |
| WO | 1992017118 | A1 | 10/1992 |
| WO | 1993001768 | A1 | 2/1993 |
| WO | 1997024080 | A1 | 7/1997 |
| WO | 1998029057 | A1 | 7/1998 |
| WO | 1999033414 | A1 | 7/1999 |
| WO | 1999040964 | A1 | 8/1999 |
| WO | 1999047075 | A1 | 9/1999 |
| WO | 2000018333 | A1 | 4/2000 |
| WO | 2000041652 | A1 | 7/2000 |
| WO | 2000047139 | A1 | 8/2000 |
| WO | 2000061034 | A1 | 10/2000 |
| WO | 2001028459 | A1 | 4/2001 |
| WO | 2001035878 | A2 | 5/2001 |
| WO | 2001049213 | A2 | 7/2001 |
| WO | 2001054624 | A1 | 8/2001 |
| WO | 2001054625 | A1 | 8/2001 |
| WO | 2001062189 | A1 | 8/2001 |
| WO | 2001064137 | A1 | 9/2001 |
| WO | 2001076510 | A2 | 10/2001 |
| WO | 2002036048 | A1 | 5/2002 |
| WO | WO-2002041789 | A2 | 5/2002 |
| WO | 2003047468 | A1 | 6/2003 |
| WO | 2003092554 | A1 | 11/2003 |
| WO | 2004030569 | A2 | 4/2004 |
| WO | 2005011534 | A1 | 2/2005 |
| WO | 2005034812 | A1 | 4/2005 |
| WO | WO-2005062980 | A2 | 7/2005 |
| WO | 2005087140 | A1 | 9/2005 |
| WO | 2005102015 | A2 | 11/2005 |
| WO | 2006014233 | A2 | 2/2006 |
| WO | 2006034008 | A2 | 3/2006 |
| WO | 2006085225 | A1 | 8/2006 |
| WO | 2006108090 | A2 | 10/2006 |
| WO | 2006111391 | A1 | 10/2006 |
| WO | 2006138173 | A2 | 12/2006 |
| WO | 2007025028 | A1 | 3/2007 |
| WO | 2008005405 | A2 | 1/2008 |
| WO | 2008035337 | A2 | 3/2008 |
| WO | 2008125153 | A1 | 10/2008 |
| WO | 2008147964 | A1 | 12/2008 |
| WO | 2008150529 | A1 | 12/2008 |
| WO | 2009024859 | A2 | 2/2009 |
| WO | 2009026563 | A2 | 2/2009 |
| WO | WO-2009042196 | A2 * | 4/2009 | .......... A61F 2/2403 |
| WO | 2009091509 | A1 | 7/2009 |
| WO | 2009094500 | A1 | 7/2009 |
| WO | 2010005524 | A2 | 1/2010 |
| WO | 2010008549 | A1 | 1/2010 |
| WO | 2010121076 | A2 | 10/2010 |
| WO | 2011002996 | A2 | 1/2011 |
| WO | 2011081997 | A1 | 7/2011 |
| WO | 2012032187 | A1 | 3/2012 |
| WO | 2012095455 | A2 | 7/2012 |
| WO | 2013028387 | A2 | 2/2013 |
| WO | 2013106585 | A1 | 7/2013 |
| WO | 2014018432 | A2 | 1/2014 |
| WO | 2014079291 | A1 | 5/2014 |
| WO | 2014145338 | A1 | 9/2014 |
| WO | 2014149865 | A1 | 9/2014 |
| WO | 2014163706 | A1 | 10/2014 |
| WO | WO-2014164364 | A1 * | 10/2014 | .......... A61F 2/2409 |
| WO | 2014194178 | A1 | 12/2014 |
| WO | 2015057407 | A1 | 4/2015 |
| WO | 2015077274 | A1 | 5/2015 |
| WO | 2016016899 | A1 | 2/2016 |
| WO | 2017035487 | A1 | 3/2017 |
| WO | 2018213209 | A1 | 11/2018 |
| WO | 2022002054 | A1 | 1/2022 |
| WO | 2023006048 | A1 | 2/2023 |
| WO | 2023076103 | A1 | 5/2023 |
| WO | 2023081236 | A1 | 5/2023 |
| WO | 2023091769 | A1 | 5/2023 |
| WO | 2023096804 | A1 | 6/2023 |
| WO | 2023154250 | A1 | 8/2023 |
| WO | 2023196150 | A1 | 10/2023 |
| WO | 2023244454 | A1 | 12/2023 |
| WO | 2023244767 | A1 | 12/2023 |
| WO | 2023250114 | A1 | 12/2023 |
| WO | 2024001789 | A1 | 1/2024 |
| WO | 2024003620 | A1 | 1/2024 |
| WO | 2024007575 | A1 | 1/2024 |
| WO | 2024009540 | A1 | 1/2024 |
| WO | 2024010739 | A1 | 1/2024 |
| WO | 2024030520 | A1 | 2/2024 |

OTHER PUBLICATIONS

Andersen, Henning Rud, "History of Percutaneous Aortic Valve Prosthesis," Herz 34 2009 Nr. 5, Urban&Vogel, pp. 343-346, Skejby University Hospital Department of Cardiology, Aarhus, Denmark.

Dotter, M.D., Charles T., "Transluminal Treatment of Arteriosclerotic Obstruction," University of Oregon's Minthorn Memorial Laboratory for Cardiovascular Research through Radiology, Circulation, vol. XXX, Nov. 1964, pp. 654-670.

Inoue, M.D., Kanji, et al., "Clinical Application of Transvenous Mitral Commissurotomy by a New Balloon Catheter," The Journal of Thoracic and Cardiovascular Surgery 87:394-402, 1984.

Pavcnik, M.D., Ph.D., Dusan, et al. "Development and Initial Experimental Evaluation of a Prosthetic Aortic Valve for Transcatheter Placement," Cardiovascular Radiology 1992; 183:151-154.

Rashkind, M.D., William J., "Historical Aspects of Interventional Cardiology: Past, Present, Future," Texas Heart Institute Journal, Interventional Cardiology, pp. 363-367. 1986.

Rösch, M.D., Josef, "The Birth, Early Years and Future of Interventional Radiology," J Vasc Interv Radiol 2003; 14:841-853.

Ross, F.R.C.S., D.N., "Aortic Valve Surgery," Guy's Hospital, London, pp. 192-197, approximately 1968.

Sabbah, Ph.D., Hani N., et al., "Mechanical Factors in the Degeneration of Porcine Bioprosthetic Valves: An Overview," Journal of Cardiac Surgery, vol. 4, No. 4, pp. 302-309, Dec. 1989; ISSN 0886-0440.

Wheatley, M.D., David J., "Valve Prostheses," Rob&Smith's Operative Surgery, Fourth Edition, pp. 415-424, Butterworths 1986.

Backer, Ole De, Md, et al., "Percutaneous Transcatheter Mitral Valve Replacemen—An Overview of Devices in Preclinical and Early Clinical Evaluation," Contemporary Reviews in Interventional Cardiology, Circ Cardiovasc Interv. 2014;7:400-409.

Bavaria, Joseph E. M.D.: "CardiAQ Valve Technologies: Transcatheter Mitral Valve Implantation," Sep. 21, 2009.

Berreklouw, Eric, PhD, et al., "Sutureless Mitral Valve Replacement With Bioprostheses and Nitinol Attachment Rings: Feasibility In Acute Pig Experiments," The Journal of Thoracic and Cardiovascular Surgery, vol. 142, No. 2, Aug. 2011 in 7 pages.

Boudjemline, Younes, et al., "Steps Toward the Percutaneous Replacement of Atrioventricular Valves," JACC, vol. 46, No. 2, Jul. 19, 2005:360-5.

(56)         References Cited

OTHER PUBLICATIONS

CardiAQ Valve Technologies, "Innovations in Heart Valve Therapy," In3 San Francisco, Jun. 18, 2008, PowerPoint presentation in 19 slides.

Chiam, Paul T.L., et al., "Percutaneous Transcatheter Aortic Valve Implantation: Assessing Results, Judging Outcomes, and Planning Trials," JACC: Cardiovascular Interventions, The American College of Cardiology Foundation, vol. 1, No. 4, Aug. 2008:341-50.

Condado, Jose Antonio, et al., "Percutaneous Treatment of Heart Valves," Rev Esp Cardio. 2006;59(12):1225-31.

Feldman, Ted, Md. "Prospects for Percutaneous Valve Therapies," Circulation 2007; 116:2866-2877.

Fitzgerald, Peter J. M.D., "Tomorrow's Technology: Percutaneous Mitral Valve Replacement, Chordal Shortening, and Beyond," Transcatheter Valve Therapies (TVT) Conference. Seattle, WA.

Fornell, Dave, "Transcatheter Mitral Valve replacement Devices in Development," Diagnostic and Interventional Cardiology, Dec. 30, 2014, p. 3, <http://www.dicardiology.com/article/transcatheter-mitral-valve-replacement-devices-development>.

Grube, E. et al., "Percutaneous aortic valve replacement for severe aortic stenosis in high-risk patients using the second- and current third-generation self-expanding CoreValve prosthesis: device success and 30-day clinical outcome." J Am Coll Cardiol. Jul. 3, 2007;50(1):69-76. Epub Jun. 6, 2007.

Karimi, Houshang, et al., "Percutaneous Valve Therapies," SIS 2007 Yearbook, Chapter 11, pp. 1-11.

Kronemyer, Bob, "CardiAQ Valve Technologies: Percutaneous Mitral Valve Replacement," Start Up—Windhover Review of Emerging Medical Ventures, vol. 14, Issue No. 6, Jun. 2009, pp. 48-49.

Leon, Martin B., et al., "Transcatheter Aortic Valve Replacement in Patients with Critical Aortic Stenosis: Rationale, Device Descriptions, Early Clinical Experiences, and Perspectives," Semin. Thorac. Cardiovasc. Surg. 18:165-174, 2006 in 10 pages.

Lutter, Georg, et al., "Off-Pump Transapical Mitral Valve Replacement," European Journal of Cardio-thoracic Surgery 36 (2009) 124-128.

Ma, Liang, et al., "'Double-Crowned Valved Stents For Off-Pump Mitral Valve Replacement," European Journal of Cardio-thoracic Surgery 28 (2005) 194-199.

Ostrovsky, Gene, "Transcatheter Mitral Valve Implantation Technology from CardiAQ," medGadget, Jan. 15, 2010, available at: http://www.medgadget.com/2010/01/transcatheter_mitral_valve_implantation_technology_from_cardiaq.html.

Preston-Maher, Georgia L., et al., "A Technical Review of Minimally Invasive Mitral Valve Replacements," Cardiovascular Engineering and Technology, vol. 6, No. 2, Jun. 2015, pp. 174-184.

Quadri, Arshad M.D., "Transcatheter Mitral Valve Implantation (TMVI) (An Acute In Vivo Study),". 2010.

Ratz, J. Brent, "LSI EMT Spotlight," May 15, 2009.

Ratz, J. Brent et al., "Any experiences making an expandable stent frame?" Arch-Pub.com, Architecture Forums: Modeling, Multiple forum postings from Feb. 3, 2009 to Feb. 4, 2009, http://www.arch-pub.com.

Ratz, J. Brent, "In3 Company Overview," Jun. 24, 2009.

Spillner, J. et al., "New Sutureless 'Atrial-Mitral-Valve Prosthesis' For Minimally Invasive Mitral Valve Therapy," Textile Research Journal, 2010, in 7 pages.

Sondergaard, Lars, et al., "Transcatheter Mitral Valve Implantation: CardiAQ™," TCT 2013.

Sondergaard, Lars, et al., "Transcatheter Mitral Valve Implantation: CardiAQ™," EuroPCR 2013.

Treede et al.: "Transapical transcatheter aortic valve implantation using the JenaValve™ system: acute and 30-day results of the multicentre CE-mark study." http://ejcts.oxfordjournals.org/content/41/6/e131.long. Apr. 16, 2012.

Taramasso et al.: "New devices for TAVI: technologies and initial clinical experiences" http://www.nature.com/nrcardio/journal/v11/n3/full/nrcardio.2013.221.html?message-global=remove#access. Jan. 21, 2014.

Webb, John G., et al., "Transcatheter Aortic Valve Implantation: The Evolution Of Prostheses, Delivery Systems And Approaches," Archives of Cardiovascular Disease (2012) 105, 153-159.

Wayback Machine, Cleveland Clinic Lerner Research Institute, Transcatheter Mitral Stent/Valve Prosthetic, https://web.archive.org/web/20130831094624/http://mds.clevelandclinic.org/Portfolio.aspx?n=331, indicated as archived on Aug. 31, 2013.

"CardiAQ Valve Technologies, Percutaneous Mitral Valve Replacement, Company Overview," at TVT on Jun. 25, 2009.

BioSpace, "CardiAQ Valve Technologies (CVT) Reports First-In-Human Percutaneous Transfemoral, Transseptal Implantation With Its Second Generation Transcatheter Bioprosthetic Mitral Heart Valve," Jun. 23, 2015, p. 1, http://www.biospace.com/News/cardiaq-valve-technologies-cvt-reports-first- in/382370.

BioSpace, "CardiAQ Valve Technologies (CVT) Reports Cardiovascular Medicine Milestone: First-In-Humannonsurgical Percutaneous Implantation of a Bioprosthetic Mitral Heart Valve," Jun. 14, 2012, p. 1, http://www.biospace.com/News/cardiaq-valve-technologies-cvt-reports/263900.

Neovasc corporate presentation, Oct. 2009, available at http://www.neovasc.com/investors/documents/Neovasc-Corporate-Presentation-Oct. 2009.pdf.

Bavaria, Joseph E. M.D., "CardiAQ Valve Technologies Transcatheter Mitral Valve Implantation", 11 pages, 2009, CardiAQ Valve Technologies, Inc., Irvine, California.

Herrmann, Howard C., M.D., "Advances in Transseptal Transcatheter Mitral Valve Replacement," Cardiovascular Research Foundation, tct, Sep. 21-25, 2018, 10 Pages, San Diego, California.

Mack, Michael M.D., "Antegrade Transcatheter Mitral Valve Implantation: A Short-term Experience in Swine Model", TVT, Sep. 2011, 10 pages, Washington D.C.

Mack, Michael M.D., "Antegrade Transcatheter Mitral Valve Implantation: On-Going Experience in Swine Model," TVT, Sep. 2011, 16 Pages, Washington D.C.

Neale, Todd, "Flushing TAVI Valves With Carbon Dioxide May Protect Against Brain Injury", Conference News, May 16, 2023, 6 Pages, EuroPCR 2023, Paris, France.

Ruiz et al., "Glimpse into the Future New Transcatheter Mitral Valve Treatment, Overview of Novel Transcatheter Valve Technologies," May 25-28, 2010, 14 pages, EuroPCR 2010, Paris France.

Sondergaard, Lars, "CardiAQ TMVR FIH—Generation 2," Cardiovascular Research Foundation, Jun. 2014, 23 pages, TVT, Vancouver, BC.

Transcatheter Aortic Valve Delivery Catheter System Compression Loading System, Medtronic CoreValve™ System, Medtronic Inc, 2014, 61 pages, Santa Ana, California.

Wheatley D.J., "Valve Prostheses," Operative Surgery, 4th edition, 1986, pp. 415-424.

* cited by examiner

FIG. 9
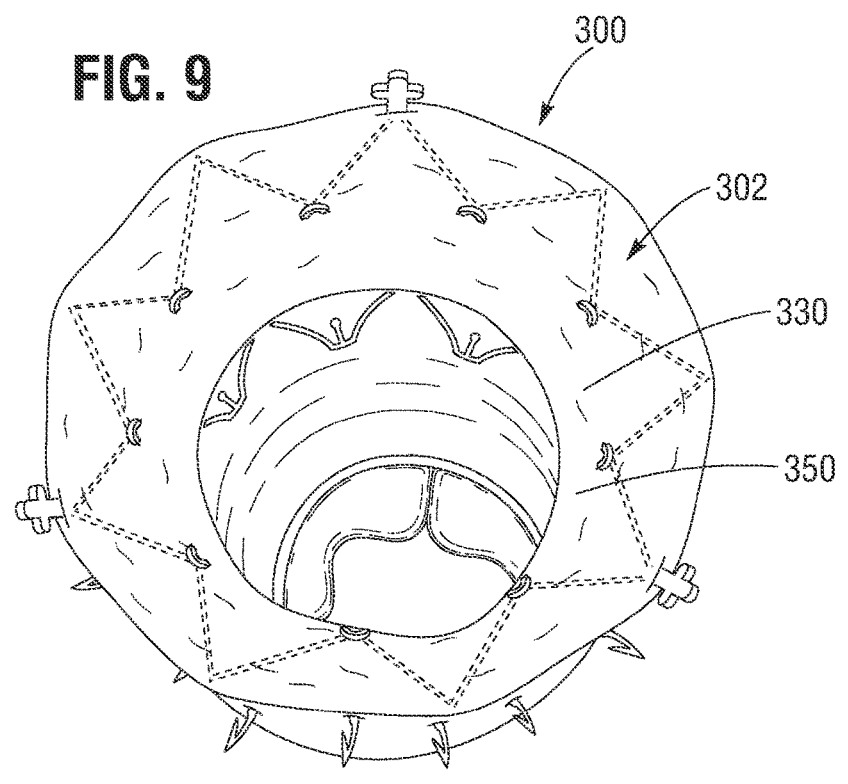
FIG. 10               FIG. 11
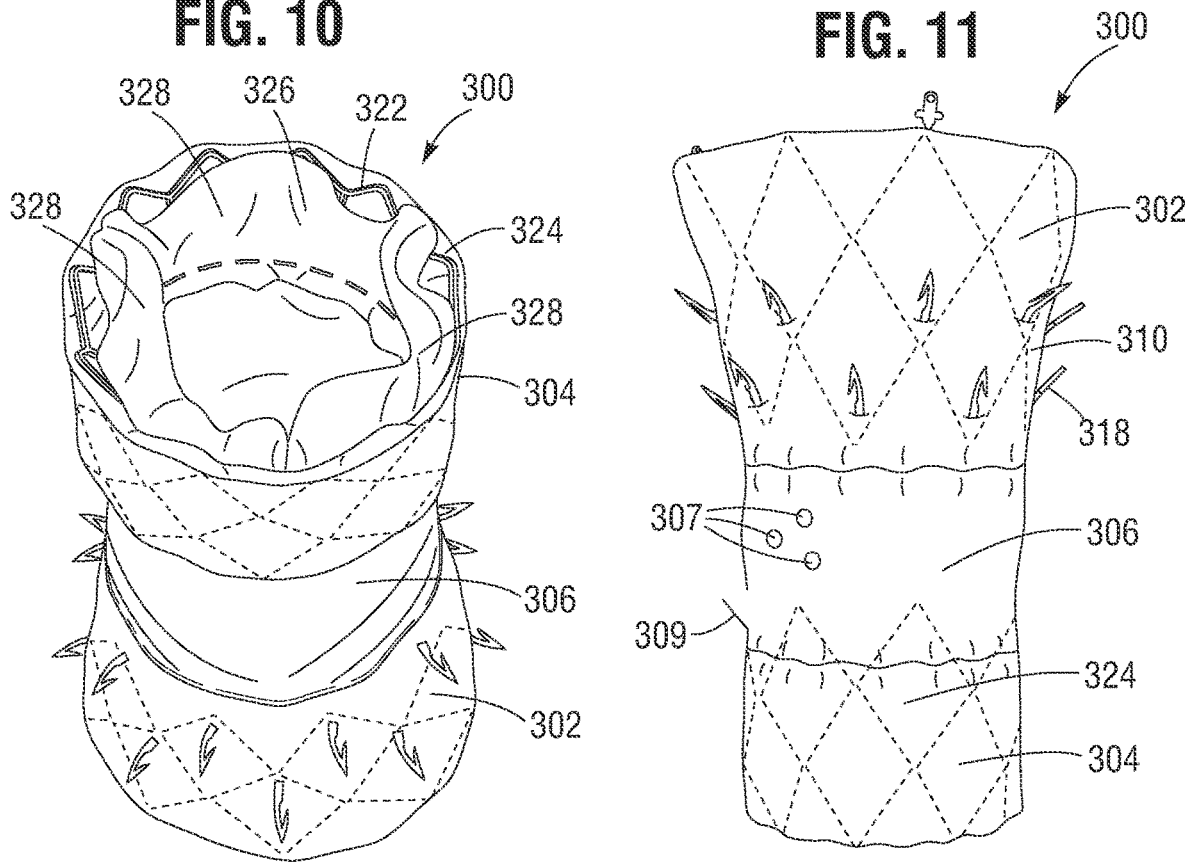

PERCUTANEOUS MITRAL VALVE REPLACEMENT DEVICE

CROSS REFERENCE TO RELATED APPLICATIONS

This application is a continuation of U.S. patent application Ser. No. 16/597,460, filed on Oct. 9, 2019, which is a divisional of U.S. patent application Ser. No. 15/134,172, filed on Apr. 20, 2016, now U.S. Pat. No. 10,441,416, which claims the benefit of U.S. Provisional Application No. 62/264,224, filed on Dec. 7, 2015, and U.S. Provisional Application No. 62/150,431, filed on Apr. 21, 2015. All of the prior applications are incorporated by reference herein.

FIELD

The present disclosure generally concerns prosthetic heart valves and devices and related methods for implanting such a heart valve.

BACKGROUND

The native heart valves (i.e., the aortic, pulmonary, tricuspid and mitral valves) serve critical functions in assuring the forward flow of an adequate supply of blood through the cardiovascular system. These heart valves can be rendered less effective by congenital malformations, inflammatory processes, infectious conditions, or disease. Such damage to the valves can result in serious cardiovascular compromise or death. For many years the definitive treatment for such disorders was the surgical repair or replacement of the valve during open heart surgery. However, such surgeries are highly invasive and are prone to many complications. Therefore, elderly and frail patients with defective heart valves often went untreated. More recently, transvascular techniques have been developed for introducing and implanting prosthetic devices in a manner that is much less invasive than open heart surgery. Such transvascular techniques have increased in popularity due to their high success rates.

A healthy heart has a generally conical shape that tapers to a lower apex. The heart is four-chambered and comprises the left atrium, right atrium, left ventricle, and right ventricle. The left and right sides of the heart are separated by a wall generally referred to as the septum. The native mitral valve of the human heart connects the left atrium to the left ventricle. The mitral valve has a very different anatomy than other native heart valves. The mitral valve includes an annulus portion, which is an annular portion of the native valve tissue surrounding the mitral valve orifice, and a pair of cusps or leaflets extending downward from the annulus into the left ventricle. The mitral valve annulus can form a "D" shaped, oval, or otherwise out-of-round cross-sectional shape having major and minor axes. The anterior leaflet can be larger than the posterior leaflet, forming a generally "C" shaped boundary between the abutting free edges of the leaflets when they are closed together.

When operating properly, the anterior leaflet and the posterior leaflet function together as a one-way valve to allow blood to flow only from the left atrium to the left ventricle. The left atrium receives oxygenated blood from the pulmonary veins. When the muscles of the left atrium contract and the left ventricle dilates (also referred to as "ventricular diastole" or "diastole"), the oxygenated blood that is collected in the left atrium flows into the left ventricle. When the muscles of the left atrium relax and the muscles of the left ventricle contract (also referred to as "ventricular systole" or "systole"), the increased blood pressure in the left ventricle urges the two leaflets together, thereby closing the one-way mitral valve so that blood cannot flow back to the left atrium and is instead expelled out of the left ventricle through the aortic valve. To prevent the two leaflets from prolapsing under pressure and folding back through the mitral annulus toward the left atrium, a plurality of fibrous cords called chordae tendineae tether the leaflets to papillary muscles in the left ventricle.

Mitral regurgitation occurs when the native mitral valve fails to close properly and blood flows into the left atrium from the left ventricle during the systolic phase of heart contraction. Mitral regurgitation is the most common form of valvular heart disease. Mitral regurgitation has different causes, such as leaflet prolapse, dysfunctional papillary muscles, and/or stretching of the mitral valve annulus resulting from dilation of the left ventricle. Mitral regurgitation at a central portion of the leaflets can be referred to as central jet mitral regurgitation, and mitral regurgitation nearer to one commissure (i.e., the location where the leaflets meet) of the leaflets can be referred to as eccentric jet mitral regurgitation.

In addition to mitral regurgitation, mitral narrowing or stenosis is most frequently the result of rheumatic disease. While this has been virtually eliminated in developed countries, it is still common where living standards are not as high.

Similar to complications of the mitral valve are complications of the aortic valve, which controls the flow of blood from the left ventricle into the aorta. For example, many older patients develop aortic valve stenosis.

One method for treating valvular heart disease includes the use of a prosthetic valve implanted within the native heart valve. These prosthetic valves can be implanted using a variety of techniques, including various transcatheter techniques, in which a prosthetic valve is mounted in a crimped or compressed state on the distal end portion of a delivery catheter. The delivery catheter is then advanced through the patient's vasculature until the prosthetic valve reaches the implantation site. The valve at the catheter tip is then expanded to its functional size at the site of the defective native valve such as by inflating a balloon on which the valve is mounted. Alternatively, a self-expanding prosthetic valve can be retained in a radially compressed state within a sheath of a delivery catheter. After the distal end of the delivery catheter is advanced to the implantation site, the prosthetic valve can be deployed from the sheath, which allows the prosthetic valve to expand to its functional state.

Although prosthetic valves for implantation at the aortic valve are well-developed, catheter-based prosthetic valves are not necessarily applicable to the mitral valve due to the distinct differences between the aortic and mitral valves. For example, the mitral valve has a complex subvalvular apparatus, i.e., chordae tendineae, which is not present in the aortic valve. Additionally, the native mitral valve annulus typically does not provide sufficient structure for anchoring and resisting migration of a prosthetic valve.

In recent years, significant efforts have been made in developing prosthetic valves for implantation at the native mitral valve. However, these prosthetic valves can require very difficult and accurate placement which, in turn, leads to unsuccessful or undesirable placement or long procedural times. These constraints can adversely affect a patient's health both during and after the implantation procedure or even prevent some patients from being able to undergo the procedure all together.

As such, there is a continuing need for improved prosthetic valves, as well as methods for implanting such prosthetic valves.

SUMMARY

Described herein are embodiments of prosthetic heart valves and components thereof that are primarily intended to be implanted at one of the native mitral, aortic, tricuspid, or pulmonary valve regions of a human heart, as well as methods for implanting the same. These prosthetic heart valves can be used to help restore and/or replace the functionality of a defective native heart valve. The prosthetic heart valves can comprise projections which are configured to engage the tissue of the native heart valve leaflets to position and secure the prosthetic heart valve in the native heart valve region.

In one representative embodiment, a prosthetic valve assembly for replacing a native heart valve comprises a radially expandable and compressible support structure, the support structure comprising an annular frame having a lumen extending from an inflow end to an outflow end, the support structure further comprising an annular sealing member extending radially inwardly into the lumen of the frame and having an inner peripheral portion defining an orifice, and a radially expandable and compressible valve component, the valve component comprising an annular frame and a valve structure supported inside of the frame for permitting the flow blood through the valve component in one direction and blocking the flow of blood in the opposite direction, wherein the valve component is configured to expand within the orifice of the sealing member and engage the inner peripheral portion of the sealing member when radially expanded.

In some embodiments, the prosthetic valve assembly further comprises a flexible, tubular connector connected at one end to the support structure and at another end to the valve component, the connector permitting the valve assembly to transition from a first, axially extended configuration wherein the valve component is outside of the support structure and a second, axially contracted configuration wherein the valve component is at least partially within the support structure. In some embodiments, the sealing member comprises a fabric.

In some embodiments, the support structure comprises a plurality of projections secured to the outside of the frame of the support structure, the projections having first ends secured to the frame of the support structure and second ends formed as barbs for engaging and penetrating tissue of the native heart valve. In some embodiments, the frames of the support structure and the valve component are sized such that when the valve component is expanded within the support structure, a radially and axially extending gap is defined between the frames along the entire length of the valve component.

In some embodiments, there are no metal components connecting the frames to each other. In some embodiments, the frames are connected to each other only by fabric.

In some embodiments, the sealing member comprises a first end wall defining a first orifice, a second wall axially spaced from the first end wall and defining a second orifice, and a tubular, inner sleeve extending from the first orifice of the first end wall to the second orifice of the second end wall, and wherein the valve component is configured to be deployed within the inner sleeve. In some embodiments, each of the end walls and the inner sleeve comprises fabric. In some embodiments, the sealing member comprises an outer sleeve extending over the outer surface of the frame of the support structure from the first end wall to the second end wall.

In another representative embodiment, a prosthetic valve assembly for replacing a native heart valve, comprises a radially expandable and compressible support structure, the support structure comprising an annular frame having a lumen extending from an inflow end to an outflow end, an annular sealing member extending radially inwardly into the lumen of the frame and having an inner peripheral portion defining an orifice, and a radially expandable and compressible tubular valve component coupled to the sealing member inside of the support structure, the valve component comprising a plurality of leaflets configured to permit the flow blood through the valve component in one direction and block the flow of blood in the opposite direction, wherein the sealing member comprises a first end wall defining a first orifice, a second wall axially spaced from the first end wall and defining a second orifice, and a tubular, inner sleeve extending from the first orifice of the first end wall to the second orifice of the second end wall, and wherein the valve component is mounted inside of the inner sleeve.

In some embodiments, the valve component comprises an annular frame and the leaflets are mounted inside of frame of the valve component. In some embodiments, the prosthetic valve assembly further comprises a flexible, tubular connector connected at one end to the support structure and at another end to the valve component, the connector permitting the valve assembly to transition from a first, axially extending configuration wherein the valve component is outside of the support structure and a second, axially contracted configuration wherein the valve component is at least partially within the support structure.

In some embodiments, the support structure and the valve component define a radially and axially extending gap between the frame, the support structure, and the valve component along the entire length of the valve component when the support structure and the valve component are expanded.

In some embodiments, there are no metal components connecting the frame of the support structure to the valve component. In some embodiments, the frame of the support structure and the valve component are connected to each other only by fabric.

In another representative embodiment, a prosthetic valve assembly for replacing a native heart valve comprises a radially expandable and compressible support structure, the support structure comprising an annular frame having a lumen extending from an inflow end to an outflow end, a blood-impermeable tubular sleeve disposed inside of the frame of the support structure, the sleeve having a lumen extending from an inflow end to an outflow end, wherein the inflow end of the sleeve is spaced radially inward of the inflow end of the frame of the support structure, and a plurality of leaflets supported inside of the sleeve and configured to permit blood to flow through the valve assembly in one direction and block the flow of blood in the opposite direction.

In some embodiments, the leaflets are stitched to the sleeve. In some embodiments, the leaflets are supported inside of another annular frame that is disposed within the sleeve. In some embodiments, the prosthetic valve assembly further comprises first and second, axially spaced apart, blood-impermeable end walls, the first end wall extending radially inwardly from the frame of the support structure and having an inner peripheral edge defining an orifice and secured to the inflow end of the sleeve, the second end wall extending radially inwardly from the frame of the support structure and having an inner peripheral edge defining an orifice and secured to the outflow end of the sleeve.

The foregoing and other objects, features, and advantages of the invention will become more apparent from the following detailed description, which proceeds with reference to the accompanying figures.

BRIEF DESCRIPTION OF THE DRAWINGS

FIG. 9 is a perspective view of the prosthetic valve assembly of FIG. 8 shown in an axially extended configuration, as viewed from the inflow end of the assembly.

FIG. 10 is a perspective view of the prosthetic valve assembly of FIG. 8 shown in an axially extended configuration, as viewed from the outflow end of the assembly.

FIG. 11 is a side view of the prosthetic valve assembly of FIG. 8 shown in an axially extended configuration.

FIGS. 18-21 show an embodiment of a delivery apparatus in various stages of deploying the prosthetic valve assembly of FIG. 8.

DETAILED DESCRIPTION

Figure 1:
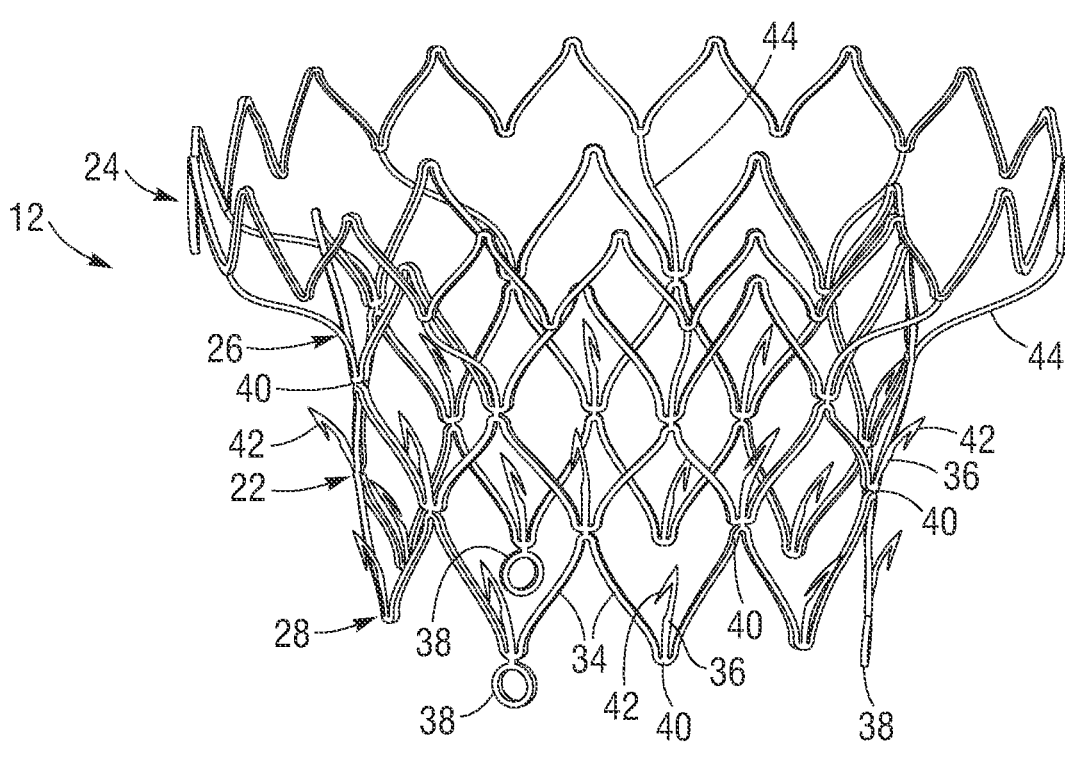
FIG. 1 is a perspective view of a frame of a prosthetic heart valve, according to one embodiment.

For purposes of this description, certain aspects, advantages, and novel features of the embodiments of this disclosure are described herein. The disclosed methods, apparatuses, and systems should not be construed as limiting in any way. Instead, the present disclosure is directed toward all novel and nonobvious features and aspects of the various disclosed embodiments, alone and in various combinations and sub-combinations with one another. The methods, apparatuses, and systems are not limited to any specific aspect or feature or combination thereof, nor do the disclosed embodiments require that any one or more specific advantages be present or problems be solved.

Although the operations of some of the disclosed methods are described in a particular, sequential order for convenient presentation, it should be understood that this manner of description encompasses rearrangement, unless a particular ordering is required by specific language. For example, operations described sequentially may in some cases be rearranged or performed concurrently. Moreover, for the sake of simplicity, the attached figures may not show the various ways in which the disclosed methods can be used in conjunction with other methods.

As used herein, the terms "a", "an" and "at least one" encompass one or more of the specified element. That is, if two of a particular element are present, one of these elements is also present and thus "an" element is present. The terms "a plurality of" and "plural" mean two or more of the specified element.

As used herein, the term "and/or" used between the last two of a list of elements means any one or more of the listed elements. For example, the phrase "A, B, and/or C" means "A," "B," "C," "A and B," "A and C," "B and C" or "A, B and C."

As used herein, the term "coupled" generally means physically coupled or linked and does not exclude the presence of intermediate elements between the coupled items absent specific contrary language.

Described herein are embodiments of prosthetic heart valves and components thereof that are primarily intended to be implanted at one of the native mitral, aortic, tricuspid, or pulmonary valve regions of a human heart, as well as methods for implanting the same. The prosthetic valves can be configured to engage the tissue of the native heart valve leaflets to position and secure the prosthetic heart valve in the native heart valve region. These prosthetic heart valves can be used to help restore and/or replace the functionality of a defective native heart valve.

In particular embodiments, a prosthetic heart valve assembly can be configured to be implanted at or adjacent to the native mitral valve and comprises a frame to which a prosthetic valve structure is attached. The prosthetic heart valve assembly can be delivered and implanted in a minimally invasive manner (e.g., transapical, transventricular, transatrial, transseptal, etc.) within the left ventricle and/or the left atrium.

In particular embodiments, a frame of a prosthetic heart valve assembly comprises a plurality of projections which extend radially outward from the prosthetic heart valve assembly. The projections can be configured to engage and penetrate the tissue of a native heart valve leaflet to secure and/or eliminate or decrease migration of a prosthetic valve within the native valve region.

In particular embodiments, the frame can comprise an atrial flange which can assist in securing a prosthetic heart valve assembly within the native heart valve region and/or eliminate or reduce paravalvular leakage (i.e., leakage around the prosthetic heart valve after implantation).

Figure 2:
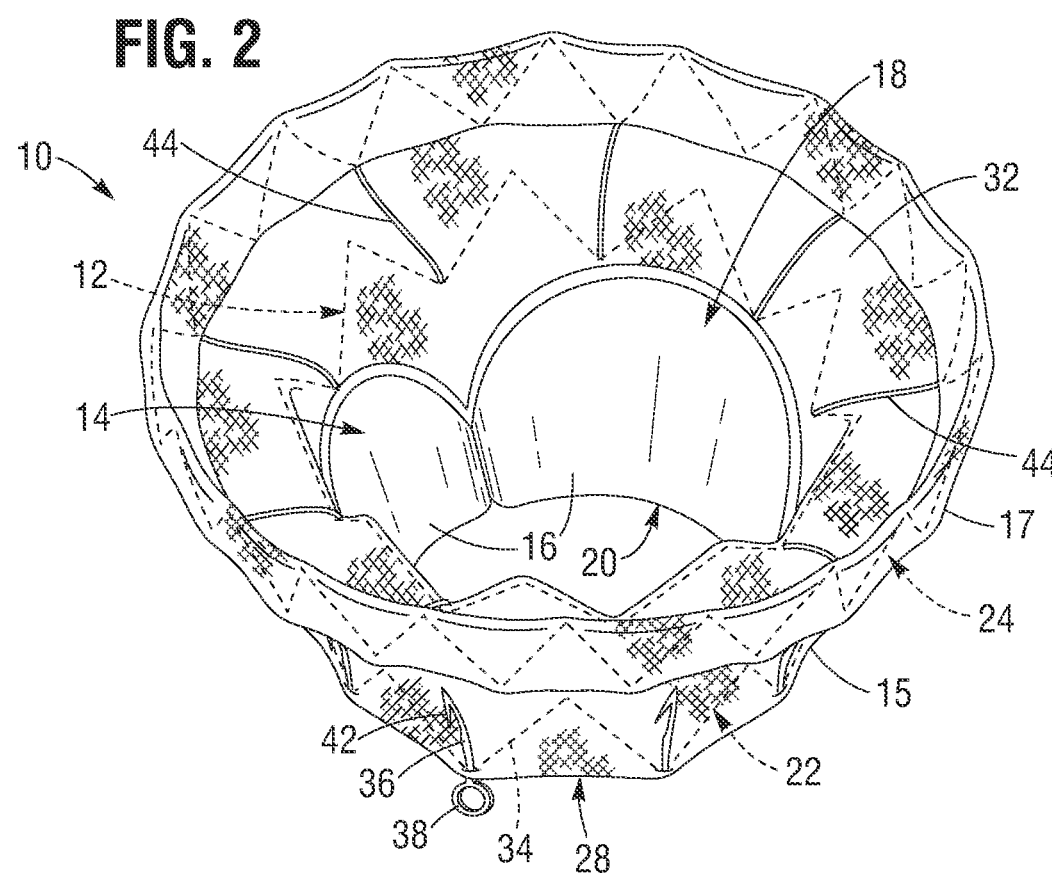
FIG. 2 is a perspective view of an exemplary embodiment of a prosthetic heart valve comprising the frame of FIG. 1.

Referring first to FIG. 2, there is shown an exemplary embodiment of a prosthetic heart valve 10. The prosthetic heart valve 10 can comprise a frame 12 and a valve structure 14 supported by and/or within the frame 12. The valve structure 14 can include a plurality of prosthetic leaflets 16 (three shown in the illustrated embodiment) and/or other components for regulating the flow of blood in one direction through the prosthetic heart valve 10. The valve structure 14 can be oriented within the frame 12 such that an upper end 18 of the valve structure 14 is an inflow end and a lower end 20 of the valve structure 14 is an outflow end. The valve structure 14 can comprise any of various suitable materials, such as natural tissue (e.g., bovine pericardial tissue) or synthetic materials. The prosthetic valve 10 can comprise an annular main body 15 that supports the valve structure 14 and an atrial sealing member 17 extending from the atrial end of the main body 15.

It will be appreciated by those of ordinary skill in the art that the valve structure 14 can be mounted to the frame 12 using suitable techniques and mechanisms. Additional details regarding components and assembly of prosthetic valves (including techniques for mounting leaflets to the frame) are described, for example, in U.S. Patent Application Publication Nos. 2009/0276040 A1, 2010/0217382 A1, and 2014/0222136 A1 and U.S. Pat. No. 8,449,599, which are each incorporated by reference herein.

Referring now to FIG. 1, the frame 12 can comprise a tubular main body 22 and, optionally, an enlarged atrial flange 24 extending both radially outward and axially upward from an atrial end 26 of the main body 22. The frame 12 is desirably covered with a blood-impervious cover 32, as further described below. The atrial flange 24 of the frame supports an upper portion of the cover 32, effectively forming the atrial sealing member 17 of the prosthetic valve 10.

The frame 12 can be configured in this manner, for example, by integrally forming the main body 22 and/or the atrial flange 24 from a single piece of material. This can be accomplished, for example, by laser cutting a tube or forming the frame 12 from a wire mesh. In other embodiments, the frame 12 can be formed from separate pieces of material which are fixedly secured or coupled together. The separate pieces can be fixedly secured together, for example, by welding, soldering, fasteners, etc.

Figure 5:
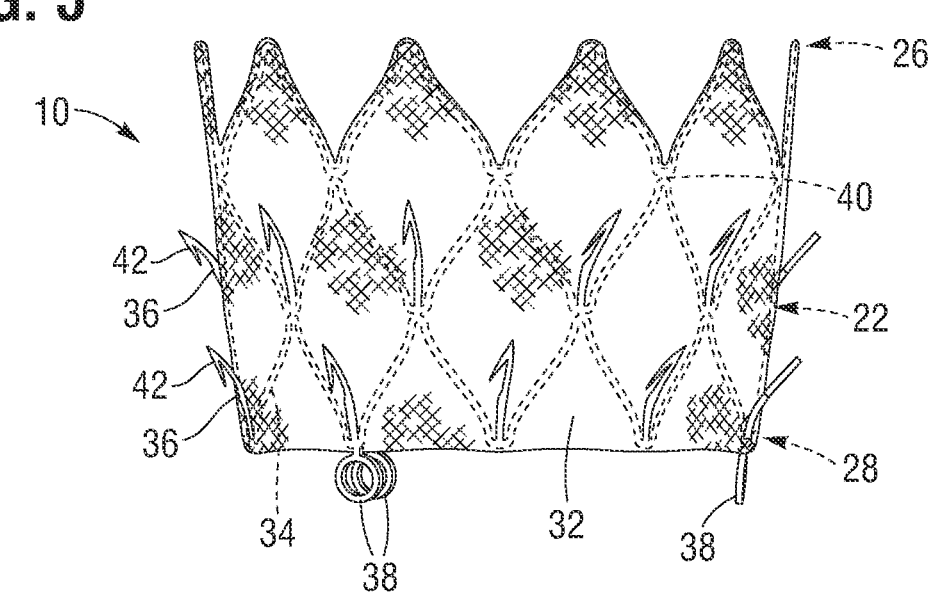
FIG. 5 is a side view of another exemplary embodiment of a prosthetic heart valve.
Figure 6:
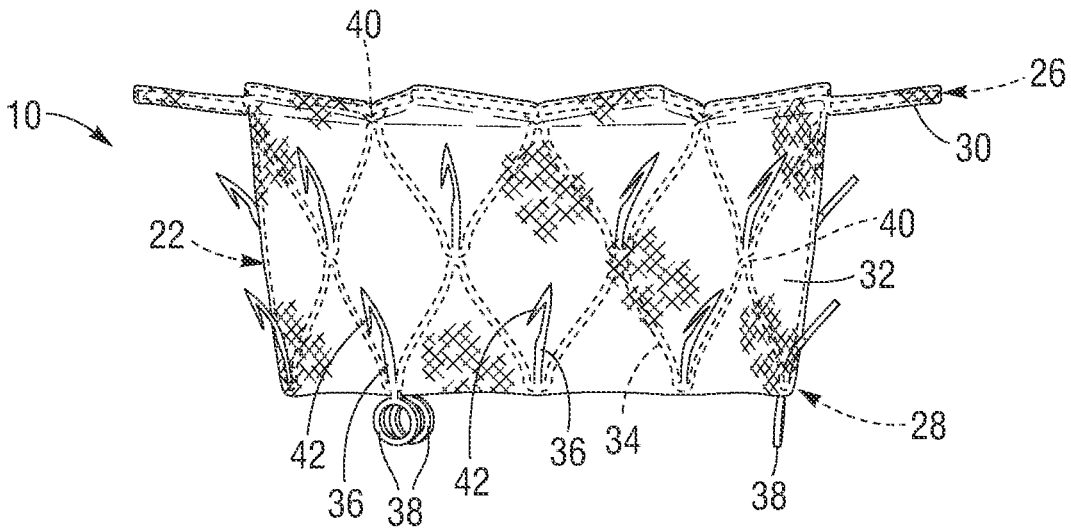
FIG. 6 is a side view of an exemplary prosthetic valve, according to another embodiment.

In an alternative embodiment, the frame 12 can be configured without an atrial flange, as shown in FIG. 5. In another alternative embodiment, the main body 22 can include an atrial flange portion 30 which extends radially outward from the atrial end 26 of the main body 22 and functions similarly to the atrial flange 24, as shown in FIG. 6.

The prosthetic valve 10 can be radially collapsible and expandable between a radially expanded state (FIGS. 1-6) and a radially compressed state (not shown) to enable delivery and implantation at the mitral valve region of the heart (or within another native heart valve). The frame 12 can be formed from a flexible, shape-memory material, such as Nitinol, to enable self-expansion from the radially compressed state to the radially expanded state, as further described below. In alternative embodiments, the frame 12 can be plastically expandable from a radially compressed state to an expanded state by an expansion device, such as an inflatable balloon. Such plastically expanding frames can be formed from stainless steel, chromium alloys, and/or other suitable materials.

In the expanded state, the main body 22 of the frame 12 can form an open-ended tube. The valve structure 14 can be coupled to an inner surface of the frame 12 and can be retained within the lumen formed by the main body 22, as best shown in FIG. 2. The main body 22 can have dimensions substantially similar to or slightly larger than that of the mitral orifice, i.e., the inner surface of the mitral valve annulus 104, such that the main body 22 can engage the inner surface of the mitral valve annulus 104 and native leaflets 110, as further described below.

For example, in the nominal outer diameter of the main body 22 can be about 20 mm to about 55 mm. In some embodiments, the nominal outer diameter of the main body 22 can be about 25 mm to about 40 mm. In one particular embodiment, the nominal outer diameter of the main body 22 is about 29 mm.

The main body 22 of the frame 12 can comprise a plurality of interconnected angled struts 34, a plurality of tissue-engaging projections 36, and at least one positioning member 38 (three in the illustrated embodiment). The projections 36 can be connected to and extend from the struts 34 both radially outward and axially upward toward the atrial end 26 of the main body 22. The projections 36 can be distributed circumferentially and axially on the main body 22 relative to each other. The positioning members 38 can also be connected to the struts 34 and can extend axially downward from a ventricular end 28 of the main body 22.

For example, in the illustrated embodiment, the struts 34 are arranged in circumferentially extending rows connected to each other to form a diamond lattice pattern with the struts 34 intersecting at apices or junctions 40. The projections 36 and positioning members 38 are connected to and each extend from the respective junctions 40 of the struts 34. In alternative embodiments, the struts 34 can be arranged in various other patterns, and the projections 36 and the positioning members 38 can be connected to the struts at various other positions and in various ways.

Figures 3, 4:
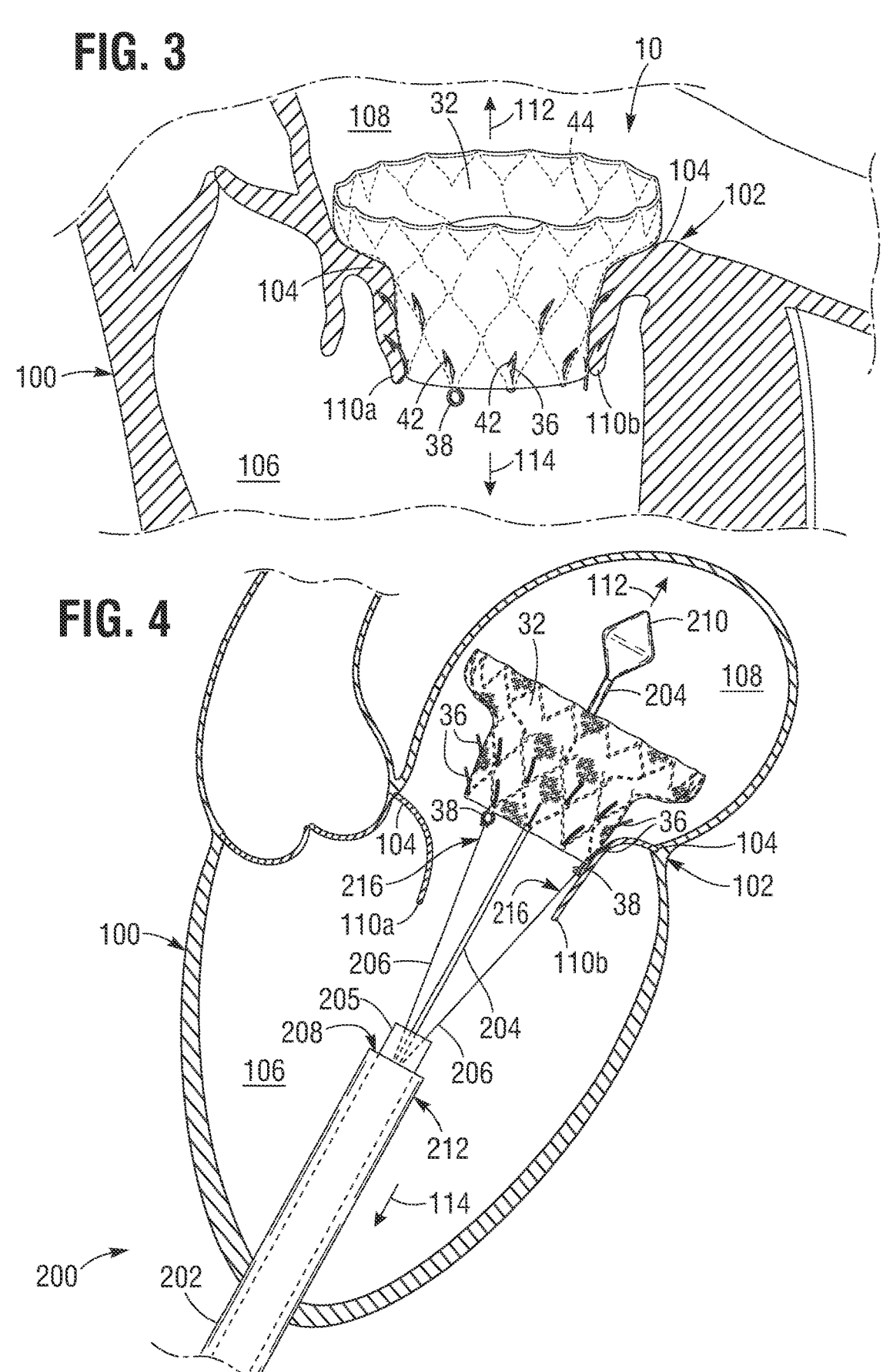
FIG. 3 is a perspective view of the prosthetic heart valve of FIG. 2 positioned within a native mitral valve of a heart, which is shown in partial cross-section.
FIG. 4 is a perspective view of an exemplary embodiment of a delivery apparatus delivering and positioning a prosthetic heart valve in a native mitral valve of a heart, which is shown in partial cross-section.

The projections 36 can be configured to engage or penetrate the tissue of the native heart valve leaflets. For example, as shown in FIG. 3, the projections 36 can penetrate into the native leaflets 110 (i.e., the native anterior leaflet 110a and the native posterior leaflet 110b) as the projections extend radially outward from the main body 22 and axially upward toward the atrial end 26 of the main body 22.

Configuring the projections 36 in this manner can allow the hemodynamic pressure to assist in the initial placement as well as retention of the prosthetic valve 10 within a native heart valve (e.g., a native mitral valve). For example, when the prosthetic valve 10 is placed in the native mitral valve 102, the hemodynamic pressure during the systolic phase of heart contraction causes the prosthetic valve 10 to move slightly upwardly toward the left atrium 108, causing the projections 36 to penetrate the tissue of the native leaflets 110, as best shown in FIG. 3.

Once the prosthetic valve 10 is initially placed within the native mitral valve 102, the axially upward angle of the projections 36 can help maintain the axial positioning of the prosthetic valve 10 relative to the native leaflets 110. This is because the hemodynamic pressure tends to force the prosthetic valve 10 toward the left atrium 108 (i.e. in the direction of shown by arrow 112) during systole, but the angled projections 36 resist this force by urging the projections 36 farther into the native leaflets 110 as the prosthetic valve 10 attempts to move toward the left atrium 108.

In some embodiments, the projections 36 can each include a hook or barb 42 disposed near the distal, free end of the respective projections 36, as best shown in FIG. 1. The barbs 42 can resist the projections 36 from being pulled out of the native leaflets and/or resist the prosthetic valve 10 from moving toward the left ventricle 106 (i.e., in the direction of shown by arrow 114) under the pressure gradient force of the blood flowing from the left atrium into the left ventricle.

In alternative embodiments, the projections 36 can be configured without the barbs, as shown in FIG. 4. Configuring the projections 36 without the barbs can allow the prosthetic valve 10 to be repositioned relatively more easily (i.e., compared to a valve comprising projections with barbs) once the projections 36 initially penetrate the native leaflets 110, as further described below.

The positioning members 38 can be configured to assist in the delivery and/or positioning of the prosthetic valve 10 within a native heart valve. In the illustrated embodiment, the positioning members 38 are loops or eyelets which can be used to releasably connect the prosthetic valve 10 to a delivery apparatus, as further described below.

As shown, the projections 36 and the positioning members 38 can be distributed symmetrically on the main body 22, respectively. However, the projections 36 and the positioning members 38 can be distributed asymmetrically on the main body 22, respectively.

In the expanded state, the atrial flange 24 can be generally frustoconical and extend both radially outward and axially upward from the atrial end 26 of main body 22. The atrial flange 24 be connected to the main body 22 by a plurality of connecting members 44 (nine in the illustrated embodiment). As best shown in FIG. 2, the connecting members 44 can be distributed circumferentially around the atrial flange 24 and can each be connected to a respective junction 40 at the atrial end 26 of the main body 22.

The atrial sealing member 17 can be sized and shaped to contact the atrial side of the mitral valve annulus 104 and tissue of the left atrium 108 when the frame 12 is implanted, as best shown in FIG. 3. The atrial sealing member 17 can also be sized such that when the prosthetic valve 10 is implanted in the native mitral valve 102, the sealing member 17 completely covers the opening between the native leaflets 110, as shown in FIG. 3. The atrial sealing member 17 can comprise a generally circular, oval, or other circumferential shape that generally corresponds to the native geometry of the left atrium 108 and the mitral valve annulus 104. The contact between the atrial sealing member 17 and the tissue of the left atrium 108 and the mitral valve annulus 104 can promote tissue ingrowth with the cover 32, which can improve retention and reduce paravalvular leakage. The atrial sealing member also ensures that all, or substantially all, of the blood passes through the one-way valve as it flows from the left atrium to the left ventricle.

For example, the nominal outer diameter of the atrial sealing member 17 can be about 35 mm to about 70 mm. In some embodiments, the nominal outer diameter of the atrial sealing member 17 can be about 38 mm to about 60 mm. In one particular embodiment, the nominal outer diameter of the atrial sealing member 17 is about 55 mm.

As shown in FIGS. 2-6, the blood-impervious cover 32 can be connected to the inner and/or outer surfaces of the main body 22 and the atrial flange 24 to form at least one layer or envelope covering the openings in the frame 12. It will be appreciated by those of ordinary skill in the art that the cover 32 can be connected to the frame 12 in various ways, such as by sutures.

The cover 32 can form a fluid-occluding and/or flange that can at least partially block the flow of blood through and/or around the frame 12 to reduce paravalvular leakage and can promote tissue ingrowth with the frame 12. The cover 32 can, for example, provide a mounting surface, or scaffold, to which the portions of the valve structure 14, such as the prosthetic leaflets 16, can be secured, as shown in FIG. 2. Configuring the cover 32 in this manner can allow the prosthetic valve 10 to direct blood to flow between the prosthetic leaflets 16.

The cover 32 can comprise a semi-porous fabric that blocks blood flow but can allow for tissue ingrowth. The cover 32 can comprise synthetic materials, such as polyester material or a biocompatible polymer. One example of a polyester material is polyethylene terephthalate (PET). Alternative materials can be used. For example, the layer can comprise biological matter, such as natural tissue, pericardial tissue (e.g., bovine, porcine, or equine pericardium) or other biological tissue.

The prosthetic valve 10 can be delivered to a native heart valve with various delivery apparatuses and delivery techniques (e.g., transventricular, transatrial, transseptal, etc.). For example, FIG. 4 shows the prosthetic valve 10 being delivered to a native mitral valve 102 with an exemplary embodiment of a delivery apparatus 200 using a transventricular technique.

The devices described herein (e.g., the prosthetic valve 10 and the delivery apparatus 200) are described in the context of replacing or repairing a native mitral valve. However, it should be understood that the devices can be used to replace or repair the other native heart valves (i.e., the aortic, pulmonary, and tricuspid).

The delivery apparatus 200 can comprise an introducer 202, a guide wire shaft 204 having a nose cone 210 at a distal end thereof, a deliver catheter 205, and a plurality of positioning cords or tethers 206 (two in the illustrated embodiment). The delivery catheter 205, the guide wire shaft 204, and the positioning cords 206 can extend co-axially through a lumen 208 of the introducer 202. The introducer 202, the delivery catheter 205, the guide wire shaft 204, and the positioning cords 206 can each be axially moveable relative to each other.

The delivery catheter 205 can be used to deliver the prosthetic valve 10 to the native mitral valve in the radially compressed state. In some embodiments, the distal end portion of the delivery catheter 205 can comprise a sheath that is used to retain the prosthetic valve 10 in the radially compressed state (e.g., when the frame 12 is formed from a self-expanding material such as Nitinol). Once the prosthetic valve 10 is disposed in the native mitral valve 102, the sheath of the delivery catheter 204 can be retracted and/or the prosthetic valve 10 can be advanced distally from the sheath, allowing the prosthetic valve 10 to radially self-expand to its functional configuration.

The positioning cords 206 can be formed from flexible material such as a wire or suture. The distal ends 216 of the positioning cords 206 can be releasably connected to the positioning members 38. The positioning cords 206 can be used to adjust the axial positioning of the prosthetic valve 10, as further described below. In some embodiments, the positioning cords 206 can also be used to retract the prosthetic valve 10 back into the delivery catheter after the prosthetic valve has been initially deployed.

When using the delivery apparatus 200 to deliver the prosthetic valve 10 transventricularly, the introducer 202 can be inserted through a surgical opening formed in the patient's chest and in the wall of the left ventricular 106 (e.g., at the bare spot on the lower anterior ventricle wall of heart 100 (FIG. 4)) until the distal end 212 of the introducer 202 resides in the left ventricle 106, as shown in FIG. 4.

The positioning of the delivery apparatus 200 and the prosthetic valve 10 can be confirmed visually using imaging modalities such as fluoroscopy, X-ray, CT or MR imaging. Echocardiography in either 2D or 3D can also be used to help guide the positioning of the delivery apparatus 200 and the prosthetic valve 10.

Although not shown, a standard purse string suture can be used to hold the introducer 202 in place against the heart 100 and prevent blood leakage around the introducer 202, as well as seal the opening in the heart 100 upon removal of the introducer 202. The introducer 202 can include an internal sealing mechanism (e.g., hemostasis seal) to prevent blood leakage through the lumen 208 of introducer 202.

With the prosthetic valve 10 in the radially compressed state within the delivery catheter 205 and releasably attached to the positioning cords 206, the delivery catheter 204 can then be inserted into the patient's heart 100. This is accomplished by advancing the delivery catheter 205 (i.e., in the direction shown by arrow 112) through the lumen 208 of the introducer 202, through the left ventricle 106, and into the native mitral valve 102 and/or left atrium 108. The prosthetic valve 10 can be positioned relative the native mitral valve 102 such that the atrial sealing member 17 is in the left atrium 108, beyond the mitral valve annulus 104. The prosthetic valve 10 can then be radially expanded into its functional configuration, such as by deploying the prosthetic valve 10 from the delivery catheter 205.

Expansion of the prosthetic valve 10 causes the projections 36 to engage the native leaflets 110. In some embodiments, the expansion force of the prosthetic valve 10 in conjunction with the hemodynamic pressure that urges the prosthetic valve 10 upwardly toward the left atrium 108 causes the projections 36 to penetrate the native leaflets 110, thereby securing the prosthetic valve 10 in place. In certain embodiments, the radial expansion of the prosthetic valve is sufficient to cause the projections to penetrate the native leaflets.

Once the projections 36 engage the native leaflets 110 and the prosthetic valve 10 is desirably positioned within the native mitral valve 102, the positioning cords 206 can be detached from the positioning members 38 and retracted through the lumen 208 of the introducer 202, and the delivery catheter 205 can be retracted as well.

If, however, the prosthetic valve 10 is initially undesirably positioned when the projections 36 engage the native leaflets 110, the positioning cords 206 can be used to retract the projections 36 from the native leaflets 110 and to reposition the prosthetic valve 10 as desired. For example, FIG. 4 shows the prosthetic valve 10 undesirably positioned. As shown, the prosthetic valve 10 is, for example, axially positioned too far into the left atrium 108. This positioning can prevent the prosthetic valve 10 from effectively sealing against the native mitral valve 102 because the atrial sealing member 17 (FIG. 1) is not in contact with the mitral valve annulus 104. Also, some of the projections 36 are not engaging the native leaflets 110, which reduces the stability of the prosthetic valve 10 relative to the native mitral valve 102.

The prosthetic valve 10 can be repositioned by retracting the positioning cords 206 axially (i.e., in the direction shown by arrow 114), which in turn causes the prosthetic valve 10 to move axially in the same direction. The axial movement of the prosthetic valve 10 toward the left ventricle 106 causes the projections 36 to withdraw from or disengage the native leaflets 110 and allows the prosthetic valve 10 to be repositioned. Additionally, moving the delivery catheter 205 distally over the positioning cords 206 draws the cords closer together radially and at least partially radially collapses the outflow end of the prosthetic valve to assist with the repositioning of the prosthetic valve.

The prosthetic valve 10 can then be moved axially such that the atrial sealing member 17 contacts the native mitral valve annulus 104, as shown in FIG. 3. As the operator releases tension on the positioning cords 206 and/or retracts the delivery catheter 205 to fully expand the outflow end of the prosthetic valve, the hemodynamic pressure and/or the radial expansion force of the prosthetic valve cause the projections 36 to re-engage and penetrate the native leaflets 110. Once the prosthetic valve is secured to the native leaflets 110, the delivery apparatus 200 can be removed from the patient's body, as described above.

In some embodiments, the prosthetic valve 10 can be retrieved back into the delivery catheter 205 by collapsing the outflow end of the prosthetic valve 10 sufficiently such that the prosthetic valve 10 can be pulled back into the delivery catheter 205 and/or the delivery catheter 205 can advanced distally over the prosthetic valve 10. The fully retrieved valve can then be redeployed or removed from the patient's body, if desired.

Figure 7:
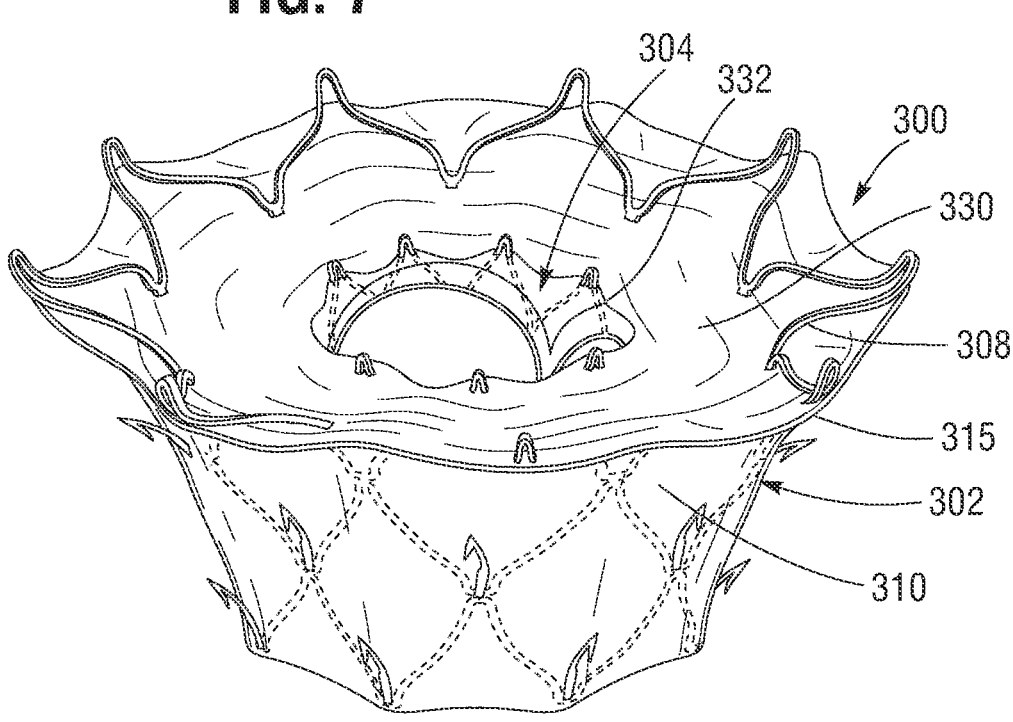
FIG. 7 is a perspective view of a prosthetic valve assembly shown in a deployed configuration, according to another embodiment.
Figure 8:
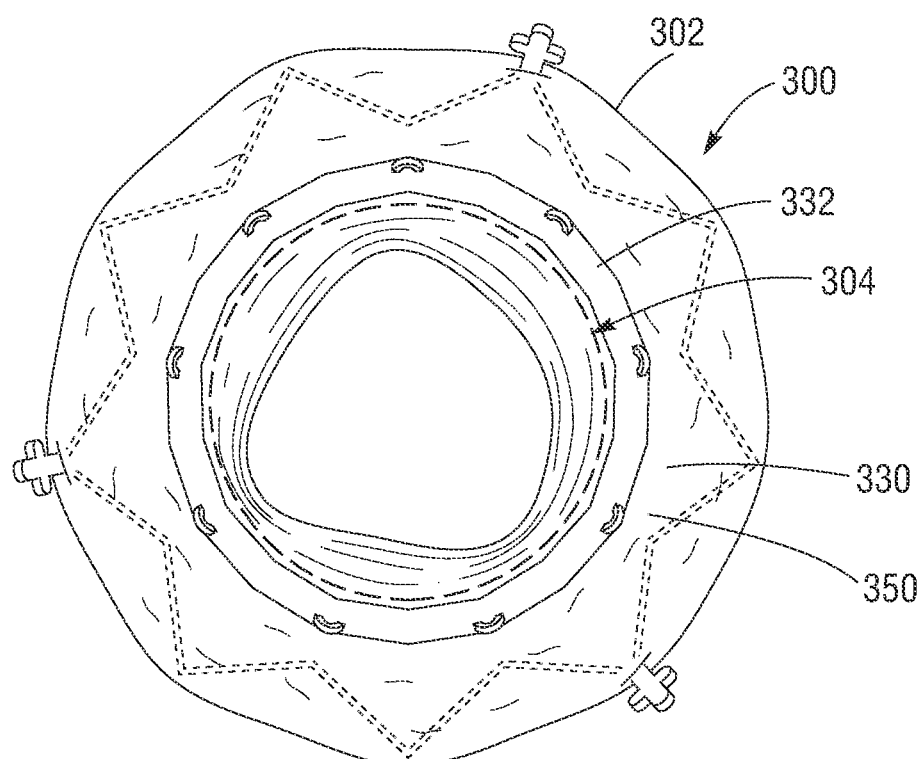
FIG. 8 is a top plan view of a prosthetic valve assembly shown in a deployed configuration, according to another embodiment.

Referring now to FIG. 7, there is shown a prosthetic valve assembly 300, according to another embodiment. The prosthetic valve assembly 300 in the illustrated embodiment comprises an outer support structure 302, a valve component 304, and a tubular flexible connector or sleeve 306 extending between and connecting the support structure 302 to the valve component 304. The prosthetic valve assembly 300 can be transitioned from an axially extended configuration in a delivery state in which the valve component 304 is axially spaced from the support structure 302 (FIGS. 9-11) and an axially contracted configuration in an implanted or deployed state in which the valve component 304 is positioned at least partially within the support structure 302 (FIGS. 7-8), as further described below.

The support structure 302 is configured to be implanted in a native valve annulus (e.g., the native mitral valve annulus) and provide a stable support or platform for supporting the valve component 304. The support structure 302 can be radially compressible and expandable and can comprise a stent or frame 308 and a blood-impermeable cover, liner, or sleeve 310 supported on the outside of the frame 308 (as shown) and/or on the inside of the frame 308. The cover 310 can extend the entire length of the frame 308 and cover the entire outer surface of the frame as shown, or alternatively, extend along less than the entire length of the frame.

The frame 308 can be formed from a shape memory material (e.g., Nitinol) to enable self-expansion of the support structure 302. Alternatively, the frame 308 can be formed from a plastically-expandable material (e.g., stainless steel, chromium alloys) and is configured to be expanded by an expansion device, such as an inflatable balloon.

Figure 12:
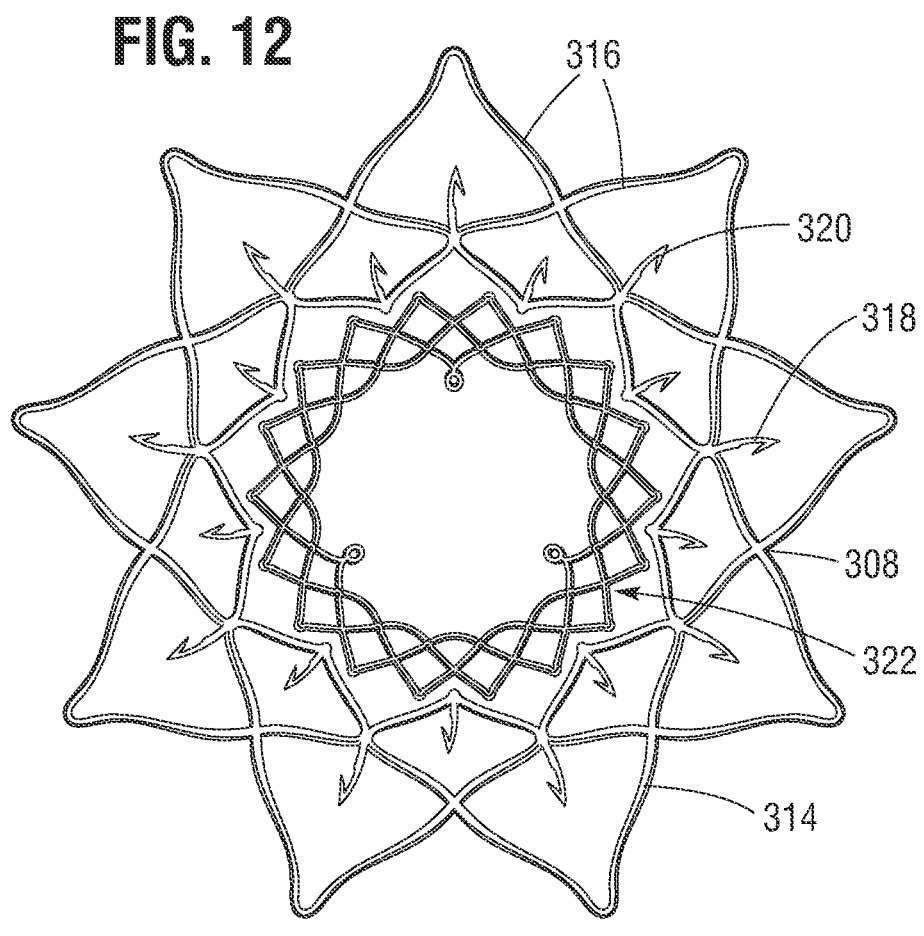
FIG. 12 is a top plan view of the inner and outer frames of the prosthetic valve assembly of FIG. 7.

As best shown in FIG. 12, the frame 308 can comprise a generally tubular main body 312 and an atrial flange 314 extending radially outwardly from an atrial end of the main body 312. The frame 308 can comprise a plurality of interconnected angled struts 316 and a plurality of tissue-engaging projections 318. The atrial flange 314 can be formed by bending the upper row of struts 316 away from the main body 312 and shape-setting the frame in that configuration. The cover 310 can cover the outside of the atrial flange 314, thereby forming an atrial sealing member 315 of the support structure 302. The projections 318 can be distributed circumferentially and/or axially on the outside of the frame and can include barbs 320, similar to projections 36 described above in connection with FIG. 1. Thus, the support structure 302 can be deployed and anchored within the native mitral valve annulus utilizing the projections 318 and/or the atrial flange 314 in the same manner as the prosthetic valve 10.

In particular embodiments, as depicted in FIGS. 8-11, the frame 308 can be formed without an atrial flange that extends radially away from the main body 312 (similar to the frame 12 of FIG. 5). In other embodiments, the frame 308 can have the same configuration as the 12 of FIG. 1.

The valve component 304 can be radially compressible and expandable and can comprise a stent or frame 322 and a blood-impermeable cover or liner 324 supported on the outside of the frame 322 (as shown) and/or on the inside of the frame 322. The frame 322 can be formed from a shape memory material (e.g., Nitinol) to enable self-expansion of the valve component 304. Alternatively, the frame 322 can be formed from a plastically-expandable material (e.g., stainless steel, chromium alloys) and configured to be expanded by an expansion device, such as an inflatable balloon.

A blood-regulating valve structure 326 can be supported inside of the frame 322 for regulating the one-way flow of blood through the valve assembly 300. The valve structure 326 can comprise, for example, one or more flexible leaflets 328.

Figure 13:
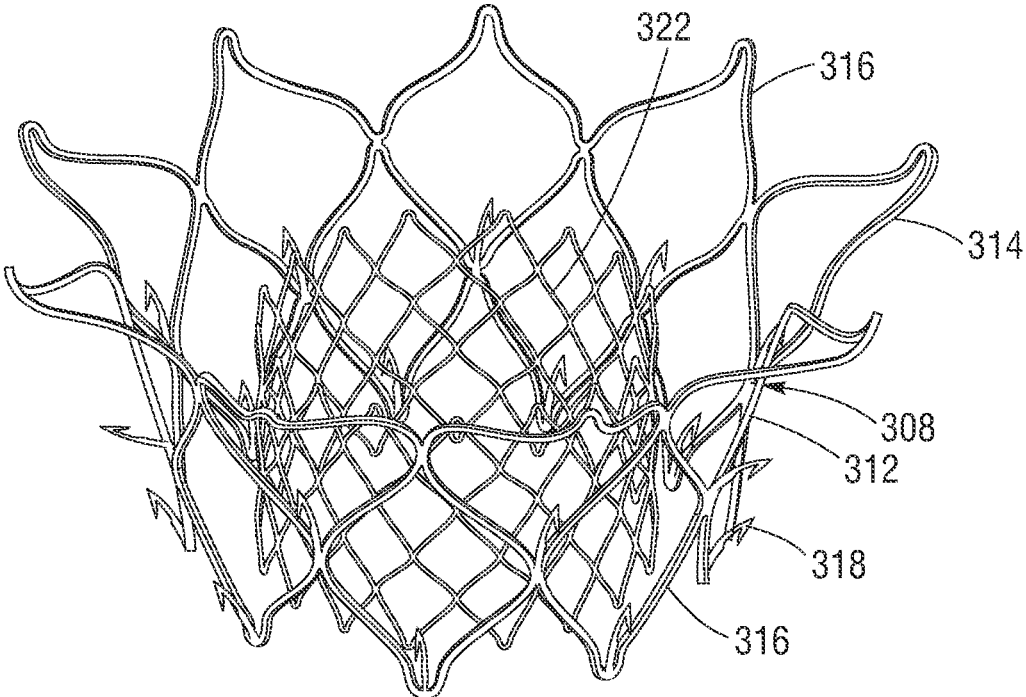
FIG. 13 is a perspective view of the inner and outer frames shown in FIG. 12.
Figure 25:
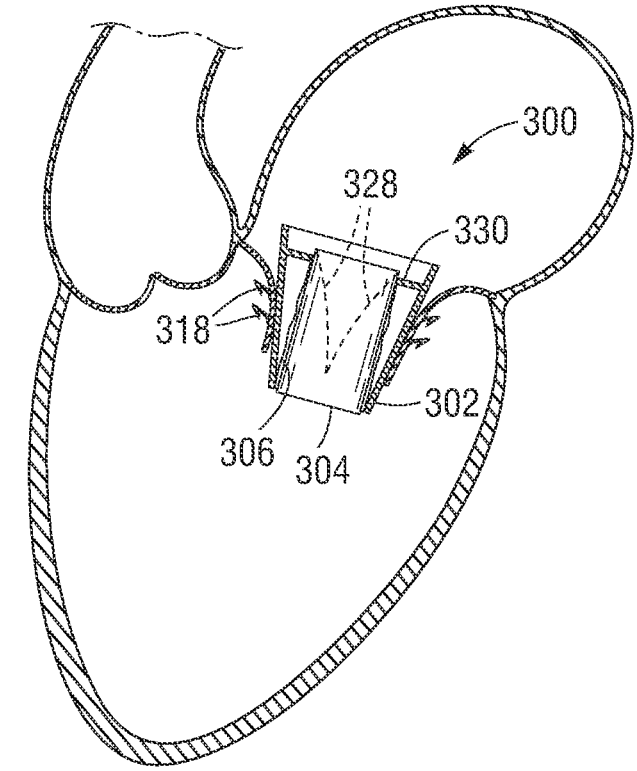

In particular embodiments, the outer diameter of the fully expanded valve component 304 can be smaller than the inner diameter of the fully expanded support structure 302. Thus, when fully deployed (as shown in FIG. 7), the valve component 304 can be said to be "suspended" or "float" within the support structure 302. As best shown in FIGS. 12-13 and 25, for example, the outer diameter of the fully expanded frame 322 of the valve component can be smaller than the inner diameter of the fully expanded frame 308 of the support structure 302 such that there is a radially and axially extending gap between the frames 308, 322 along the entire length of the frame 322. Referring to FIGS. 12 and 13, the frame 308 of the support structure 302 can be referred to as an "outer frame" of the valve assembly 300 while the frame 322 of the valve component 304 can be referred to as an "inner frame" of the valve component 300 due to the position of the frame 322 relative to the frame 308 when the assembly is fully deployed.

In particular embodiments, the frame 308 of the support structure 302 has a diameter measured at the middle of the frame (equidistant from the inflow and outflow ends) of about 35 mm to about 50 mm and the frame 322 of the valve component 304 has a diameter measured at the middle of the frame (equidistant from the inflow and outflow ends) of about 25 mm to about 29 mm.

Referring again to FIGS. 7 and 8, the support structure 302 can include an inner sealing member 330 that extends radially inwardly from the frame 308 at or adjacent the atrial end of the frame 308. The sealing member 330 has an inner peripheral edge that defines an inner orifice 332 that receives and supports an inflow end portion of the valve component 304. In this manner, the sealing member 330 forms an annular end wall having an outer major surface 350 facing in the axial direction that blocks the flow of blood into the annular space between the support structure and the valve component when the valve component is deployed within the support structure.

In particular embodiments, the sealing member 330 functions to secure the valve component 304 in place at least against hemodynamic pressure during the diastolic phase of heart contraction; that is, the sealing member 300 can prevent migration of the valve component 304 toward the left ventricle during diastole. The sealing member 300 can comprise, for example, one or more layers of a blood-impermeable fabric (e.g., PET) and can be an extension of the cover 310. In alternative embodiments, the sealing member 300 can be separately formed from the cover 310 and attached to the frame 308 using suitable techniques (e.g., sutures).

Figure 14:
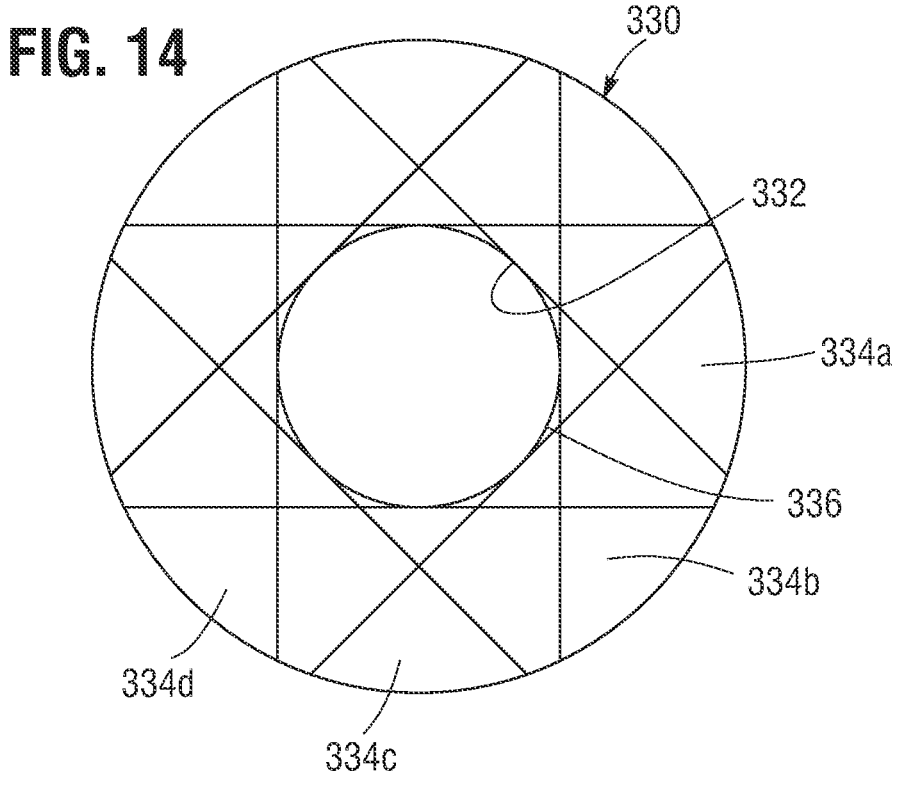
FIGS. 14-17 are top plan views of different embodiments of sealing members that can be incorporated in a prosthetic valve assembly.

FIG. 14 shows the construction of a sealing member 330, according to one embodiment. The sealing member 330 in this embodiment can include a plurality of strips of material 334a, 334b, 334c, 334d (e.g., fabric strips) oriented at different angles relative to each other and at different angular positions relative to the center of the sealing member. The strips 334a-334d may be layered on a toroid shape piece of material (e.g., layer of fabric). The strips 334a-334d render the sealing member much less extensible or stretchable in the radial direction to resist enlargement or dilation of the orifice 332 when the valve component 304 is deployed within the sealing member 330. The sealing member 330 can also include a thin, continuous piece of flexible material 336 circumscribing the orifice 332, such as a suture, chord, or string, that resists enlargement of the orifice 332.

Figure 15:
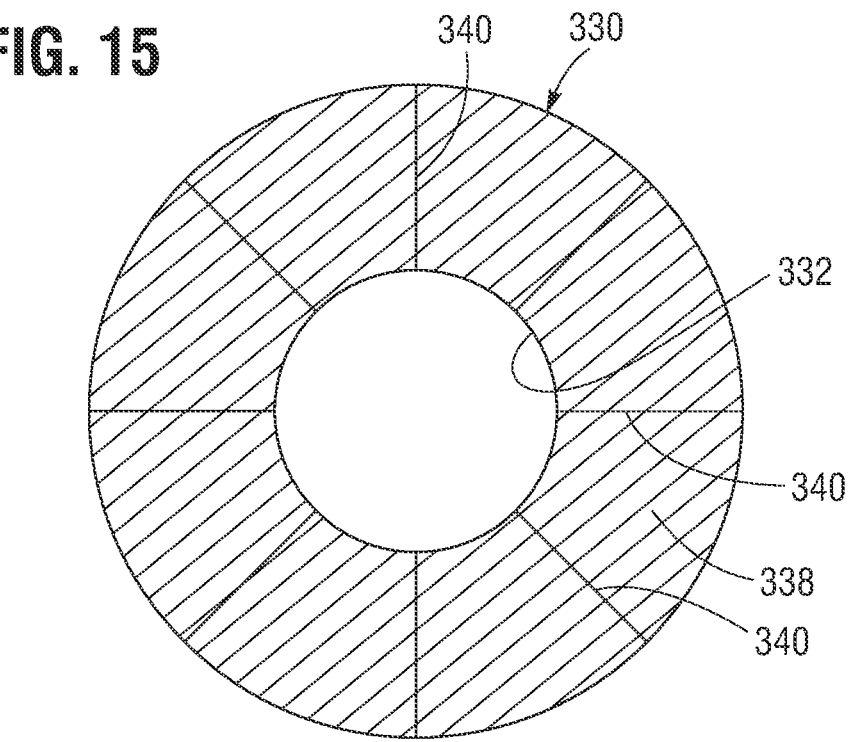

FIG. 15 shows the construction of a sealing member 330, according to another embodiment. The sealing member 330 in this embodiment can comprise one or more stacked layers 338 of a toroid shaped material (e.g., fabric) that is reinforced with a plurality of radially extending struts 340 to resist enlargement of the orifice 332. The struts 340 can comprise, for example, relatively flexible material, such as suture material or a stronger or heavier fabric than that used to form the layer 338. Alternatively, the struts 340 can be formed from thin pieces of a biocompatible polymer or metal (e.g., stainless steel or Nitinol).

Figure 16:
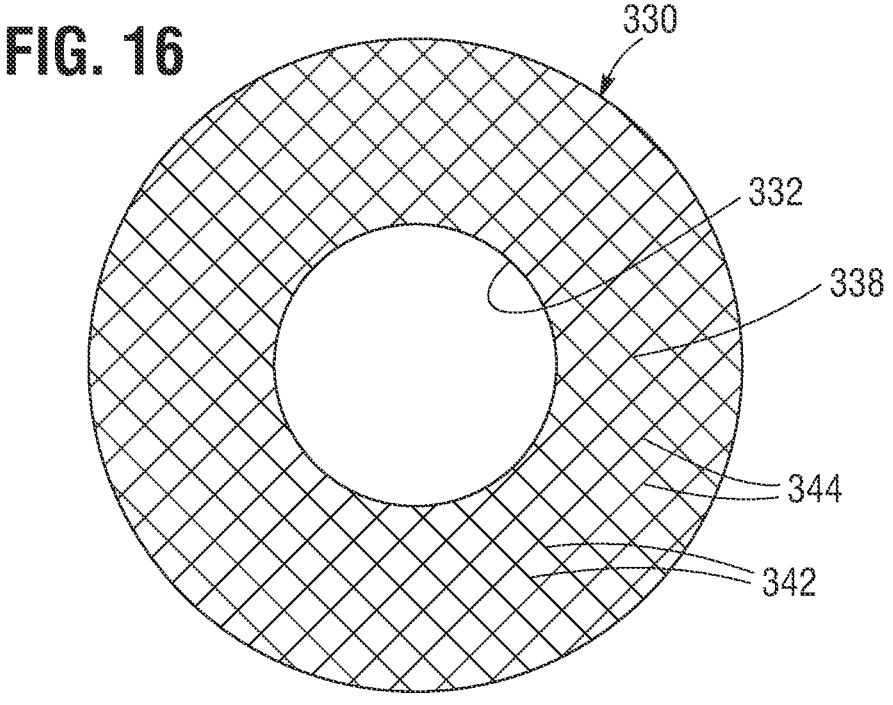

FIG. 16 shows the construction of a sealing member 330, according to another embodiment. The sealing member 330 is this embodiment can comprise two or more stacked, toroid-shaped layers 338 of fabric arranged such that the warp and weft fibers of one layer extend at different angles of the warp and weft fibers from another layer. For example, in FIG. 16, the warp fibers of one layer are depicted as reference number 342 and the warp fibers of another layer are depicted as reference number 344. As shown, the fibers 342 are oriented at 90-degree angles relative to the fibers 344. Orienting the fibers at different angles can increase the ability of the sealing member to resist enlargement of the orifice 332.

Figure 17:
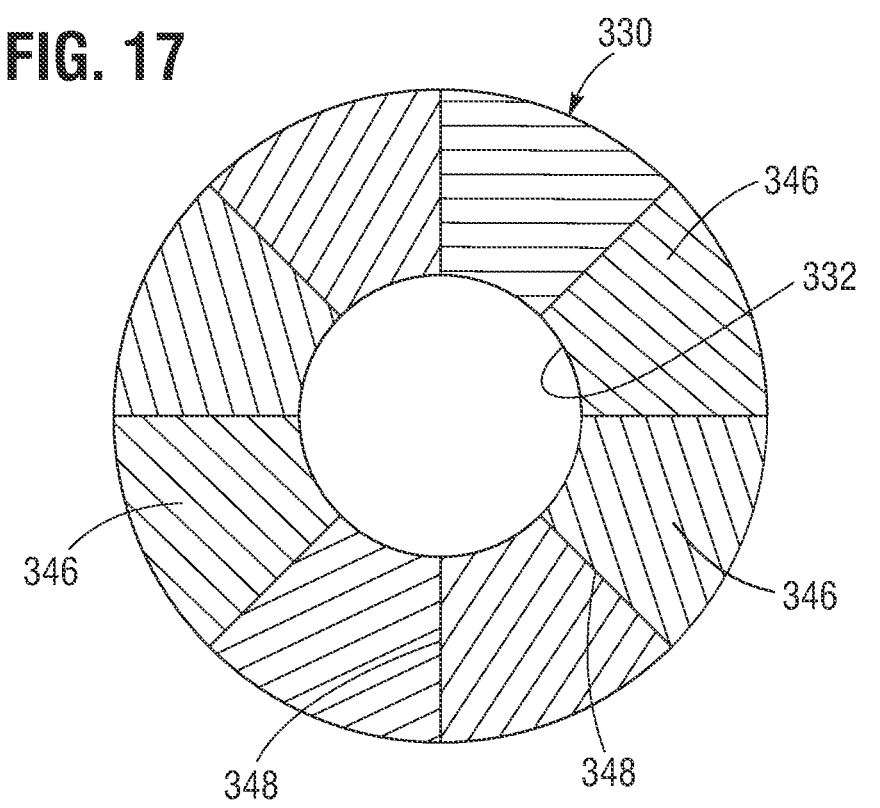

FIG. 17 shows the construction of a sealing member 330, according to another embodiment. The sealing member 330 is this embodiment can comprise a plurality of angular segments of material 346 (e.g., fabric) connected to each other along radially extending seams 348 (e.g., by suturing or stitching). The angular segments 346 can increase the ability of the sealing member to resist enlargement of the orifice 332.

In alternative embodiments, one or more features disclosed in any of sealing members of FIGS. 14-17 can be combined with one or more features disclosed in another one of the sealing members of FIGS. 14-17. For example, a sealing member can comprise the angular segments 346 of FIG. 17 and the toroid shaped layers 338 of FIG. 16.

Referring again to FIGS. 10 and 11, the connecting member 306 can extend from an inflow end of the valve component 304 to an outflow end of the support structure 302. The connecting member 306 can be made of a suitable biocompatible fabric (e.g., PET) or natural tissue. The connecting member 306 can be stitched or otherwise secured to the cover 310 of the support structure 302 and the cover 324 of the valve component 304. Alternatively, a single continuous piece of material can be used to form the cover 310, the cover 324, and the connecting member 306. During deployment of the valve assembly 300, the connecting member 306 allows the valve component 304 to be pushed or pulled to a position inside of the support structure 302, with the connecting member 306 assuming an inverted state inside of the support structure 302, as further described below. Once fully deployed, the connecting member 306 resists migration of the valve component 304 toward the left atrium against hemodynamic pressure during systole.

Referring to FIG. 11, in some embodiments, the connecting member 306 can comprise one or more apertures 307 and/or flaps 309 extending through the connecting member 306. The apertures 307 and/or flaps 309 can be spaced apart and/or distributed on the connecting member 306 in various manners. The apertures 307 and/or flaps 309 can be configured to allow blood to flow from the left atrium, through the support structure 302, through the connecting member 306, and into the left ventricle. In some embodiments, the apertures 307 and/or flaps 309 can be configured to allow the flow of blood in a one direction through connecting member (e.g., from the left atrium to the left ventricle) and to prevent the flow of blood in another direction through the connecting member 306 (e.g., from the left ventricle to the left atrium).

Figure 22:
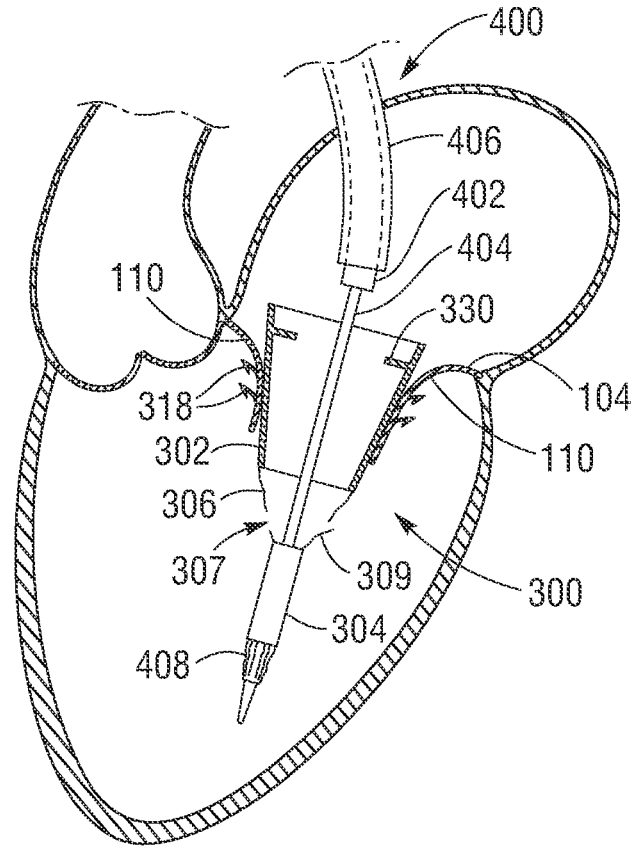
FIGS. 22-25 show the valve assembly of FIG. 8 being implanted in the native mitral valve using the delivery apparatus shown in FIGS. 18-21.

As such, the apertures 307 and/or flaps 309 can allow at least some blood to flow through the valve assembly 300 during the deployment procedure. Referring to FIG. 22, for example, the apertures 307 and/or flaps 309 can allow at least some blood to flow from the left atrium, through the connecting member 306, and into the left ventricle during deployment of the valve assembly 300 when the support structure 302 is expanded and the valve component 304 is not yet expanded. The flaps 309 can be configured to allow blood to flow from the left atrium to the left ventricle via respective openings in the connecting member 306 during diastole and then cover-up and close the respective openings during systole to block retrograde blood from flowing back into the left atrium.

Referring to FIG. 25, for example, the apertures 307 and/or flaps 309 (not shown) can be closed, thus preventing blood from flowing through the apertures 307 and/or flaps 309 during diastole and systole, when the valve structure 304 is positioned inside of the support structure 302 and expanded and the connecting member 306 is inverted. Once the valve structure 304 is expanded, the leaflets 328 of the valve structure 304 can assume the blood-regulating function. Thus, configuring the valve assembly 300 in this manner allows at least some blood-flow through the valve assembly 300 during the deployment procedure.

Allowing blood to flow through the valve assembly 300 during the deployment procedure can advantageously allow a patient's heart to continue to at least partial function during the deployment procedure, thus reducing trauma to the patient. It can also advantageously allow a physician to more easily position the valve assembly 300 because forces acting on the valve assembly 300 caused by hemodynamic pressure are reduced when blood can pass through the valve assembly 300.

Notably, the valve component 304 defines a flow orifice for blood flow from the left atrium to the left ventricle, which flow orifice is not dependent on the size of the support structure 302. As such, the support structure 302 can be sized to fill the native annulus to prevent or at least minimize paravalvular leakage while the valve component 304 can be sized to provide a flow orifice (which is not dependent on the size of the support structure) that more closely mimics the hemodynamics of a healthy native mitral valve. Thus, in certain embodiments, the valve component is undersized relative to the support structure and defines a flow orifice much smaller than the lumen of the support structure. This is particularly advantageous when the patient has a relatively large mitral valve orifice that needs to be filled. In addition, providing a valve component that is undersized relative to the support structure, the size of the prosthetic leaflets 328 can be minimized, which improves overall leaflet function and durability. Another advantage of the valve assembly 300 is that the leaflets 328 can be positioned outside of the support structure 302 during delivery through a patient's vasculature, which minimizes the overall crimp profile of the assembly during delivery.

In addition, in particular embodiments, there are no metal components that interconnect the frame 308 of the support structure to the frame 322 of the valve component. Indeed, in the illustrated embodiment, the flexible sleeve is the only component interconnecting the support structure and the valve component. Minimizing the amount of metal components in the valve assembly helps minimize the overall crimp profile of the valve assembly and improves tracking of the valve assembly through the vasculature of the patient.

Turning now to FIGS. 18-25, a method and apparatus for delivering a valve assembly 300 to the native mitral valve will now be described. FIGS. 18-21 show a delivery apparatus 400, according to one embodiment, configured to implant a valve assembly 300 having a self-expandable support structure 302 and a plastically-expandable valve component 304. The valve assembly 300 is mounted on the delivery apparatus 400 for trans-septal delivery, although other delivery techniques can be used.

The delivery apparatus 400 can comprise a first shaft 402, a second shaft 404 extending co-axially through the first shaft 404, an outer sheath 406 extending co-axially over the first shaft 404, an inflatable balloon 408 mounted on a distal end portion of the second shaft 404, and a nose cone 410 mounted on the distal end portion of the second shaft 404 distal to the balloon 408. The second shaft 404 can have a lumen configured to receive a guidewire. The first shaft 402, the second shaft 404, and the sheath 406 can be axially moveable relative to each other and can extend distally from a handle (not shown) at the proximal end of the delivery apparatus 400. Further details regarding the construction of the delivery apparatus are disclosed in U.S. Publication No. 2013/0030519, which is incorporated herein by reference.

When mounting the valve assembly 300 on the delivery apparatus 400 for insertion into a patient's body, the valve assembly 300 is placed in the axially extended configuration with the valve component 304 outside of and axially spaced from the support structure 302. The valve component 304 is crimped to a radially compressed state onto the balloon 408 and the support structure 302 is crimped and inserted into the sheath 406 to retain the support structure in the radially compressed state. If desired, the sheath 406 also can be advanced over the radially compressed valve component 304 (as shown in FIG. 18) to prevent direct contact between the patient's vasculature and the valve component 304.

As noted above, the delivery apparatus 400 and the valve assembly 300 can be advanced into the heart via a trans-septal route by which the delivery apparatus 400 and the valve assembly 300 are advanced into the right atrium (such as via the inferior or superior vena cava), across the atrial septum, and into the left atrium. The delivery apparatus 400 can then be used to position the support structure 302 within the native mitral valve, after which the sheath 406 is retracted relative to the valve assembly 300 and/or the valve assembly 300 is advanced distally relative to the sheath 406, allowing the support structure 302 to radially expand to its functional size (FIG. 19).

As best shown in FIG. 22, the projections 318 of the support structure 302 can engage and extend through the native leaflets 110 to anchor the support structure in place within the native mitral valve annulus 104. If the support structure has an atrial sealing member 315 (FIG. 7), the sealing member is positioned above the native annulus within the left atrium, similar to the prosthetic valve 10 shown in FIG. 3. Engagement and penetration of the leaflets 110 by the projections 318 can be accomplished by expansion of the support structure 302, hemodynamic pressure, and/or a retraction force applied to the delivery apparatus 400.

Figures 18, 19, 20:
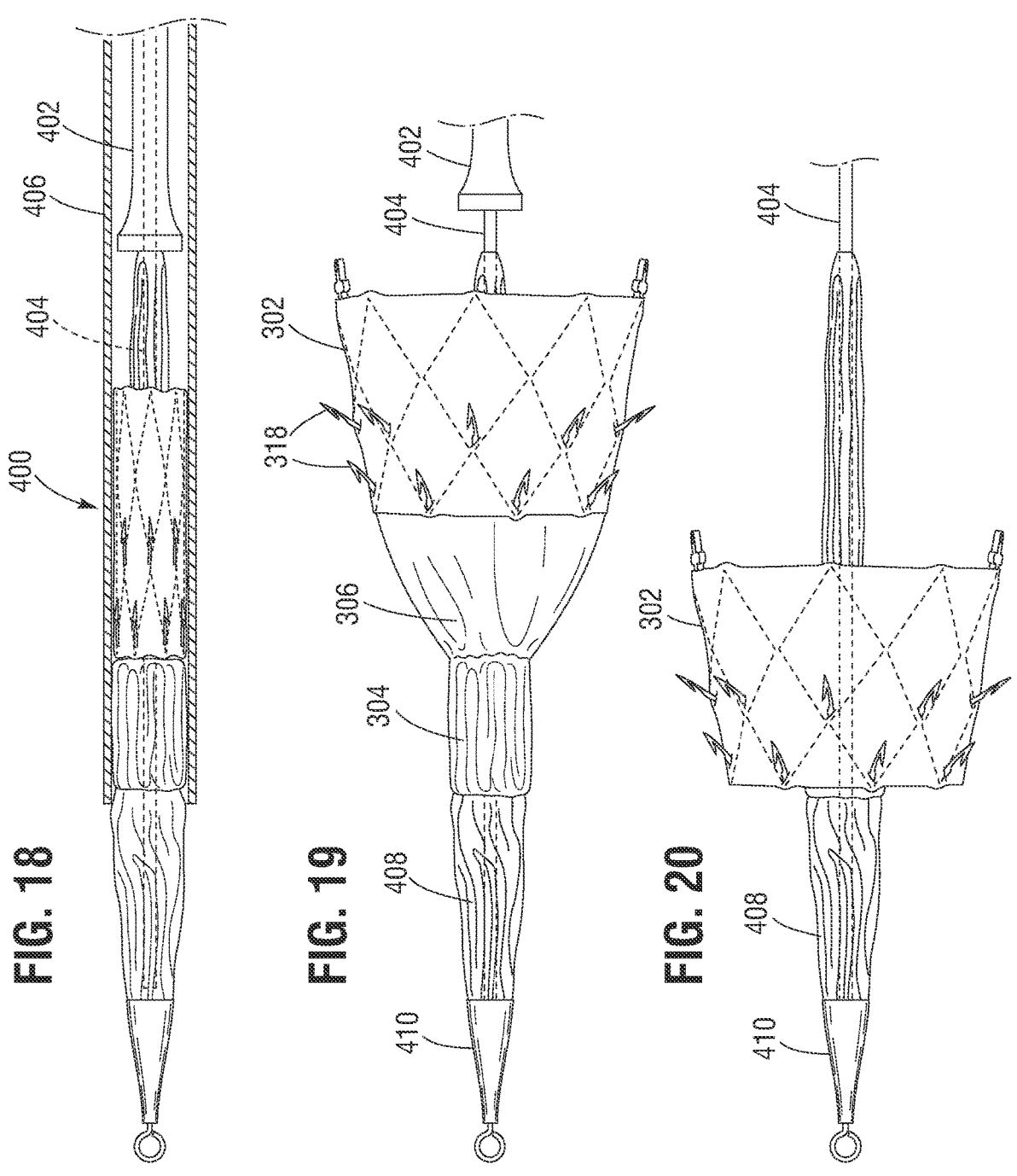
Figure 23:
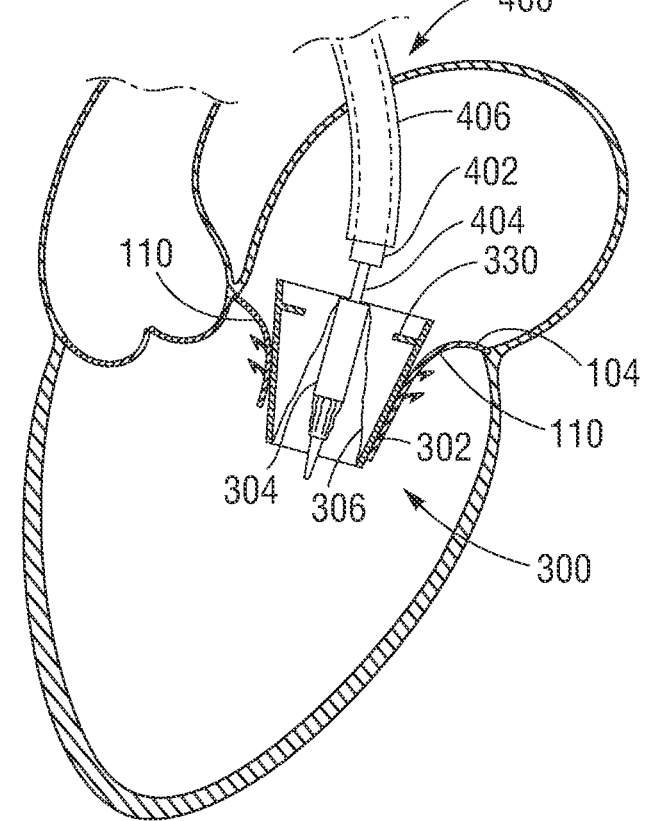

Following deployment of the support structure 302, the valve component 304 is moved axially to a position within the support structure 302 by retracting the delivery apparatus 400, as shown in FIGS. 20 and 23. As the valve component 304 is retracted within the support structure 302, the flexible connector 306 moves to an inverted state within the support structure. The length of the flexible connector 306 is selected such that the inflow end portion of the valve component can project upwardly beyond the orifice of the sealing member 330 when the flexible connector is pulled taut by retraction of the valve component relative to the support structure.

Figure 21:
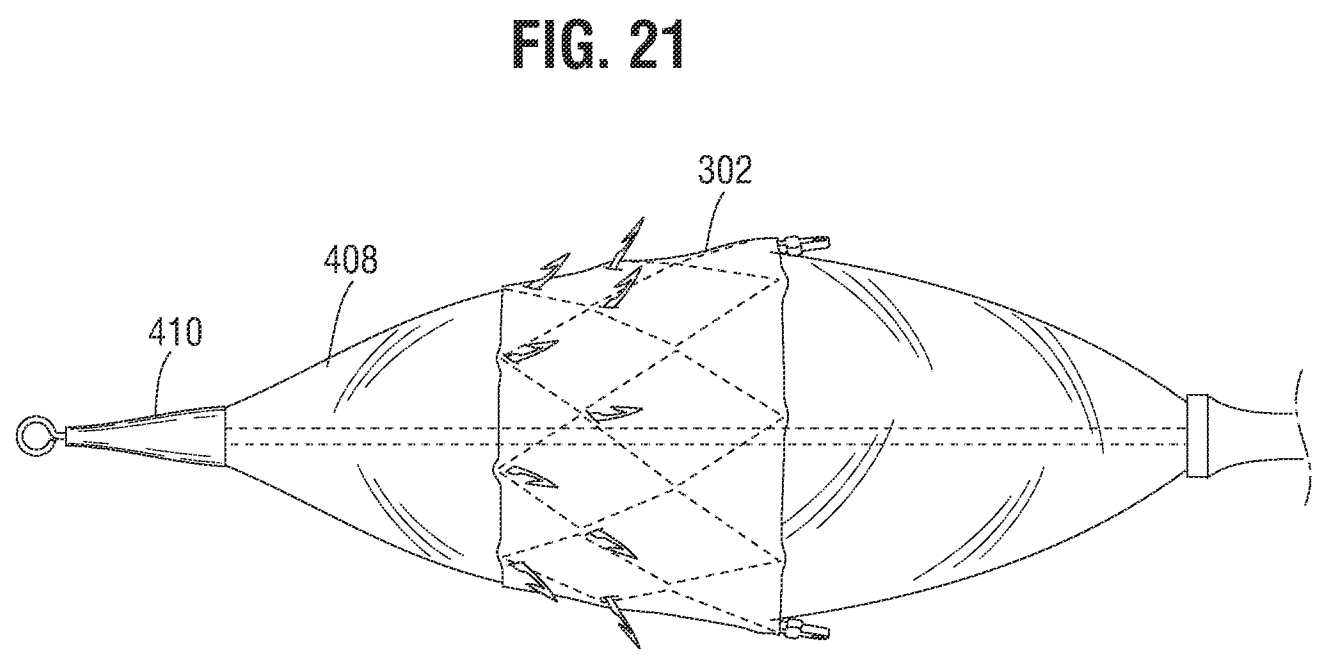
Figure 24:
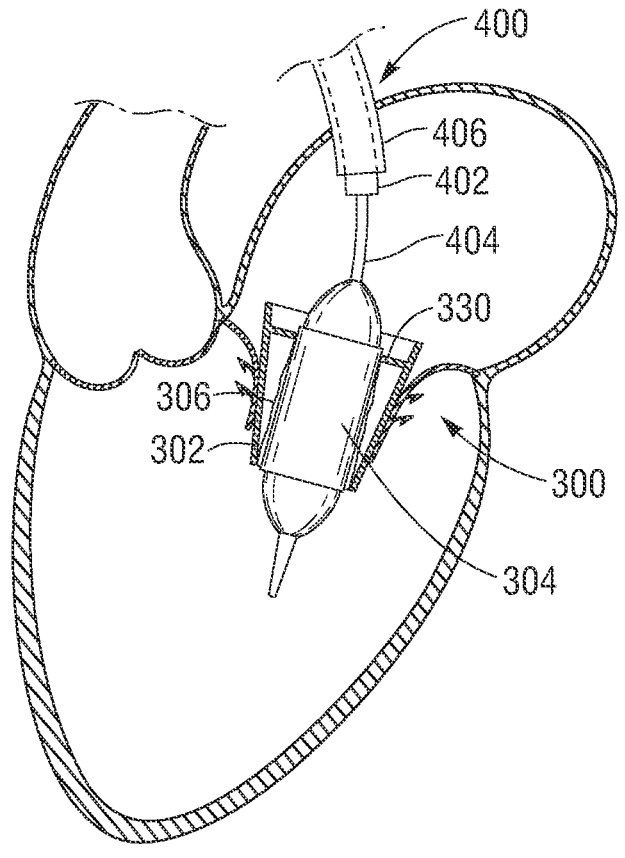

Referring to FIGS. 21 and 24, the balloon 408 can then be inflated to radially expand the valve component 304 inside of the support structure 302. The inflow end portion of the valve component 304 can expand against the inner peripheral edge (defining the orifice 332) of the sealing member 330 to help secure the valve component in place within the support structure. As noted above, in the illustrated embodiment, engagement of the valve component with the sealing member 330 and the flexible connector 306 anchor the valve component in place against hemodynamic pressure. After expansion of the valve component 304, the balloon can be deflated and the delivery apparatus can be removed from the body, leaving the valve assembly 300 implanted in the native mitral valve (FIG. 25).

In alternative embodiments, the valve assembly 300 can be delivered via other delivery techniques, such as trans-ventricular, transatrial, transfemoral, etc. Also, in alternative embodiments, the delivery apparatus 400 can be configured to deploy a self-expandable valve component 304 and/or a plastically-expandable support structure 302.

Figure 26:
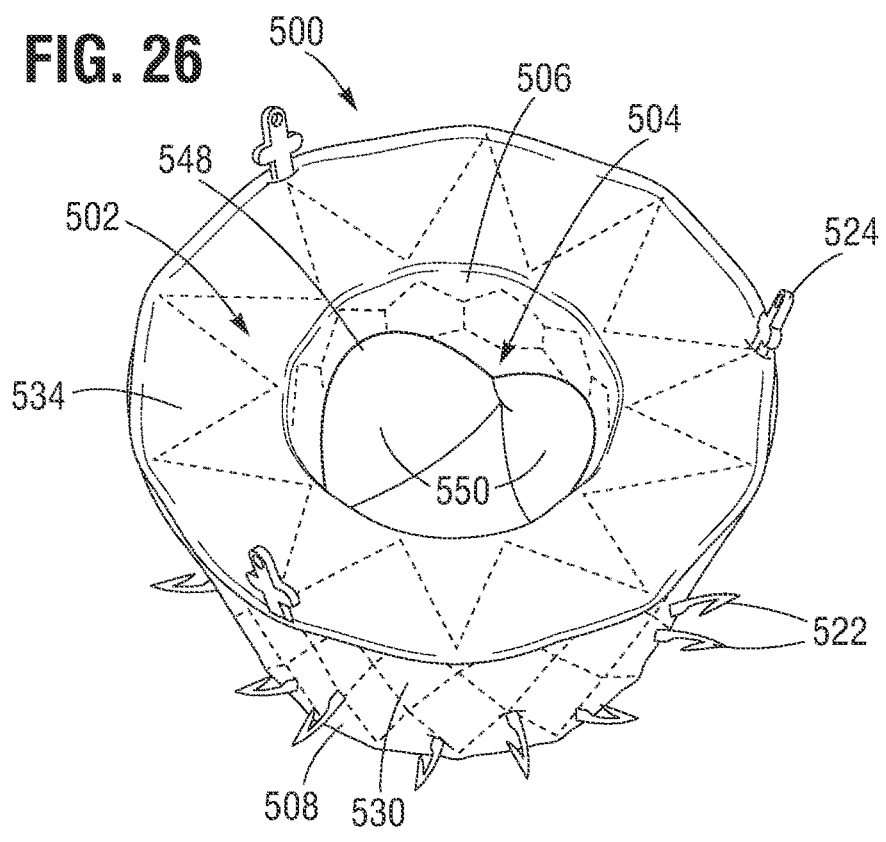
FIG. 26 is a perspective view of a prosthetic valve assembly as viewed from the inflow end of the valve assembly, according to another embodiment.
Figure 27:
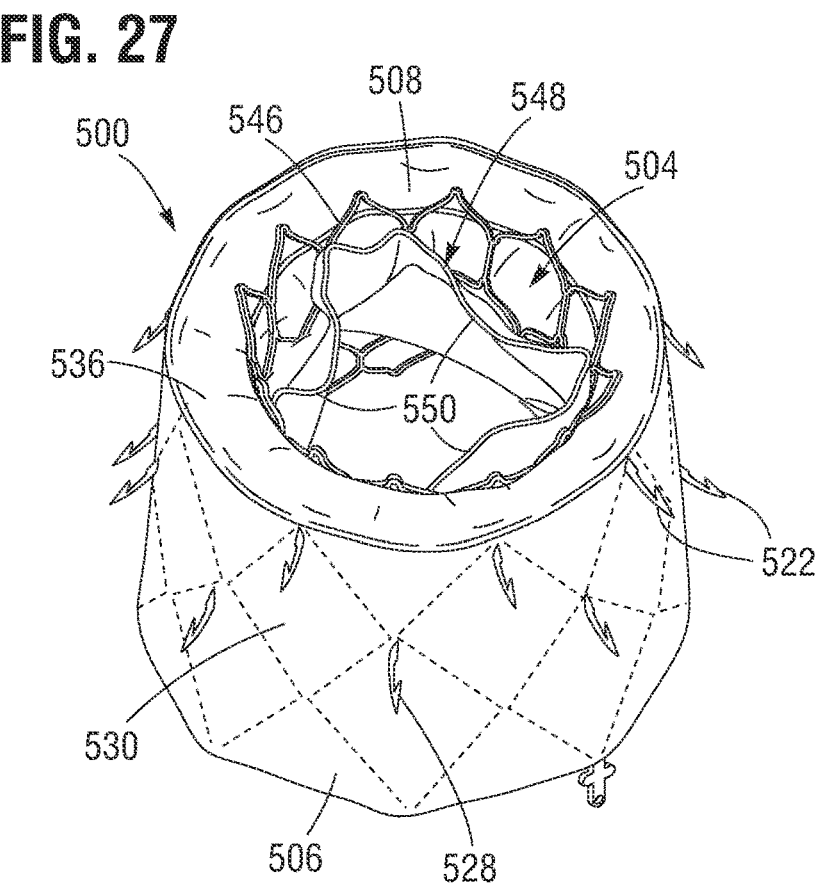
FIG. 27 is a perspective view of the prosthetic valve assembly of FIG. 26, as viewed from the outflow end of the valve assembly.

FIGS. 26-33 show an example of a prosthetic valve assembly 500, according to another embodiment. Referring to FIGS. 26-27, the prosthetic valve 500 can generally comprise a support structure 502 and a valve component 504 supported by and/or within the support structure 502, as further described below. The support structure 502 can be configured to securely engage a native annulus of a heart (e.g., similar to the manner shown in FIG. 3) to prevent the prosthetic valve assembly 500 from migrating within the native annulus. The valve component 504 can be configured for regulating the flow of blood in one direction through the prosthetic valve assembly 500, i.e., from an inflow end 506 to an outflow end 508 of the prosthetic valve 500. The valve component 504 can be separate component from the support structure 502 that is delivered and deployed within the support structure 502 after the support structure 502 is implanted within a native valve, such as the native mitral valve, as further described below.

Figures 28, 29, 30:
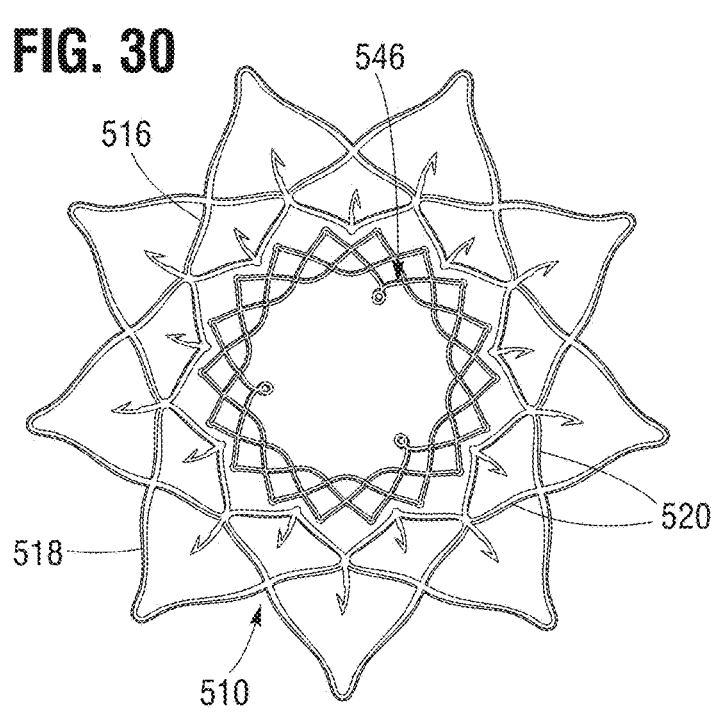
FIG. 28 is a perspective view of the support structure of the valve assembly of FIG. 26, as viewed from the inflow end of the support structure.
FIG. 29 is a perspective view of the support structure of FIG. 28, as viewed from the outflow end of the support structure.
FIG. 30 is a top plan view of two frames that can be used in the valve component and the support structure of the prosthetic valve assembly of FIG. 26.

Referring now to FIGS. 28-29, the support structure 502 of the prosthetic valve assembly 500 can comprise a frame 510, a blood-impervious sealing member or sealing portion 512 substantially covering the frame 510, and a radially centrally disposed opening or orifice 514 extending axially through the sealing member 512.

As best shown in FIG. 30, the frame 510 can comprise a main body 516 and, optionally, an enlarged atrial flange 518 (not shown in FIGS. 26-29, 31-33) extending both radially outward and axially upward from an atrial end 26 of the main body 22. The frame 510 is desirably covered by the sealing 512, as further described below. Although not shown, the atrial flange 518 of the frame 510 also can be covered by the sealing member 512, effectively forming an atrial sealing member (e.g., similar to atrial sealing member 17) of the support structure 502.

Referring again to FIGS. 28-29, the main body 516 of the frame 510 can comprise a plurality of interconnected angled struts 520, a plurality of tissue-engaging projections 522, and at least one positioning member 524 (three in the illustrated embodiment) and can be configured in a manner similar to the main body 22 of the frame 12. In the illustrated embodiment, the end of each projection 522 has barb or hook portion 528, as best shown in FIG. 29. In some embodiments, the projections can be configured without the hook portions (e.g., as shown in FIG. 4).

In some embodiments, main body 516 of the frame can be radially tapered in a direction extending from the inflow end to the outflow end (e.g., the inflow end is slightly radially larger than in outflow end). For example, in one particular embodiment, the axial cross-sectional profile of the main body 516 can slope ten degrees radially inwardly (similar to a "V-shape") from the inflow end to the outflow end of the main body 516.

The frame 510 can be formed from a flexible, shape-memory material (e.g., Nitinol) to enable self-expansion from a radially compressed state to a radially expanded state. As such, the support structure 502 of the prosthetic valve 500 can be radially collapsible and self-expandable between a radially expanded state (e.g., FIGS. 26-29) and a radially compressed state (not shown) to enable delivery and implantation at the mitral valve region of the heart (or within another native heart valve). In alternative embodiments embodiments, the frame 510 can be formed from a plastically-expandable material (e.g., stainless steel or chromium alloys), and is configured to be expanded by an expansion device, such as an inflatable balloon.

The sealing member 512 of the support structure 502 can comprise an outer sleeve 530, an inner tube or sleeve 532, and first and second support members or end walls 534, 536. The outer sleeve portion 530 can be disposed around the outer circumferential surface of the main body 516 of the frame 510 and can extend axially from the inflow end 506 to the outflow end 508 of the prosthetic valve 500. The outer sleeve can be coupled or secured to the frame 510 such as by sutures or an adhesive, and the projections 522 of the frame 510 can penetrate through the outer sleeve portion 530 (or extend through openings which can be formed in the outer sleeve portion 530). The inner sleeve 532 can be disposed radially inwardly from the outer sleeve 530 and can extend axially from the inflow end 506 to the outflow end 508 of the prosthetic valve assembly 500 (e.g., substantially parallel to the outer sleeve 530).

The first end wall 534 can extend radially inwardly from a first end portion 538 of the outer sleeve 530 and has a respective inner peripheral edge defining a respective orifice. The second end wall 536 can extend radially inwardly from a second end portion 542 of the outer sleeve 530 and has a respective inner peripheral edge defining a respective orifice. The inner sleeve 532 can extend between the first and second end walls and can have a first end portion 540 connected to the inner peripheral edge of the first end wall 534 and a second end portion 544 connected to the inner peripheral edge of the second end wall 536. The first and second end walls 534, 536 can have respective opposing major surfaces facing in the axial direction and function to block the flow of blood in the annular space between the frame 510 and the valve component 504.

The first end portions 538, 540 of the sleeves 530, 532 and the first end wall 534 and the second end portions 542, 544 of the sleeves 530, 532 and the second end wall 536 can be secured together in various ways. For example, in some embodiments, the sleeves 530, 532 and the end walls 534, 536 can be secured together by sutures, ultrasonic welding, and/or an adhesive. In other embodiments, one or more of the sleeves 530, 532 and one or more of the end walls 534, 536 can be secured together by forming the sleeve(s) and the support member(s) from a single, unitary piece of material.

The sealing member 512 extends radially inwardly from the frame 512 to the inner sleeve 532 and axially from the inflow end 506 to the outflow end 508, thereby forming the lumen 514 which extends axially through the support structure 502 for receiving the valve component 504. As a result, the support structure 502 can be configured such that the frame 510 has an outer diameter that is substantially the same or slightly larger than the inner diameter of the native annulus and the orifice 514 has an inner diameter that is smaller than the inner diameter of the native annulus. This can advantageously allow the valve component 504 to be smaller than the native annulus (see, e.g., FIG. 25) for desired hemodynamics while the support structure 502 can be sized to fill the native annulus and prevent or at least minimize paravalvular leakage between the native annulus and the valve assembly 500.

The sealing member 512 can be formed from various suitable blood-impervious materials such as polyethylene terephthalate ("PET") fabric. As such, when the support structure 502 is disposed and secured in a native annulus (e g, similar to the support structure 302 in FIG. 22), the support structure 502 can direct the flow of blood through the valve component 504 (which can be disposed in the orifice 514, as best shown in FIGS. 26-27) and can at least substantially prevent the flow of blood through and/or around the support structure 502.

The support structure 502 can be configured such that the inner sleeve 532 and/or the end walls 534, 536 are relatively non-expansible or non-extensible in the radial direction and can securely support the valve component 504 when the valve component 504 is deployed in the orifice 514, as shown, for example, in FIGS. 26-27 and further described below. This can be accomplished, for example, by orienting and/or configuring the fabric of the inner sleeve 532 and/or the end walls 534, 536 as described above with respect to the embodiments of the sealing member 330 of FIGS. 14-17. In some embodiments, the support structure 502 can include struts or ribs extending radially between the outer sleeve 530 and the inner sleeve 532. The struts or ribs can be spaced axially and/or circumferentially relative to each other within the space defined by the inner sleeve, outer sleeve, and the end walls of the sealing member.

Referring now to FIGS. 26-27, the valve component 504 can comprise frame 546 and a valve structure 548 having a plurality of leaflets 550 (three in the illustrated embodiment). As noted above, the valve component 504 can be configured for regulating the flow of blood from an inflow end 506 to an outflow end 508 of the prosthetic valve assembly 500. The valve component 504 can be configured similar to the valve component 304. The valve component 504 can further include an outer sleeve or cover (similar to cover 324) to enhance engagement with the inner surface of the inner sleeve 532. The frame 546 can be made from any of the self-expandable, shape-memory materials or plastically-expandable materials described above.

The prosthetic valve assembly 500 can be delivered and or deployed in various ways and/or with various delivery apparatuses. For example, in some embodiments, the prosthetic valve 500 can be releasably attached to the delivery apparatus 400, delivered trans-septally, and deployed within a native mitral valve annulus similar to the manner shown in FIGS. 18-25 and described above. In other words, in such embodiments, the prosthetic valve assembly 500 can be delivered and deployed with one delivery apparatus.

In other embodiments, the support structure 502 of the prosthetic valve assembly 500 can be delivered and deployed using a first delivery apparatus and a delivery approach (e.g., trans-septally), and then the valve component 504 of the prosthetic valve assembly 500 can be delivered and deployed using a second delivery apparatus and the same delivery approach (e.g., trans-septally).

For example, the support structure 502 of the prosthetic valve assembly 500 can be radially compressed and retained within a delivery cylinder of a first delivery apparatus (not shown). The first delivery apparatus can be inserted into a patient's body and advanced to or adjacent a native mitral valve annulus using trans-septal delivery approach. The support structure 502 can then be deployed from within the delivery cylinder, which can allow the support structure 502 to radially expand. The support structure 502 can then be desirably positioned and secured within the native annulus and released from the first delivery apparatus. The first delivery apparatus can then be removed from the patient's body, leaving the support structure 502 securely positioned in the native mitral valve annulus.

Figures 31, 32, 33:
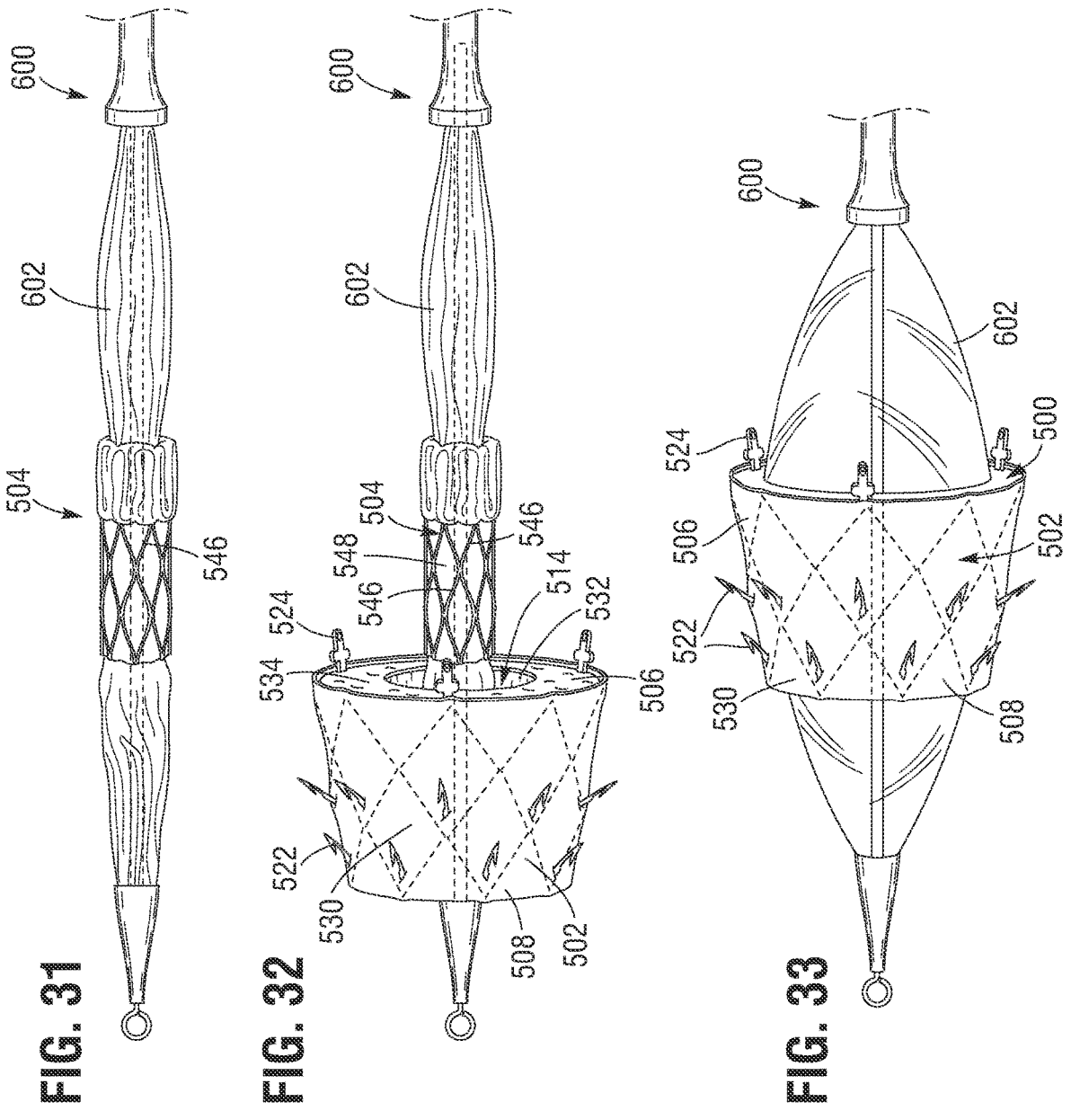
FIGS. 31-33 show an embodiment of a delivery apparatus in various stages of deploying the prosthetic valve assembly of FIG. 26.

Referring to FIG. 31, the valve component 504 can be crimped onto a balloon portion 602 of a second delivery apparatus 600. Although not shown, the second delivery apparatus 600 can comprise various other components such a delivery cylinder, etc, can have the same construction as the delivery apparatus 400. The second delivery apparatus 600 can be inserted into a patient's body and advanced to or adjacent the native mitral valve annulus using a trans-septal delivery approach.

As best shown in FIGS. 32-33, the second delivery apparatus 600 can be advanced into and/or through the orifice 514 of the support structure 502 such that the valve component 504 is disposed within the orifice 514. As shown in FIG. 33, the valve component 504 can be deployed, and thus secured to the support structure 502, by inflating the balloon portion 602 of the second delivery apparatus 600. This can cause the valve component 504 to radially expand against the inner sleeve 532 of the support structure 502, thus securing the valve component 504 to the support structure 502, as best shown in FIGS. 26 and 27. The balloon portion 602 of the second delivery apparatus 600 can then be deflated, and the second delivery apparatus can be removed from the patient's body, leaving the prosthetic valve 500 securely positioned in the native mitral valve annulus.

Although not shown, in some embodiments, the support structure 502 can comprise a temporary valve component (e.g., temporary leaflets within the orifice 514) which can be configured to regulate the flow of blood in one direction for the duration between deploying the support structure 502 and deploying the valve component 504. The temporary valve component can be configured to be displaced (e.g., crushed) when the valve component 504 is radially expanded within the orifice 514 of the support structure 502, and the valve component 504 can assume regulating the flow of blood in one direction. The temporary leaflets can be relatively thinner and less durable than the leaflets of the valve component as they are intended to function for a relatively short period until the valve component 504 is implanted.

In other embodiments, the support structure 502 of the prosthetic valve assembly 500 can be delivered and deployed using a first delivery apparatus and a first delivery approach (e.g., trans-septally), and the valve component 504 of the prosthetic valve assembly 500 can be delivered and deployed using a second delivery apparatus and a second delivery approach (e.g., transventricularly). This can advantageously reduce the implantation procedure time and/or reduce the duration between the deployment of the support structure 502 and the valve component 504 because the valve component 504 can inserted into the support structure 502 without having to remove the first delivery apparatus from the patient's body and then insert and advance the second delivery apparatus into the patient's body via the same delivery path.

Figure 34:
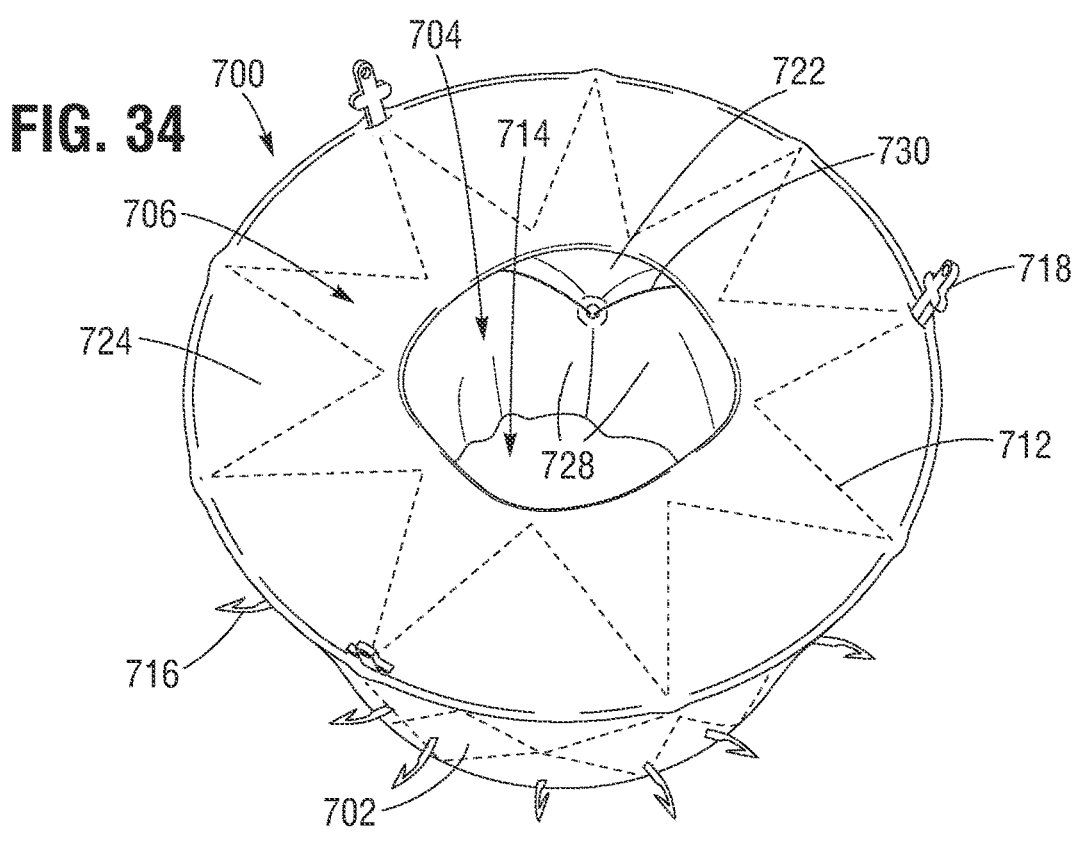
FIG. 34 is a perspective view of a prosthetic valve assembly as viewed from the inflow end of the valve assembly, according to another embodiment.
Figure 35:
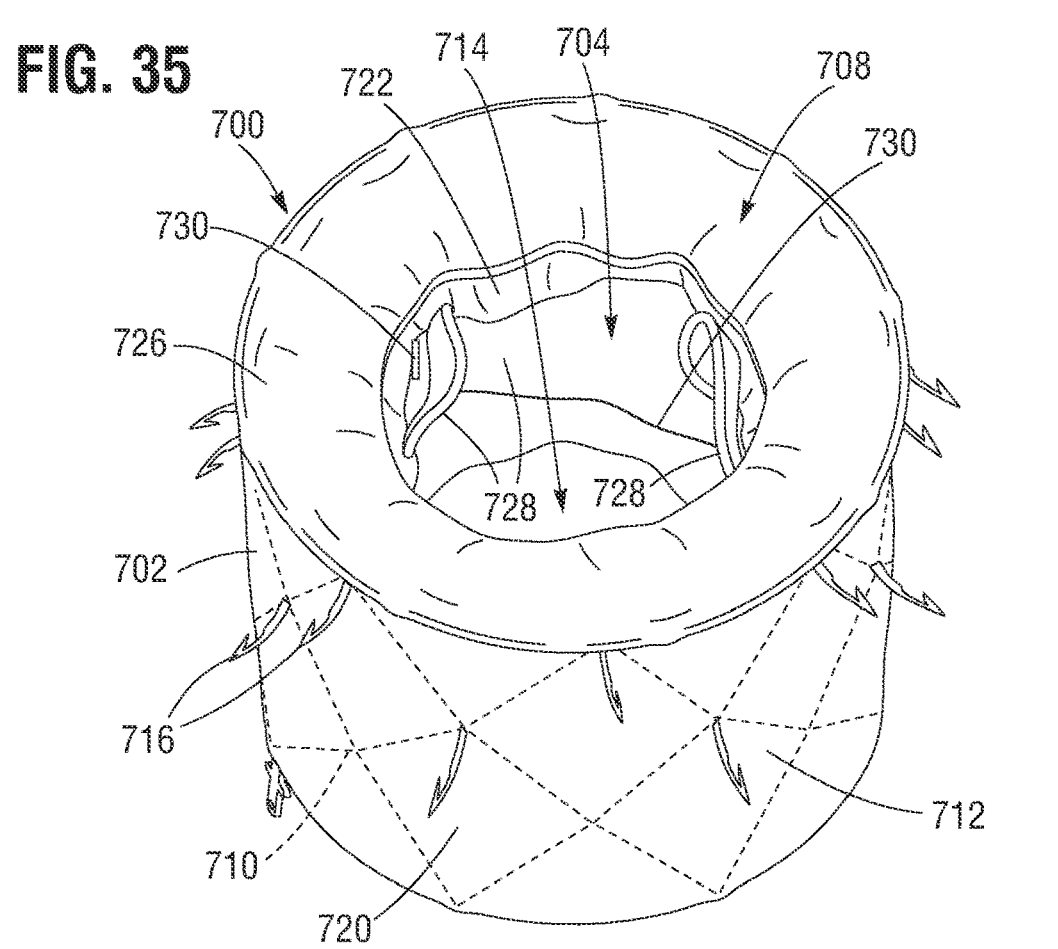
FIG. 35 is a perspective view of the prosthetic valve assembly of FIG. 34, as viewed from the outflow end of the valve assembly.

FIGS. 34-35 show an example of a prosthetic valve assembly 700, according to another embodiment. The prosthetic valve assembly 700 can generally comprise a support structure 702 and a valve component 704 coupled or secured within the support structure 702, as further described below. The support structure 702 can be configured to securely engage a native annulus of a heart (e.g., similar to the manner shown in FIG. 3) to prevent the prosthetic valve assembly 700 from migrating within the native annulus. The valve component 704 can be configured for regulating the flow of blood in one direction through the prosthetic valve assembly 700, i.e., from an inflow end 706 to an outflow end 708 of the prosthetic valve assembly 700.

The support structure 702 of the prosthetic valve assembly 700 can comprise a frame 710, a blood-impervious sealing member 712 substantially covering the frame 710, and a radially centrally disposed opening or orifice 714 extending axially through the support structure 702. The support structure 702 can be configured similar to the support structure 502 of the prosthetic valve assembly 500. The frame 710 can comprise plurality of tissue-engaging projections 716 and one or more positioning members 718

(three in the illustrated embodiment). The cloth portion 712 can comprise an outer sleeve 720, an inner sleeve 722, and first and second support members or end walls 724, 726.

The valve component 704 can comprise a plurality of leaflets 728 (three in the illustrated embodiment). The valve component 704 can be coupled or secured to the inner sleeve 722 of the support structure 702 in various ways such as by sutures 730 and/or by an adhesive.

In some embodiments, the leaflets 728 can, for example, be prosthetic and/or bio-prosthetic leaflets configured to permanently regulate the flow of blood in one direction. In this manner, the prosthetic valve 700 can be configured substantially similar to the prosthetic valve assembly 500 except the valve component 704 of the prosthetic valve 700 does not have a separate frame like the frame 546 of the valve component 504; rather, the valve component 704 and the support structure 702 are pre-assembled as a single unit. As such, the support structure 702 and the valve component 704 of the prosthetic valve 700 can be deployed simultaneously rather than sequentially like the support structure 502 and the valve component 504 of the prosthetic valve assembly 500.

In other embodiments, the leaflets 728 can, for example, be temporary leaflets (e.g., cloth leaflets) configured to temporarily regulate the flow of blood in one direction and to be displaced by a later-deployed valve component which can assume regulating the flow of blood in one direction. It should be noted that in any of the disclosed embodiments, the leaflets can be temporary leaflets configured to be displaced by a later-deployed valve structure having permanent leaflets.

Figures 36, 37:
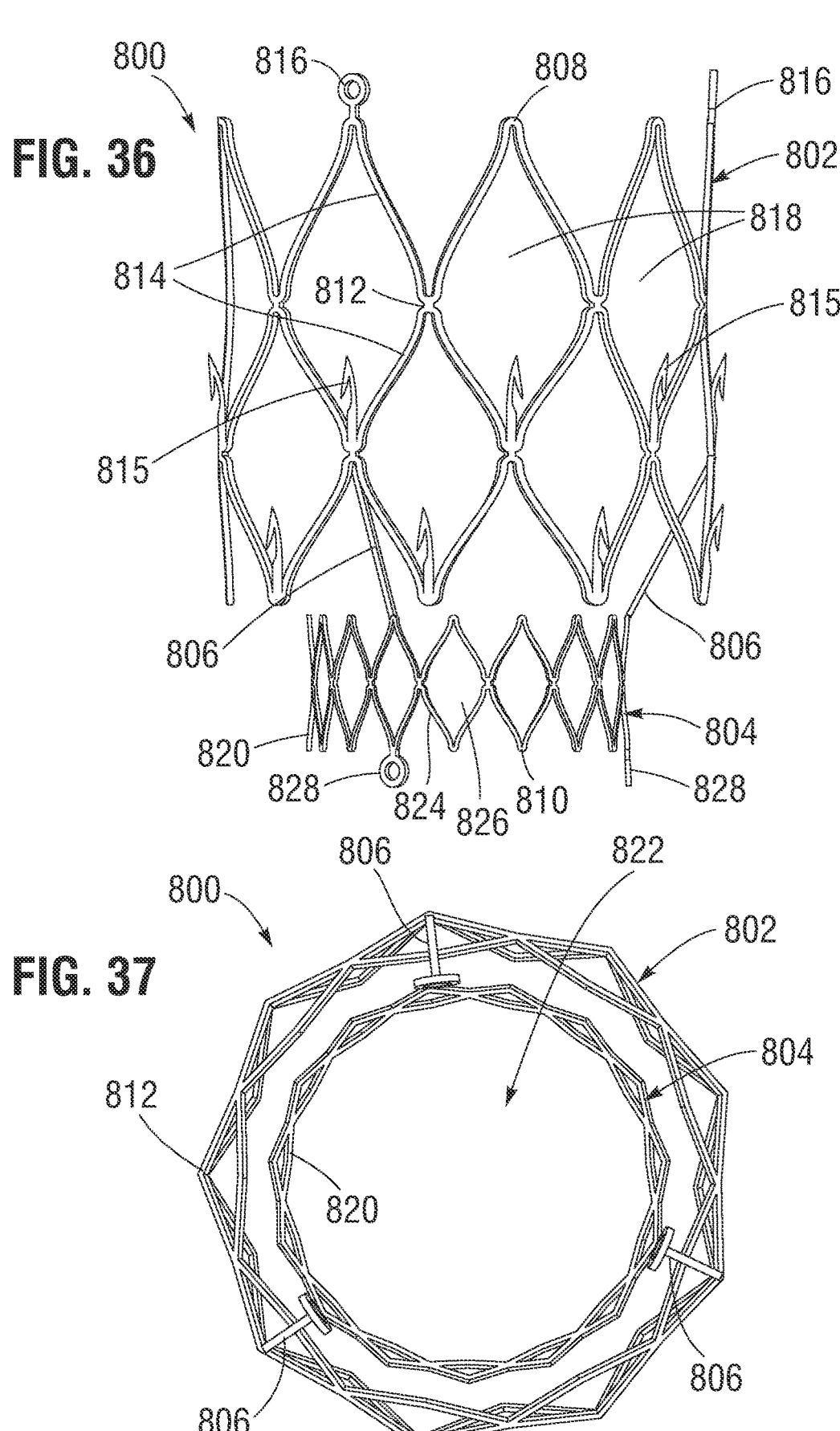
FIG. 36 is a side view of a frame structure of a prosthetic valve, according to another embodiment.
FIG. 37 is a top plan view of the frame structure of FIG. 36.

FIGS. 36-37 show an example of a prosthetic valve 800, according to another embodiment. The prosthetic valve 800 can generally comprise a support structure 802 and a valve component 804 coupled or secured within the support structure 802 by one or more connecting members or struts 806 (three in the illustrated embodiment). The support structure 802 can be configured to securely engage a native annulus of a heart (e.g., similar to the manner shown in FIG. 3) to prevent the prosthetic valve 800 from migrating within the native annulus. The valve component 804 can be configured for regulating the flow of blood in one direction through the prosthetic valve 800, i.e., from an inflow end 808 to an outflow end 810 of the prosthetic valve 800.

The support structure 802 can comprise a frame 812 and a blood-impervious sealing member (e.g., formed from a fabric or cloth) (not shown for purposes of illustration). The frame 812 can be configured similar to, for example, the frame 500 and can comprise a plurality of interconnected struts 814, a plurality of tissue-engaging projections 815, and one or more first positioning members 816 (three in the illustrated embodiment) axially extending from the inflow end 808 of the frame 812. The struts 814 can configured to form cells 818 which can be arranged in circumferentially extending rows (e.g., two rows in the illustrated embodiment).

Although not shown, the sealing member can be configured similar to the sealing member 512 and can comprise an outer sleeve extending circumferentially around and covering an outer surface of the frame 812, an inner sleeve disposed radially inward from the outer sleeve and the an inner surface of the frame 812, and first and second end walls extending radially between and connecting first and second ends of the sleeves, respectively.

In some embodiments, the inner sleeve of the sealing member can be substantially cylindrically shaped and can have an inner diameter that is substantially the same as the inner diameter of a frame 820 of the valve component 804. As such, the inner sleeve can form a substantially cylindrical orifice or lumen which extends axially from the inflow end 808 of the prosthetic valve to or adjacent an orifice or lumen 822 of the valve component 808.

In other embodiments, the inner sleeve of the cloth portion can be substantially conically shaped and can have a first inner diameter at the first end of the inner sleeve which is substantially the same as the inner diameter of inflow end 808 of the frame 812. From the first end, the inner sleeve can taper radially inwardly and can have a second inner diameter at the second end of the inner sleeve which is substantially the same as the inner diameter as an inner diameter of a frame 820 of the valve component 804. As such, the inner sleeve can form a substantially conical orifice which extends axially from the inflow end 808 of the prosthetic valve to or adjacent the orifice 822 of the valve component 808 (similar to a funnel).

The valve component 804 of the prosthetic valve 800 can be configured similar to the valve component 502. As noted above, the valve component 804 can comprise the frame 820 and the orifice 820. Although not shown, the valve component can comprise a valve structure which can be configured (e.g., with leaflets) for regulating the flow of blood in one direction through the prosthetic valve 800 from the inflow end 808 to the outflow end 810 of the prosthetic valve 800.

The frame 820 can be formed by a plurality of interconnected struts 824. The struts 824 can be configured to form cells 826 which can be arranged in circumferentially extending rows (e.g., one row in the illustrated embodiment). In some embodiments, the frame 820 can have more than one row of cells 826. The frame 820 can also have one or more second positioning members 828 (three in the illustrated embodiment) axially extending from the outflow end 810 of the frame 820. The second positioning members 828 can be used, for example, in lieu of or in addition to the first positioning members 816 to connect the outflow end 810 of the prosthetic valve to a delivery apparatus.

The frame 820 of the valve component 804 can have an outer diameter that is smaller than the inner diameter of the frame 812 of the support structure 802. As such, the frame 820 can securely engage a native annulus (e.g., a native mitral valve annulus) and the valve component can be smaller than the native annulus and supported by the frame 820 of the support structure 802.

The struts 806 of the prosthetic valve 800 can extend between and can be connected or coupled to the frame 812 of the support structure 802 and the frame 820 of the valve component 804. The struts 806 can be configured to extend axially from the frame 812 toward the outflow end 810 of the prosthetic valve 800 (as best shown in FIG. 36) and to extend radially inwardly (as best shown in FIG. 37). In the illustrated embodiment, the struts 806 are connected to an outflow end portion of the frame 812 at first ends of the struts and connected to an inflow end portion of the frame 820 at second ends of the struts. In some embodiments, a length and/or positioning of the struts 806 can be configured such that the valve component 804 at least partially axially overlaps or is nested within the support structure 802. In other embodiments, the length and/or positioning of the struts 806 can be configured such that the valve component 804 does not substantially axially overlap or nest within the support structure 802. In some embodiments, the length and/or the angle of the struts 806 can configured to increase or decrease the radial distance between the valve structure 802 and the valve component 804.

The frames 812, 820 can be formed from any suitable self-expanding, shape-memory materials or plastically-expandable materials described above. In some embodiments, both the support structure and the valve component are self-expandable or are both plastically expandable. In other embodiments, one of the support structure and the valve component is self-expandable and the other is plastically-expandable by an expansion device such as a balloon.

The struts 806 can be connected or coupled to the frames 812, 820 in various ways. For example, as shown in the illustrated embodiment, the struts 806 can be connected to the frames 812, 820 by forming the struts 806 and the frames 812, 820 from a single unitary piece of material. This can be accomplished, for example, by laser cutting a metal (e.g., Nitinol) tube, and shape setting the struts 806 and the frames 812, 820 in their respective configurations. In other embodiments, the struts 806 can be coupled to connected to the frames 812, 820 by welding, fasteners, and/or an adhesive.

Although not shown, the prosthetic valve 800 can be attached to a delivery apparatus, inserted into a patient's body, and deployed at an implantation site (e.g., a native mitral valve annulus) in various ways. For example, the prosthetic valve 800 can be radially compressed and retained within a delivery cylinder of a delivery apparatus. The delivery apparatus can be inserted into a patient's body and advanced to or adjacent a native mitral valve annulus using trans-septal delivery approach. The prosthetic valve 800 can then be deployed from within the delivery cylinder, which can allow the prosthetic valve 800 to radially expand and engage the tissue of the native mitral valve annulus. The prosthetic valve 800 can then be desirably positioned and secured within the native mitral valve annulus and released from the delivery apparatus (see, e.g., FIG. 3). The delivery apparatus can then be removed from the patient's body, leaving the prosthetic valve 800 securely positioned in the native mitral valve annulus.

Figure 41:
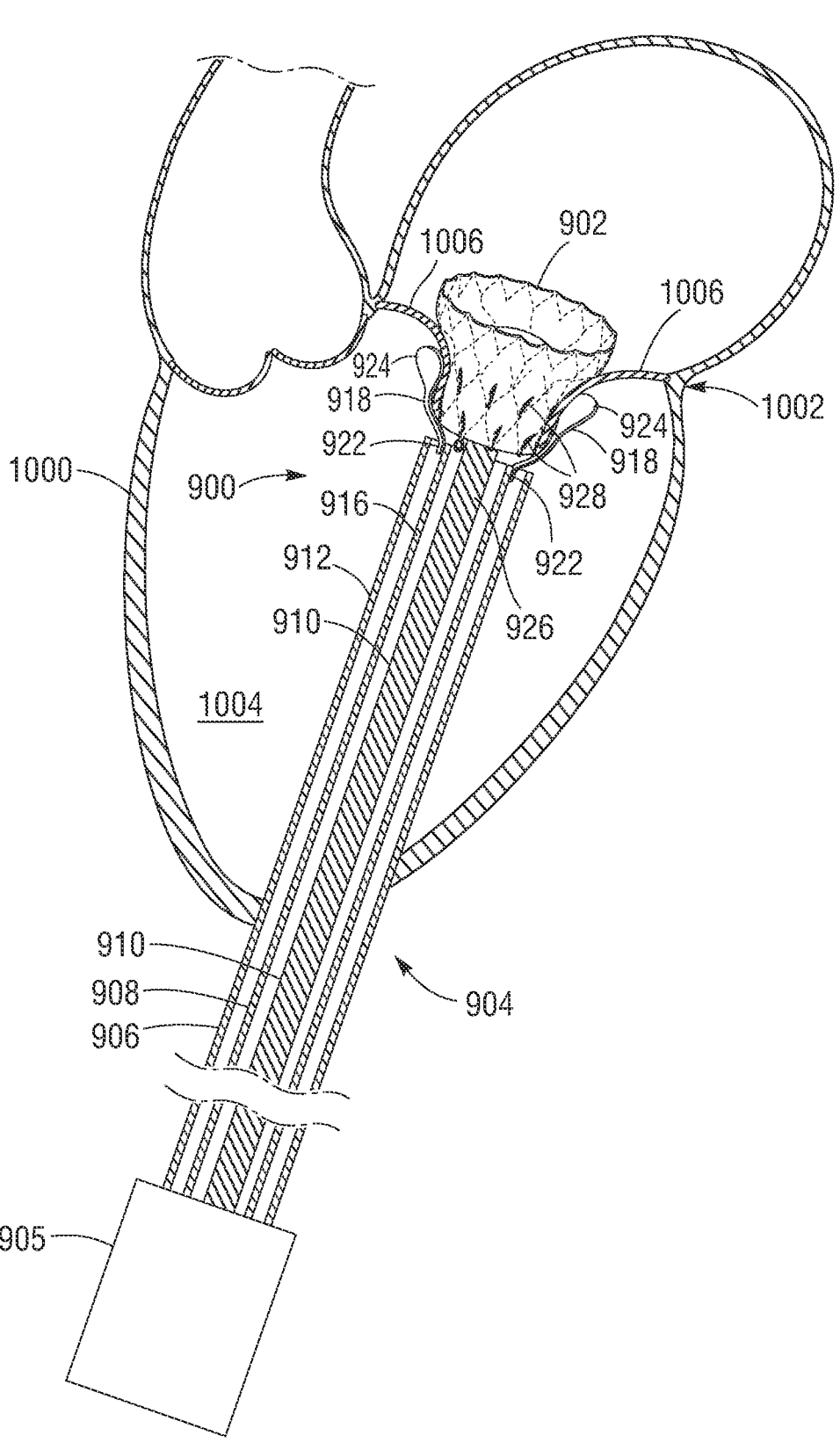

FIGS. 38-41 show an exemplary embodiment of a prosthetic heart valve delivery assembly 900. Referring to FIG. 41, the delivery assembly 900 can comprise an expandable prosthetic heart valve 902 and a delivery apparatus 904.

Figures 38, 39, 40:
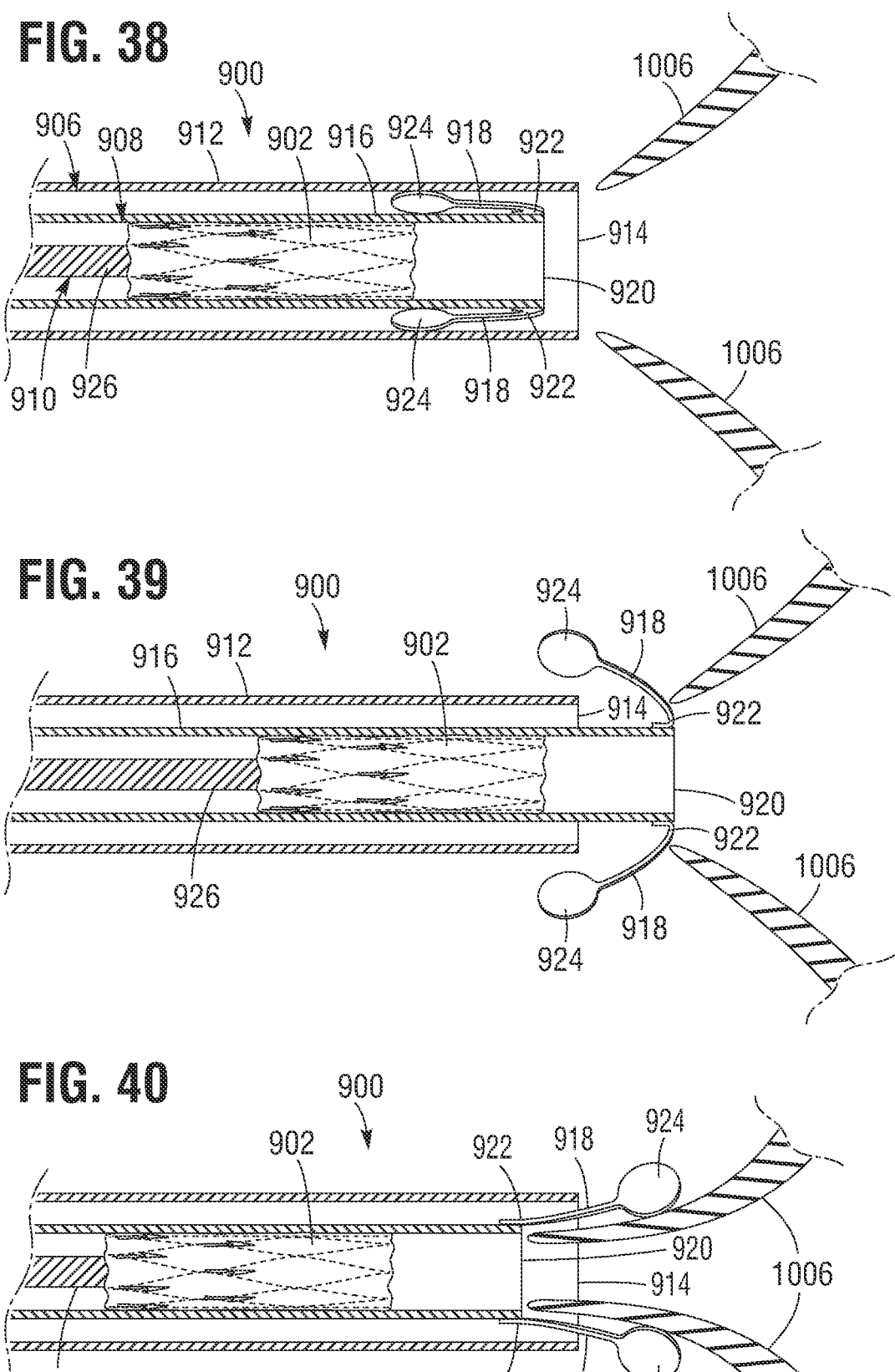
FIGS. 38-41 show an embodiment of a delivery apparatus in various stages of deploying a prosthetic valve in a native mitral valve of a heart.

The prosthetic valve 902 can configured in a manner similar to the prosthetic heart valves and/or assemblies 10, 300, 500, 700, 800. The prosthetic valve 902 can be configured to be radially expandable from a compressed state (e.g., as shown in FIGS. 38-40) to an expanded state (e.g., as shown in FIG. 41), and vice versa. In some embodiments, as shown, the prosthetic heart valve 902 can be a self-expanding valve. In other embodiments, the prosthetic heart valve 902 can be mechanically expanding valve (e.g., a balloon expandable valve). The prosthetic heart valve 900 can be releasably coupled to the delivery apparatus 904, as further described below.

Referring still to FIG. 41, the delivery apparatus 904 can comprise a handle 905, a first catheter 906, a second catheter 908, and a third catheter 910. Proximal end portions of the catheters 906, 908, 910 can be coupled to the handle 905 and can extend distally away from the handle 905 toward distal end portions of the catheters 906, 908, 910. The second and third catheters 908, 910, can extend coaxially through the first catheter 908, and the third catheter 910 can extend coaxially through the second catheter 908. The catheters 906, 908, 910 can be independently movable (e.g., axially and/or rotationally) relative to each other.

The handle 905 can be used to adjust the positioning of the prosthetic heart valve 902 and the delivery apparatus 904 relative to a patient's body (e.g., the patient's heart). In some embodiments, the handle 905 can comprise a plurality of control knobs (not shown) (e.g., one knob for each of the catheters 906, 908, 910), and the control knobs can be configured to adjust the relative positioning of the catheters 906, 908, 910.

In some embodiments, the handle 905 and the catheters 906, 908, 910 can be configured to translate relative rotational movement (e.g., clockwise and counterclockwise movement) between the catheters 906, 908, 910 at the proximal end portions of the catheters 906, 908, 910 into relative axial movement (e.g., proximal and distal relative movement) between the catheters 906, 908, 910 at the distal end portions of the catheters 906, 908, 910. This can be accomplished, for example, by configuring the delivery apparatus 904 similar to the manner described in U.S. Pat. No. 8,652,202, which is incorporated herein by reference.

Referring to FIG. 38, the first catheter 906 can comprise an elongate shaft having a sleeve or sheath portion 912 disposed at or near the distal end portion 914 of the first catheter 906. The sheath portion 912 of the first catheter 906 can be configured to compress a portion of the second catheter 908 and/or retain a portion of the second catheter 906 in a compressed state, as further described below.

The second catheter 908 can comprise an elongate shaft have a sleeve or sheath portion 916 and a plurality of flexible paddles or arms 918 (e.g., two in the illustrated embodiment) disposed at or near the distal end portion 920 of the second catheter 908. The sheath portion 916 of the second catheter 908 can be used to compress and/or retain the prosthetic heart valve 902 in the compressed state, as further described below. The flexible arms 918 of the second catheter 908 can be coupled to and extend radially outward from the sheath portion 916 of the second catheter 908.

The flexible arms 918 of the second catheter 908 can be configured so as to be movable from one configuration to one or more other configurations, and vice versa. For example, the flexible arms 918 can be configured to be movable from a first configuration (e.g., a compressed configuration, as shown in FIG. 38) to a second configuration (e.g., a resting or undeflected configuration, as shown in FIG. 39) to a third configuration (e.g., a leaflet-retention configuration, as shown in FIGS. 40-41), and vice versa.

As shown in FIG. 38, in the first configuration, the flexible arms 918 can be angled axially away from the distal end portion 920 of the second catheter 908 and compressed against the sheath portion 916 of the second catheter 908. With the flexible arms 918 in the first configuration, the flexible arms 918 of the second catheter 908 can be positioned within the sheath portion 912 of the first catheter 906. The sheath portion 912 of the first catheter 906 can be configured to retain the flexible arms 918 of the second catheter 908 in the first configuration.

As shown in FIG. 39, the flexible arms 918 can be moved from the first configuration to the second configuration by exposing the flexible arms 918 from the sheath portion 912 of the first catheter 906. This can be accomplished by proximally retracting the first catheter 906 relative to the second catheter 908 (and/or by distally advancing the second catheter 908 relative to the first catheter 906) such that the flexible arms 918 extend from the distal end portion 914 of the first catheter 906. This allows the flexible arms 918 to expand radially outwardly away from the sheath portion 916 of the second catheter 908.

As shown in FIG. 40, the flexible arms 918 can be moved from the second configuration to the third configuration by moving the sheath portion 912 of the first catheter 906 back over the flexible arms 918. This can be accomplished by proximally retracting the second catheter 908 relative to the first catheter 906 (and/or by distally advancing the first catheter 906 relative to the second catheter 908) such that proximal portions 922 of the flexible arms 918 are disposed radially within the sheath portion 912 of the first catheter 906. This causes the flexible arms 918 to press against the sheath portion 912 at the distal end portion 914 of the first catheter 906, which in turn causes the distal portions 924 of the flexible arms 918 to initially move radially outwardly away from the sheath portion 916 of the second catheter 908. As the second catheter 908 is retracted farther proximally relative to the first catheter 906 (i.e., as distal portions 924 of the flexible arms 918 move toward the distal end portion 914 of the first catheter 906), the sheath portion 912 of the first catheter 906 causes the flexible arms 918 to pivot distally away from the sheath portion 916 of the second catheter 908 and the distal portions 924 of the flexible arms 918 to radially converge toward each other. The relative spacing between the distal portions 924 of the flexible members can be increased by distally advancing the second catheter 908 relative to the first catheter 906 (and/or by proximally retracting the first catheter 906 relative to the second catheter 908).

In alternative embodiments, the flexible arms 918 of the second catheter 908 can be configured to extend radially outwardly and distally away from the distal end 920 of the second catheter 908 (i.e., in the opposite direction of the flexible arms 918 shown in FIG. 38) when the flexible arms 918 are in the first configuration (i.e., the compressed configuration). In such embodiments, the flexible arms 918 can be configured to expand radially outwardly relative to each other and to be angled distally relative to the distal end portion 920 of the second catheter 908 when the flexible arms 918 are deployed from the sheath portion 912 of the first catheter 906. The relative distance between distal portions 924 of the flexible arms can be adjusted by moving the first and second catheters 906, 908 relative to each other, as further described above.

In some embodiments, the flexible arms 918 can be operably coupled to the handle 905. For example, the delivery apparatus 904 can include linkage and/or wires (not shown) that extend proximally (e.g., through the first and/or second catheters 906, 908) from the flexible arms 918 to or adjacent the handle 905. The linkage and/or wires can be configured to control, move, and/or adjust the positioning, configuration, and/or gripping force (i.e., the compressive force applied by the flexible arms 918 on an object or objects (e.g., native leaflets) disposed between the flexible arms 918) of the flexible arms 918. In some embodiments, the linkage and/or wires can be configured such that the flexible arms 918 can be independently operable relative to each other (e.g., each flexible arm 918 can be operably coupled to a separate linkage and/or wire). In some embodiments, the linkage and/or wires can be operably coupled to one or more control knobs that are disposed on the handle 905 or other portion of the delivery apparatus 904. The control knobs can be configured to control, move, and/or adjust the linkage and/or wires and thus the flexible arms 918.

The flexible arms 918 can also include one or more radiopaque elements (not shown). The radiopaque elements can be disposed on the flexible arms 918 and can allow a physician to monitor the positioning of the flexible arms 918 during an implantation procedure. In some embodiments, the radiopaque elements can be integrally formed with the flexible arms 918 (e.g., co-molded). In other embodiments, the radiopaque elements can be separately formed and then attached to the flexible arms 918 such as with an adhesive.

In some embodiments, the radiopaque elements can be disposed on the distal portions 924 of the flexible arms 918.

In some embodiments, as shown, the distal portions 924 of the flexible arms 918 can be formed as a paddle-like portion that is relatively larger than the proximal portions 922 of the flexible arms 918. These paddle-like distal portions 924 can provided a relatively large surface area that can contact and or grip native leaflets of heart.

The flexible arms 918 can be formed from various materials, such as metals, polymers, composites, etc. For example, in some embodiments, the flexible arms 918 can be formed from relatively elastic materials such as stainless steel, Nitinol, shape-memory polymers, etc. The flexible arms 918 can include covers made from a relatively soft material, such as cloth, fabric, or natural tissue, to reduce trauma to the surrounding heart tissue and/or to increase friction between the flexible arms 918 and native heart tissue (e.g., native leaflets).

Referring to FIGS. 40 and 41, the third catheter 910 can comprise an elongate shaft having a distal end portion 926. The distal end portion 926 of the third catheter 910 can be releasably coupled to the prosthetic heart valve 902 in various ways such as with sutures, interlocking mating features, etc. Additional details regarding releasably coupling a prosthetic heart valve to a delivery apparatus can be found, for example, in U.S. Pat. No. 8,652,202. As such, the third catheter 910 can be used to move the prosthetic heart valve 902 relative to the first and/or second catheters 906, 908. This can be accomplished, for example, by moving the third catheter 910 axially (i.e., proximally and/or distally) relative to the first and/or second catheters 906, 908.

In some embodiments, the delivery apparatus 904 can be configured to deliver a prosthetic heart valve to a native heart valve of a patient. The delivery apparatus 904 can also be configured for various types of delivery approaches (e.g., transapical, transventricular, transseptal, transfemoral, etc.). For example, FIGS. 38-41 show the delivery apparatus 904 being used to deliver the prosthetic heart valve 902 to a native mitral valve 1002 of a patient's heart 1000 using a transapical approach.

The prosthetic heart valve 902 can be implanted in the native mitral valve 1002 by radially compressing the prosthetic heart valve 902 to the compressed configuration and positioning the prosthetic heart valve 902 within the sheath portion 916 of the second catheter 906, as shown in FIG. 38. As also shown in FIG. 38, the flexible arms 918 of the second catheter 908 can be radially compressed to the first configuration and positioned within the sheath portion 912 of the first catheter 906.

With the delivery assembly 900 in this configuration, a distal end portion of the delivery assembly 900 can be advanced into the left ventricle 1004 of the patient's heart 1000. This can be accomplished, for example, by inserting an introducer (not shown) into the left ventricle 1004 and inserting the distal end portion of the delivery assembly 900 into and through the introducer and into the left ventricle 1004. As shown in FIG. 38, the distal end portion of the delivery assembly 900 can be positioned adjacent the patient's native mitral valve leaflets 1006. The flexible arms 918 of the second catheter 908 can be moved from the first configuration to the second configuration by proximally retracting the first catheter 906 relative to the second catheter 908, as shown in FIG. 39.

The native leaflets 1006 can be captured or secured between the flexible arms 918 by moving the flexible arms 918 from the second configuration to the third configuration by proximally retracting the second catheter 908 relative to the first catheter 906, as shown in FIG. 40. In this configuration, the flexible arms 918 can be positioned against the ventricular side of the native leaflets 1006 and can hold or stabilize the native leaflets 1006, as shown in FIGS. 40 and 41, for subsequent deployment of the prosthetic heart valve 902.

While holding the native leaflets 1006 with the flexible arms 918, the prosthetic heart valve 902 can be deployed from the sheath portion 916 of the second catheter 908 by distally advancing the third catheter 910 relative to the first and second catheters 906, 906 such that the prosthetic heart valve 902 is disposed distally relative to the distal end portions 914, 902 of the first and second catheters 906, 908, respectively. The prosthetic heart valve 902 can then radially expand (and/or be expanded) from the compressed configuration to the expanded configuration (e.g., by self-expanding and/or mechanically expanding), as shown in FIG. 41. The prosthetic heart valve 902 can then be desirably positioned relative to the native mitral valve 1002 by moving the prosthetic heart valve 902 with the third catheter 910. The prosthetic heart valve 902 can be secured to the native leaflets 1006 and/or the native mitral valve annulus, for example, using securing elements 928 (e.g., similar to the projections 36 of the prosthetic valve 10).

Holding the native leaflets 1006 while the prosthetic heart valve 902 is deployed, positioned, and/or secured can make it relatively easier for the physician to quickly, securely, and accurately position the prosthetic heart valve 902 in the native mitral valve 1002 because the movement of the native leaflets 1006 is restricted. This can, for example, help to ensure that the securing elements 928 of the prosthetic heart valve 902 penetrate the tissue of the native leaflets 1006. In addition, the native leaflets 1006 can be drawn toward each other and against the outer surface of the prosthetic heart valve 902 by decreasing the distance between the flexible arms 918 (through manipulation of the catheters 906, 908) to enhance the attachment of the securing elements 928 of the prosthetic heart valve to the native leaflets 1006.

Once the prosthetic heart valve 902 is secured, the prosthetic heart valve 902 can be released from the third catheter 910, and the distal end portions of the second and third catheters 908, 910 can be proximally retracted into the sheath portion 912 of the first catheter 906. The delivery apparatus 904 can then be proximally retracted through the introducer and removed from the patient's body.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

The invention claimed is:

1. A prosthetic heart valve for replacing a native mitral valve, comprising:

a first frame comprising a main body and an atrial flange, the main body having an inflow end sized for placement in a patient's left atrium and an outflow end sized for placement in a patient's left ventricle, wherein the main body includes a plurality of struts forming a plurality of circumferential rows of cells, a plurality of rows of barbs extending from junctions of the struts, the atrial flange extending radially outwardly and in an atrial direction from the inflow end of the main body, wherein the rows of barbs includes a first row of barbs and a second row of barbs, wherein the first row of barbs is circumferentially offset relative to the second row of barbs, wherein each of the barbs comprises a fixed end and a free end, and wherein the free end is disposed radially outwardly and toward the inflow end relative to the fixed end, and wherein the atrial flange has a non-circular shape that corresponds to a shape of the patient's native mitral valve anatomy;

a cover disposed on a radially inner side of the atrial flange and on a radially outer side of the atrial flange, wherein the cover is configured to reduce paravalvular leakage;

a second frame disposed within the first frame and having a cylindrical shape; and a valve structure coupled to the second frame and comprising a plurality of leaflets.

2. The prosthetic heart valve of claim 1, wherein the first frame and the second frame both comprise nitinol.

3. The prosthetic heart valve of claim 1, wherein the first frame or the second frame comprises exactly three eyelets extending therefrom.

4. The prosthetic heart valve of claim 1, wherein the leaflets include bovine pericardial tissue.

5. A system for replacing a native mitral valve, comprising:

a self-expanding prosthetic heart valve, wherein the self-expanding prosthetic heart valve comprises:

a support frame comprising a main body and an atrial flange, the main body having an inflow end configured to be oriented toward a patient's left atrium and an outflow end configured to be oriented toward a patient's left ventricle, wherein the main body includes a plurality of struts forming a plurality of circumferential rows of cells and two or more rows of projections extending from junctions of the struts, wherein the rows of projections includes a first row of projections and a second row of projections, wherein the first row of projections is circumferentially offset relative to the second row of projections, wherein each of the projections has a fixed end and a free end, and wherein the free end is disposed radially outwardly and toward the inflow end relative to the fixed end, wherein the atrial flange extends radially outwardly and in an atrial direction from the inflow end of the main body, and wherein the atrial flange has an oval shape for conforming to the patient's native mitral valve anatomy;

a cover disposed on a radially inner side of the atrial flange and on a radially outer side of the atrial flange, wherein the cover is configured to reduce paravalvular leakage;

a valve frame disposed within the support frame and having a cylindrical shape; and a valve structure coupled to the valve frame and comprising a plurality of leaflets; and a delivery apparatus for implanting the self-expanding prosthetic heart valve, wherein the delivery apparatus comprises:

a sheath configured to receive and retain the self-expanding prosthetic heart valve in a radially compressed configuration; and a plurality of positioning members disposed within and axially movable relative to the sheath, wherein the positioning member are releasably coupled to the self-expanding prosthetic heart valve.

6. The system of claim 5, wherein the self-expanding prosthetic heart valve and the delivery apparatus are configured for a transventricular delivery procedure.

7. The system of claim 5, wherein the support frame and the valve frame are radially spaced apart from each other at the outflow end.

8. The system of claim 5, wherein in the cover extends over the inflow end of the support frame.

9. The system of claim 5, wherein the self-expanding prosthetic heart valve further comprises a plurality of eyelets, and wherein each of the eyelets is spaced circumferentially apart from an adjacent eyelet.

10. A prosthetic heart valve comprising:

a first nitinol frame comprising a main body and an atrial flange, the main body comprising an inflow end configured to be oriented toward a patient's left atrium and an outflow end configured to be oriented toward a patient's left ventricle, wherein the main body comprises a plurality of struts forming a plurality of circumferential rows of cells, a plurality of rows of barbs extending from junctions of the struts, the atrial flange extending radially outwardly and in an atrial direction from the inflow end of the main body, wherein each of the barbs comprises a fixed end and a free end, wherein the free end is disposed radially outwardly and toward the inflow end relative to the fixed end, wherein the rows of barbs includes a first row of barbs and a second row of barbs, wherein the first row of barbs is circumferentially offset relative to the second row of barbs, and wherein the atrial flange comprises a non-circular shape corresponding to a shape of the patient's native mitral valve anatomy;

a cover disposed on a radially inner side of the atrial flange and on a radially outer side of the atrial flange, wherein the cover is configured to reduce paravalvular leakage;

a second nitinol frame disposed within the first nitinol frame and having a cylindrical shape; and a valve structure coupled to the second nitinol frame and comprising a plurality of leaflets, wherein the leaflets include bovine pericardial tissue, wherein the first nitinol frame or the second nitinol frame comprises exactly three eyelets extending therefrom.

* * * * *